US012201825B2

(12) United States Patent
Robinson et al.

(10) Patent No.: US 12,201,825 B2
(45) Date of Patent: Jan. 21, 2025

(54) MECHANICAL FEEDTHROUGHS FOR IMPLANTABLE MEDICAL DEVICE

(71) Applicant: Medtronic, Inc., Minneapolis, MN (US)

(72) Inventors: Reginald D. Robinson, Plymouth, MN (US); Mary E. Robischon, Minneapolis, MN (US); Rodney J. Haberle, Zimmermann, MN (US); Gerald G. Lindner, Lino Lakes, MN (US); Don A. Rutledge, Corcoran, MN (US); Jason R. Simoneau, Cambridge, MN (US)

(73) Assignee: Medtronic, Inc., Minneapolis, MN (US)

( * ) Notice: Subject to any disclaimer, the term of this patent is extended or adjusted under 35 U.S.C. 154(b) by 906 days.

(21) Appl. No.: 16/936,092

(22) Filed: Jul. 22, 2020

(65) Prior Publication Data
US 2020/0346003 A1 Nov. 5, 2020

Related U.S. Application Data

(63) Continuation of application No. 14/822,763, filed on Aug. 10, 2015, now abandoned.
(Continued)

(51) Int. Cl.
*A61N 1/36* (2006.01)
*A61N 1/05* (2006.01)
(Continued)

(52) U.S. Cl.
CPC ......... *A61N 1/0539* (2013.01); *A61N 1/0534* (2013.01); *A61N 1/18* (2013.01);
(Continued)

(58) Field of Classification Search
CPC .. A61N 1/0526; A61N 1/0529; A61N 1/0531; A61N 1/0534; A61N 1/0539;
(Continued)

(56) References Cited

U.S. PATENT DOCUMENTS

| 1,702,762 | A | * | 2/1929 | Brubaker | .............. G01F 15/065 |
| | | | | | 324/154 R |
| 2,449,772 | A | * | 9/1948 | Gilman | ................... F04D 13/10 |
| | | | | | 74/18.1 |

(Continued)

FOREIGN PATENT DOCUMENTS

WO    2014001501 A2    1/2014

OTHER PUBLICATIONS

Jiang, G.,. "Design challenges of implantable pressure monitoring system," Frontiers in Neuroscience, vol. 4, Article 2, Feb. 2010, 4 pp. https://doi.org/10.3389/neuro.20.002.2010.

(Continued)

Primary Examiner — Eugene T Wu
(74) Attorney, Agent, or Firm — Shumaker & Sieffert, P.A.

(57) ABSTRACT

An implantable medical device assembly comprises a sealed housing; a motor including a rotating output shaft within the sealed housing; a first coaxial shaft within the sealed housing, the first coaxial shaft being mechanically coupled to the rotating output shaft such that rotation of the rotating output shaft drives rotation of the first coaxial shaft; a second coaxial shaft external to the sealed housing, the second coaxial shaft being in axial alignment with the first coaxial shaft; an oscillating component mechanically coupling the first coaxial shaft to the second coaxial shaft, wherein rotation of the rotating first coaxial shaft drives the oscillation of the oscillating component, wherein the oscillation of the oscillating component drives rotation of the second (Continued)

coaxial shaft; and a flexible seal including the oscillating component. The sealed housing and the flexible seal combine to form a substantially sealed enclosure encasing the motor and the first coaxial shaft.

18 Claims, 20 Drawing Sheets

Related U.S. Application Data

(60) Provisional application No. 62/035,843, filed on Aug. 11, 2014, provisional application No. 62/035,862, filed on Aug. 11, 2014, provisional application No. 62/035,765, filed on Aug. 11, 2014, provisional application No. 62/035,776, filed on Aug. 11, 2014.

(51) Int. Cl.
*A61N 1/18* (2006.01)
*A61N 1/375* (2006.01)

(52) U.S. Cl.
CPC ....... *A61N 1/3605* (2013.01); *A61N 1/37514* (2017.08); *A61N 1/3752* (2013.01); *A61N 1/36182* (2013.01)

(58) Field of Classification Search
CPC .... A61N 2001/083; A61N 2001/36014; A61N 2001/36017; A61N 2001/36025; A61N 2001/36039; A61N 2001/3605; A61N 2001/36125; A61N 2001/36128; A61N 2001/36132; A61N 2001/36135; A61N 2001/36139; A61N 2001/36182; A61N 2001/375; A61N 2001/3752; A61N 2001/3754; A61B 5/6864; A61B 5/6868; A61B 5/6885; A61B 5/6886
See application file for complete search history.

(56) References Cited

U.S. PATENT DOCUMENTS

| | | | |
|---|---|---|---|
| 2,454,340 A * | 11/1948 | Reichel | F16J 15/525 74/18.1 |
| 2,497,867 A | 2/1950 | Cymmer | |
| 2,746,302 A * | 5/1956 | Bakke | G01C 19/38 74/18.1 |
| 2,837,926 A | 6/1958 | Korsgren, Sr. et al. | |
| 2,978,914 A * | 4/1961 | Gut | F16J 15/525 74/18.1 |
| 3,051,008 A | 8/1962 | Hamren | |
| 3,082,632 A | 3/1963 | Vulliez | |
| 3,999,403 A | 12/1976 | Bower et al. | |
| 4,646,579 A | 3/1987 | Klein | |
| 4,767,396 A | 8/1988 | Powers | |
| 4,802,458 A | 2/1989 | Finsterwald et al. | |
| 5,079,467 A | 1/1992 | Dorman | |
| 5,178,024 A | 1/1993 | Leclaire et al. | |
| 5,368,040 A | 11/1994 | Carney | |
| 5,372,124 A | 12/1994 | Takayama et al. | |
| 6,115,634 A | 9/2000 | Donders et al. | |
| 6,119,537 A | 9/2000 | Jost | |
| 6,161,047 A | 12/2000 | King et al. | |
| 6,491,039 B1 | 12/2002 | Dobak, III | |
| 6,745,079 B2 | 6/2004 | King | |
| 6,795,737 B2 | 9/2004 | Gielen et al. | |
| 6,806,595 B2 | 10/2004 | Quarre | |
| 7,181,288 B1 | 2/2007 | Rezai et al. | |
| 7,715,924 B2 | 5/2010 | Rezai et al. | |
| 7,831,308 B2 | 11/2010 | Rezai et al. | |
| 8,116,886 B2 | 2/2012 | Simaan et al. | |
| 8,391,957 B2 | 3/2013 | Carlson et al. | |
| 8,529,476 B2 | 9/2013 | Govari | |
| 8,876,371 B2 | 11/2014 | Behrend et al. | |
| 9,447,853 B2 * | 9/2016 | DiMarco | F16J 15/525 |
| 2004/0102828 A1 | 5/2004 | Lowry et al. | |
| 2005/0075680 A1 | 4/2005 | Lowry et al. | |
| 2005/0075681 A1 * | 4/2005 | Rezai | A61N 1/0531 607/48 |
| 2005/0131506 A1 | 6/2005 | Rezai et al. | |
| 2006/0030893 A1 | 2/2006 | Laske et al. | |
| 2007/0086904 A1 | 4/2007 | Gray | |
| 2009/0287271 A1 | 11/2009 | Blum et al. | |
| 2010/0023021 A1 | 1/2010 | Flaherty | |
| 2010/0100152 A1 * | 4/2010 | Martens | A61B 5/24 607/45 |
| 2010/0114283 A1 | 5/2010 | King | |
| 2012/0029590 A1 | 2/2012 | Daneshvar et al. | |
| 2014/0336453 A1 | 11/2014 | Ueki et al. | |
| 2015/0343203 A1 * | 12/2015 | Machado | A61N 1/37235 607/116 |
| 2016/0038733 A1 | 2/2016 | Robinson et al. | |
| 2017/0258447 A1 | 9/2017 | Lee et al. | |

OTHER PUBLICATIONS

Jiang et al., "Technology Advances and Challenges in Hermetic Packaging for Implantable Medical Devices," Chapter in Implantable Neural Prostheses 2, Biological and Medical Physics, Biomedical Engineering, Springer 2010, 36 pp. (Applicant points out, in accordance with MPEP 609.104(a), that the year of publication, 2010, is sufficiently earlier than the effective U.S. filing date, so that the particular month of publication is not in issue.).

Joung, Y. H., "Development of Implantable Medical Devices: From an Engineering Perspective," International Neurourology Journal, vol. 17, No. 3, Sep. 2013, 9 pp. http://doi.10.5213/inj.2013.17.3.98.

International Search Report and Written Opinion of International Application No. PCT/US2015/044523, mailed Dec. 22, 2015, 10 pp.

International Preliminary Report on Patentability from International Application No. PCT/US2015/044523, mailed Feb. 23, 2017, 7 pp.

Prosecution History from U.S. Appl. No. 14/822,763, dated Sep. 21, 2016 through May 22, 2020, 306 pp.

U.S. Appl. No. 62/035,862, by Reginald D. Robinson, filed Aug. 11, 2014.

U.S. Appl. No. 62/035,765, by Reginald D. Robinson, filed Aug. 11, 2014.

U.S. Appl. No. 62/035,776, by Reginald D. Robinson, filed Aug. 11, 2014.

* cited by examiner

MECHANICAL FEEDTHROUGHS FOR IMPLANTABLE MEDICAL DEVICE

This application is a continuation of U.S. patent application Ser. No. 14/822,763, filed Aug. 10, 2015, which claims the benefit of U.S. Provisional Patent Application Ser. No. 62/035,765, filed Aug. 11, 2014, U.S. Provisional Patent Application Ser. No. 62/035,776, filed Aug. 11, 2014, U.S. Provisional Patent Application Ser. No. 62/035,843, filed Aug. 11, 2014, and U.S. Provisional Patent Application Ser. No. 62/035,862, filed Aug. 11, 2014. The entire contents of each of these applications are incorporated by reference herein.

TECHNICAL FIELD

The present disclosure relates to medical devices and, more particularly, to medical leads configured for delivering electrical stimulation therapy and/or sensing electrical physiological signals.

BACKGROUND

Implantable electrical stimulators may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. In general, an implantable stimulator delivers neurostimulation therapy in the form of electrical pulses. An implantable stimulator may deliver neurostimulation therapy via one or more medical leads that include electrodes located proximate to target tissues of the brain, the spinal cord, pelvic nerves, peripheral nerves, or the stomach of a patient. Hence, stimulation may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, such as functional electrical stimulation (FES) to promote muscle movement or prevent atrophy.

Stimulation therapy may be more effective with accurate placement of the medical leads within the targeted region of a patient, such as the brain, central nervous system or urological tract for example. Medical leads may incorporate anchoring systems to passively hold medical leads in place once positioned by a clinician during an implantation procedure. However, occurrences of misplaced or dislodged leads may still impact clinical outcomes for some patients, and may even require surgical repositioning of implanted medical leads. Surgical repositioning of misplaced or dislodged leads causes increased risks, discomfort and inconvenience for patients and consumes additional healthcare resources.

SUMMARY

This disclosure includes techniques associated with the design, manufacture and use of mechanically adjustable medical leads. Techniques as described herein may facilitate post-surgical mechanical repositioning of medical lead electrodes. Disclosed techniques include lead designs, mechanical feedthrough designs as well as techniques for use and manufacture of the same. Some disclosed techniques, such as mechanical feedthrough designs, have applicability well beyond medical leads. Disclosed mechanical feedthrough designs may be also used with other medical devices to simultaneously provide torque transmission and hermetic isolation between chambers of an implantable medical device. This would enable implantable device therapy options requiring the transmission of torque across a hermetic boundary.

In one example, this disclosure is directed to an implantable medical device assembly comprising: a sealed housing; a motor within the sealed housing, the motor including a rotating output shaft; a first coaxial shaft within the sealed housing, the first coaxial shaft being mechanically coupled to the rotating output shaft such that rotation of the rotating output shaft drives rotation of the first coaxial shaft; a second coaxial shaft external to the sealed housing, the second coaxial shaft being in axial alignment with the first coaxial shaft; an oscillating component mechanically coupling the first coaxial shaft to the second coaxial shaft, wherein rotation of the rotating first coaxial shaft drives the oscillation of the oscillating component, wherein the oscillation of the oscillating component drives rotation of the second coaxial shaft; and a flexible seal including the oscillating component, wherein the sealed housing and the flexible seal combine to form a substantially sealed enclosure encasing the motor and the first coaxial shaft.

In another example, this disclosure is directed to a method of adjusting a mechanically adjustable medical lead. The mechanically adjustable medical lead includes an electrode and a rotatable member, the rotatable member being mechanically coupled to the electrode. The method comprises operating a motor within a hermetically sealed enclosure to drive the rotatable member of the medical lead and move a position of the electrode to adjust a spacing between a proximal end of the medical lead and the electrode.

The details of the present disclosure are set forth in the accompanying drawings and the description below. Other features, objects, and benefits of the present disclosure will be apparent from the description and drawings, and from the claims.

DETAILED DESCRIPTION

Techniques as disclosed herein may permit clinicians administering therapy via medical leads to reposition one or more electrodes of an implanted medical lead in a non-invasive manner. Techniques as disclosed herein may facilitate post-surgical (e.g., post-implantation) mechanical repositioning of medical lead electrodes. Such techniques may be used to achieve improved therapy outcomes by permitting repositioning while limiting the incidence of additional surgical procedures among patients as well as potentially providing a higher level of electrode placement precision for all patients.

As one example, the disclosed techniques may limit the need for surgical repositioning as well as facilitate medical lead implantation within juvenile patients who are still growing. For example, juvenile dystonia patients and others with fast-growing brains and skulls, who might otherwise benefit from DBS therapy, may not currently be candidates to receive the therapy as repeated neurosurgical procedures may be required to account for patient growth over time.

Furthermore, post-surgical mechanical repositioning of medical lead electrodes may allow more precise electrode positioning than positioning only via surgical means. For example, cannulation error and limitations on surgical dexterity may impose inherent limits on the positioning accuracy and precision of electrodes on medical leads during an implantation procedure.

Figure 1:
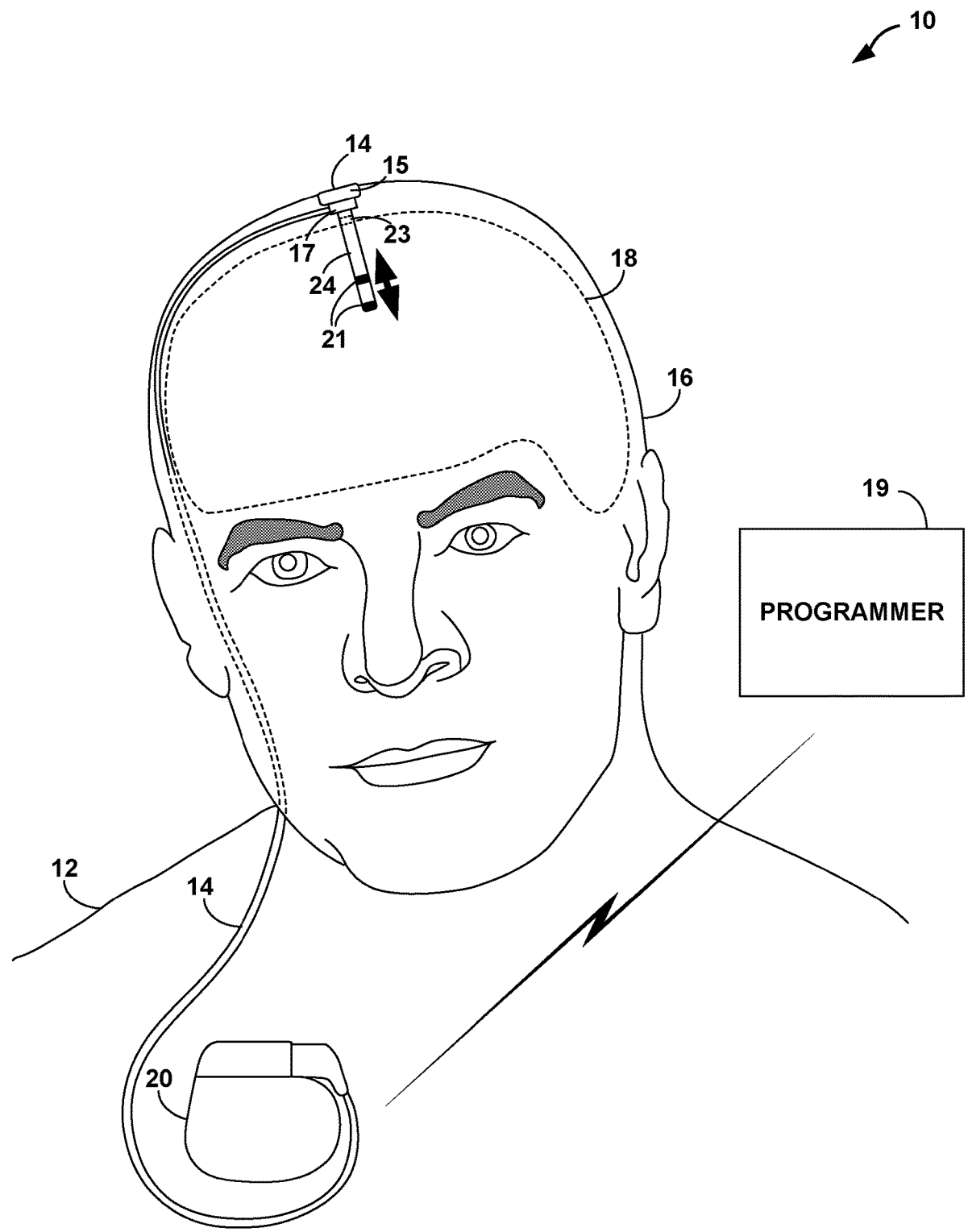
FIG. 1 is a conceptual diagram illustrating an example stimulation system with a mechanically adjustable medical lead implanted in the brain of a patient.

FIG. 1 is a conceptual diagram illustrating an example stimulation system with a mechanically adjustable medical lead implanted in the brain of a patient. As shown in FIG. 1, stimulation system 10 includes implantable medical device (IMD) 20 and mechanically adjustable medical lead 14 implanted within patient 12. Specifically, mechanically adjustable medical lead 14 enters through cranium 16 and is implanted within brain 18 to deliver deep brain stimulation (DBS). One or more electrodes of mechanically adjustable medical lead 14 provides electrical pulses to surrounding anatomical regions of brain 18 in a therapy that may alleviate a condition of patient 12.

Mechanically adjustable medical lead 14 includes medical lead body 24 with electrodes 21, motor 15 and screw mechanism 17. Mechanically adjustable medical lead 14 also may include optional force sensor 23, which is configured to measure a resistance to movement of mechanically adjustable medical lead 14. In some examples, more than one mechanically adjustable medical leads may be implanted within brain 18 of patient 12 to stimulate multiple anatomical regions of the brain. As shown in FIG. 1, system 10 may also include a programmer 19, which may be a handheld device, portable computer, or workstation that provides a user interface to a clinician. The clinician interacts with the user interface to program stimulation parameters and optionally to non-invasively adjust the positioning of one or more electrodes of mechanically adjustable medical lead 14.

DBS may be used to treat dysfunctional neuronal activity in the brain that manifests as diseases or disorders such as Huntington's disease, Parkinson's disease, or movement disorders. Symptoms of these diseases can be lessened or eliminated with electrical stimulation therapy. Certain anatomical regions of brain 18 are responsible for producing the symptoms of such brain disorders. As one example, stimulating an anatomical region, such as the Substantia Nigra, in brain 18 may reduce the number and magnitude of tremors experienced by patient 12. Other anatomical regions may include the subthalamic nucleus, globus pallidus interna, ventral intermediate, and zona inserta. Anatomical regions such as these are targeted by the clinician during mechanically adjustable medical lead 14 implantation. In other words, the clinician may attempt to position the medical lead as close to these regions as possible.

The clinician interacts with the user interface to manually select and program certain electrodes of mechanically adjustable medical lead 14 and adjust the resulting stimulation field with the anatomical regions as guides, or define one or more stimulation fields only affect anatomical regions of interest. Once the clinician has defined the one or more stimulation fields, system 10 automatically generates the stimulation parameters associated with each of the stimulation fields and transmits the parameters to IMD 20.

The stimulation field defined by the clinician using a user interface described herein is associated with certain stimulation parameter values. Programmer 19 generates the stimulation parameters required by the stimulation field and wirelessly transmits the parameters to IMD 20. The parameters may be generated automatically or based on manual selection by a patient or clinician user. The parameters may also be saved on programmer 19 for review at a later time. In some cases, programmer 19 may not be capable of generating stimulation parameters that can produce the defined stimulation field within brain 18. Programmer 19 may display an error message to the clinician alerting the clinician to adjust the stimulation field. Programmer 19 may also display a reason why the stimulation field cannot be provided, such as the field is too large or an electrode is malfunctioning and cannot be used. Other errors may also be displayed to the clinician.

Generally, the user interface is not used to provide real-time programming to IMD 20. The clinician will use the user interface to define stimulation fields, and programmer 19 automatically generates the stimulation parameters when the clinician has determined the stimulation field is ready for therapy. In this manner, stimulation therapy perceived by patient 12 does not change at the same time the clinician changes the stimulation field. However, the user interface could be used as such in a real-time programming environment to provide immediate feedback to the clinician.

System 10 may also include multiple medical leads 14 or electrodes on medical leads of other shapes and sizes. The user interface may allow the clinician to program each medical lead simultaneously or require the clinician to program each medical lead separately. In some DBS patients, two medical leads 14 are implanted at symmetrical locations within brain 18 for bilateral stimulation. In particular, a first medical lead is placed in the right hemisphere of brain 18 and a second medical lead is placed at the same location within the left hemisphere of the brain. Programmer 19 may allow the clinician to create a stimulation field for the first medical lead and create a mirrored stimulation field for the second medical lead. The clinician may be able to make fine adjustment to either stimulation field to accommodate the slight anatomical region differences between the left and right hemispheres.

While mechanically adjustable medical lead 14 is described for use in DBS applications as an example, mechanically adjustable medical lead 14, or other medical leads, may be implanted at any other location within patient 12. For example, mechanically adjustable medical lead 14 may be implanted near the spinal cord, pudendal nerve, sacral nerve, or any other nervous or muscle tissue that may be stimulated. The user interface described herein may be used to program the stimulation parameters of any type of stimulation therapy. Therapy may also be changed if medical leads migrate to new locations within the tissue or patient 12 no longer perceives therapeutic effects of the stimulation.

As mentioned above, mechanically adjustable medical lead 14 includes motor 15 and screw mechanism 17, which facilitates the non-invasively repositioning of one or more of electrodes 21. In one example, motor 15 may include one or more reversible, high-resolution, stepper-motors to drive screw mechanism 17 based in power and/or control signals from IMD 20. In the same or different examples, screw mechanism 17 may include fine-pitch threaded screws that facilitate altering the overall length of medical lead 14, adjusting the spacing or "pitch" between electrodes 21, angular displacement of electrodes 21, radial displacement from the axis-of-insertion of electrodes 21, and/or other electrode positioning parameters of medical lead 14.

System 10 may employ "active-positioning" of electrodes 21 of medical lead 14. For example, system 10 may monitor a physiological condition of the patient based on the positioning of electrodes 21 in order to determine a precise desired positioning of electrodes 21. In the same or different examples, system 10 may monitor physiological conditions of patient 12 actively or passively via electrodes 21 at different positions of electrodes 21. Therapy parameters may include position settings and different stimulation and/or sensing therapy parameter sets may have different, and even unique, prescribed position settings. In the same or different examples, system 10 may actively adapt position settings according to monitored physiological parameters of patient 12, for example, to achieve improved efficacy of a stimulation treatment via electrodes 21 or improved sensing via electrodes 21.

In some examples, system 10 may monitor a force signal representing the resistance to movement of the position of the electrode(s) from force sensor 23 and repositioning of electrodes of medical lead 14 may be based on the resistance to movement of the position of the electrodes as indicated by force sensor 23. In some examples, force sensor 23 may include a piezoelectric sensor. In the same or different examples, force sensor 23 may include a current sensor and force may be measured by monitoring current required to operate motor 15. In one particular example, system 10 may limit movement of the position of electrodes 21 to prevent the resistance to movement of the position of the electrode from exceeding a predefined value.

Figure 2:
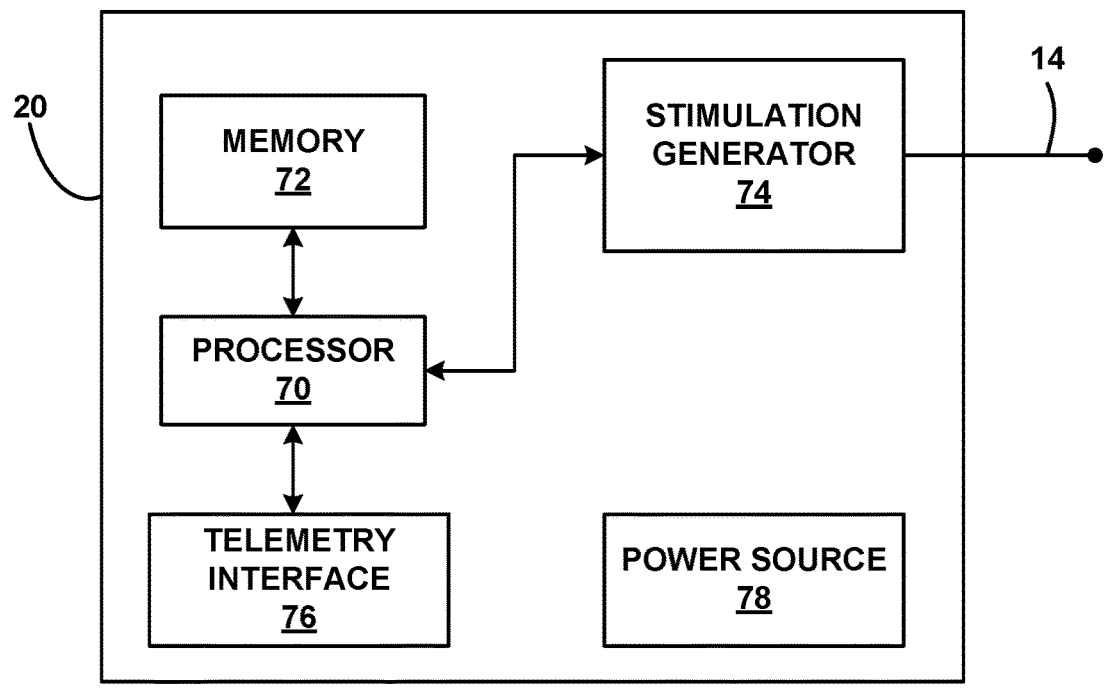
FIG. 2 is a functional block diagram of an example implantable medical device that generates electrical stimulation pulses.

FIG. 2 is a functional block diagram of an example implantable medical device that generates electrical stimulation signals. In the example of FIG. 2, IMD 20 includes a processor 70, memory 72, stimulation generator 74, telemetry interface 76, and power source 78. As shown in FIG. 2, stimulation generator 74 is coupled to mechanically adjustable medical lead 14. Alternatively, stimulation generator 74 may be coupled to a different number of medical leads as needed to provide stimulation therapy to patient 12. Each lead 14 may include one, two, or more electrodes that are coupled to stimulation generator 74 via respective conductors within the lead.

Processor 70 controls stimulation generator 74 to deliver electrical stimulation therapy according to programs generated by a user interface and stored in memory 72 and/or received from programmer 19 via telemetry interface 76. As an example, a new program received from programmer 19 may modify the electrode configuration and amplitude of stimulation. Processor 70 may communicate with stimulation generator 74 to change the electrode configuration used during the therapy and modify the amplitude of stimulation. Processor 70 may then store these values in memory 72 to continue providing stimulation according to the new program. Processor 70 may stop the previous program before starting the new stimulation program as received from programmer 19. In some examples, intensity of the stimulation signal may be ramped down or ramped up as a program is being turned off or turned on. In this manner, no abrupt stimulation changes may be perceived by patient 12. Intensity may be controlled, for example, by varying one or more of voltage or current amplitude, pulse width and/or pulse frequency. A ramp up of the new program may provide patient 12 time to stop stimulation if the new program is uncomfortable.

Processor 70 may comprise any one or more of a microprocessor, digital signal processor (DSP), application specific integrated circuit (ASIC), field-programmable gate array (FPGA), or other digital logic circuitry. Memory 72 stores instructions for execution by processor 70, for example, instructions that when executed by processor 70 cause the processor and IMD to provide the functionality ascribed to them herein, as well as stimulation programs. Memory 72 may include any one or more of a random access memory (RAM), read-only memory (ROM), electronically-erasable programmable ROM (EEPROM), flash memory, or the like.

Stimulation generator 74 may provide stimulation in the form of pulses to patient 12. Alternatively, stimulation generator 74 may provide therapy in the form of some continuous signal such as a sine wave or other non-pulse therapy. Stimulation parameters for each stimulation program may include electrode configuration, current or voltage amplitude, pulse width, pulse rate, and/or duty cycle. Other parameters may be used depending on the therapy to be provided to patient 12. Stimulation generator 74 may independently utilize any of electrodes 21. In this manner, stimulation generator 74 may be utilized to deliver stimulation via numerous different electrode configurations to provide therapy for a wide variety of patient conditions. In addition, stimulation generator 74 may test the functionality of electrodes on mechanically adjustable medical lead 14. Based upon the impedance testing, specific electrodes may be removed from possible use in therapy when the test indicates that the impedance is above or below normal operating limits.

An electrode combination is a selected subset of one or more electrodes located on one or more implantable medical leads coupled to an implantable stimulator. The electrode combination also refers to the polarities of the electrode segments in the selected subset. The electrode combination, electrode polarities, voltage or current amplitude, pulse width and pulse rate together define a program for delivery of electrical stimulation therapy by an implantable stimulator via an implantable medical lead or medical leads. By selecting particular electrode combinations, including selected electrodes and polarities, a physician can target particular anatomic structures. By selecting values for amplitude, pulse width and pulse rate, the physician can attempt to optimize the electrical therapy delivered to the patient via the selected electrode combination or combinations.

In general, a clinician selects values for a number of programmable parameters in order to define the electrical stimulation therapy to be delivered by the implantable stimulator to a patient. For example, the clinician ordinarily selects a combination of electrodes carried by one or more implantable medical leads, and assigns polarities to the selected electrodes. In addition, the clinician selects an amplitude, which may be a current or voltage amplitude, a pulse width and a pulse rate for stimulation pulses to be delivered to the patient. A group of parameters, including electrode combination, electrode polarity, amplitude, pulse width and pulse rate, may be referred to as a program in the sense that they drive the neurostimulation therapy to be delivered to the patient. In some applications, an implantable stimulator may deliver stimulation therapy according to multiple programs either simultaneously or on a time-interleaved, overlapping or non-overlapping, basis.

A clinician may further select positioning parameters for electrodes of medical lead 14. For example, the clinician may employ "active-positioning" of electrodes 21 of medical lead 14 in which processor 70 monitors a physiological condition of the patient based on the positioning of electrodes 21 in order to determine a precise desired positioning of electrodes 21. In the same or different examples, processor 70 may monitor physiological conditions of patient 12 actively or passively via electrodes 21 at different positions of electrodes 21. Therapy parameters may include position settings and different stimulation and/or sensing therapy parameter sets may have different, even unique, prescribed position settings.

In some examples, a clinician may select positioning parameters based on the resistance to movement of the position of the electrode(s) from force sensor 23 and repositioning of electrodes of medical lead 14 may be based on the resistance to movement of the position of the electrodes as indicated by force sensor 23. In one particular example, a clinician may select parameters to limit movement of the position of electrodes 21 to prevent the resistance to movement of the position of the electrode from exceeding a predefined value.

In the same or different examples, a clinician may select positioning parameters based on a monitored physiological condition of the patient. For example, electrodes 21 may be used to monitor electrical signals like brain activity, and whereby the system responds to those signals by mechanically moving/repositioning itself in a manner that helps to enhance the detection of such signals, and thus help to optimize the signal/noise ratio of the detection function, and or optimize the delivery of the corresponding therapeutic signal that is generated in response to the detected signal. The positioning parameters may represent a closed-loop response to monitored physiological conditions of the patient.

Telemetry interface 76 may include circuitry known in the art for facilitating wireless telemetry, for example, via radio frequency (RF) communication or proximal inductive interaction with similar circuitry within external programmer 19. Power source 78 delivers operating power to the components of IMD 20. Power source 78 may include a battery and a power generation circuit to produce the operating power. In some examples, the battery may be rechargeable to allow extended operation. Recharging may be accomplished through proximal inductive interaction between an external charger and an inductive charging coil within IMD 20. In other examples, non-rechargeable batteries may be used. As a further alternative, an external power supply could transcutaneously power IMD 20 whenever stimulation is needed or desired.

Figure 3:
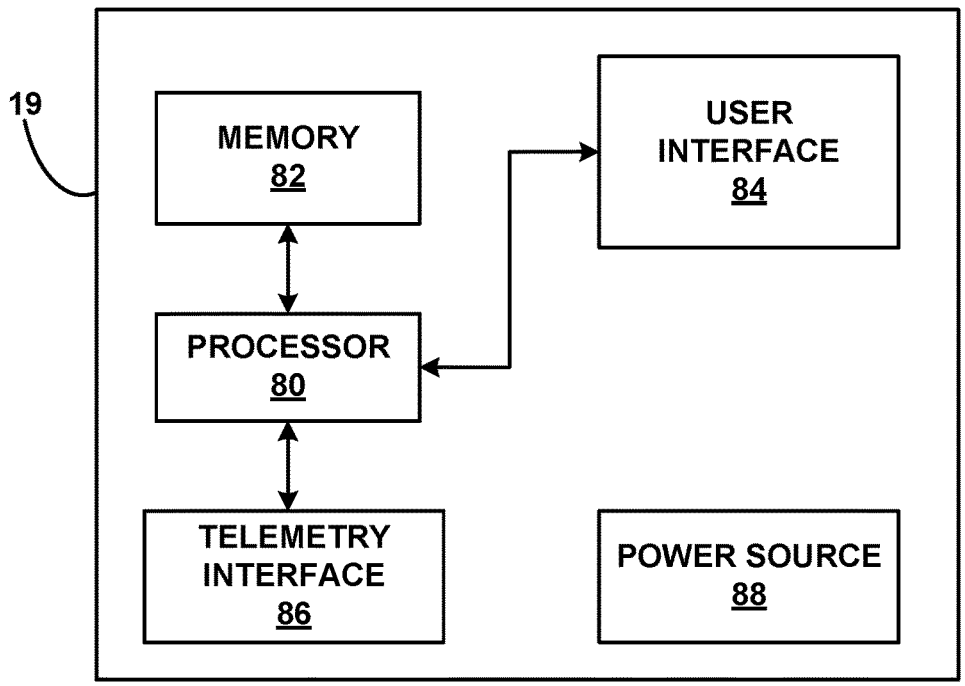
FIG. 3 is a functional block diagram of an example programmer for an implantable medical device.

FIG. 3 is a functional block diagram of an example programmer. As shown in FIG. 3, external programmer 19 includes processor 80, memory 82, user interface 84, telemetry interface 86, and power source 88. Programmer 19 may be used to present anatomical regions to the user via user interface 84, select stimulation programs, generate new stimulation programs with stimulation fields, and transmit the new programs to IMD 20. As described herein, programmer 19 may allow a clinician to define stimulation fields and generate appropriate stimulation parameters. For example, as described herein, processor 80 may store stimulation parameters as one or more programs in memory 82. Processor 80 may send programs to IMD 20 via telemetry interface 86 to control stimulation automatically and/or as directed by the user.

Programmer 19 may be one of a clinician programmer or a patient programmer in some examples, i.e., the programmer may be configured for use depending on the intended user. A clinician programmer may include more functionality than the patient programmer. For example, a clinician programmer may include a more featured user interface, to allow a clinician to download usage and status information from IMD 20, and allow a clinician to control aspects of the IMD not accessible by a patient programmer example of programmer 19.

A user, either a clinician or patient 12, may interact with processor 80 through user interface 84. User interface 84 may include a display, such as a liquid crystal display (LCD), light-emitting diode (LED) display, or other screen, to show information related to stimulation therapy, and buttons or a pad to provide input to programmer 19. Buttons may include an on/off switch, plus and minus buttons to zoom in or out or navigate through options, a select button to pick or store an input, and pointing device, i.e. a mouse, trackball, pointstick or stylus. Other input devices may be a wheel to scroll through options or a touch pad to move a pointing device on the display. In some examples, the display may be a touch screen that enables the user to select options directly from the display screen.

Processor 80 processes instructions from memory 82 and may store user input received through user interface 84 into the memory when appropriate for the current therapy. In addition, processor 80 provides and supports any of the functionality described herein with respect to each example of user interface 84. Processor 80 may comprise any one or more of a microprocessor, digital signal processor (DSP), application specific integrated circuit (ASIC), field-programmable gate array (FPGA), or other digital logic circuitry.

Memory 82 may include instructions for operating user interface 84, telemetry interface 86 and managing power source 88. Memory 82 also includes instructions for generating stimulation fields and stimulation parameters from the stimulation fields. These instructions may include a set of equations needed to characterize brain tissue and interpret stimulation field dimensions. Memory 82 may include any one or more of a random access memory (RAM), read-only memory (ROM), electronically-erasable programmable ROM (EEPROM), flash memory, or the like. Processor 80 may comprise any one or more of a microprocessor, digital signal processor (DSP), application specific integrated circuit (ASIC), field-programmable gate array (FPGA), or other digital logic circuitry.

Memory 82 may store program instructions that, when executed by processor 80, cause the processor and programmer 19 to provide the functionality ascribed to them herein. For example, memory 82 may include a plurality of stimulation templates that are used by processor 80 to create a stimulation template set. Memory 82 may also include instructions for generating stimulation parameters based upon the defined stimulation field. In addition, instructions that allow processor 80 to create electrical field models and activation field models may be stored within memory 82. An atlas or reference anatomical region may also be stored in memory 82 for presentation to the clinician. In some examples, memory 82 does not contain instructions for all functionality for the user interfaces and programming of stimulation parameters as described herein. In this case, memory 82 may only hold the necessary instructions for the specific example that the user desires. Memory 82 may be reformatted with different sets of instructions when needed.

Wireless telemetry in programmer 19 may be accomplished by radio frequency (RF) communication or proximal inductive interaction of programmer 19 with IMD 20. This wireless communication is possible through the use of telemetry interface 86. Accordingly, telemetry interface 86 may include circuitry known in the art for such communication.

Power source 88 delivers operating power to the components of programmer 19. Power source 88 may include a battery and a power generation circuit to produce the operating power. In some examples, the battery may be rechargeable to allow extended operation. Recharging may be accomplished through proximal inductive interaction, or electrical contact with circuitry of a base or recharging station. In other examples, primary batteries may be used.

Figure 4A:
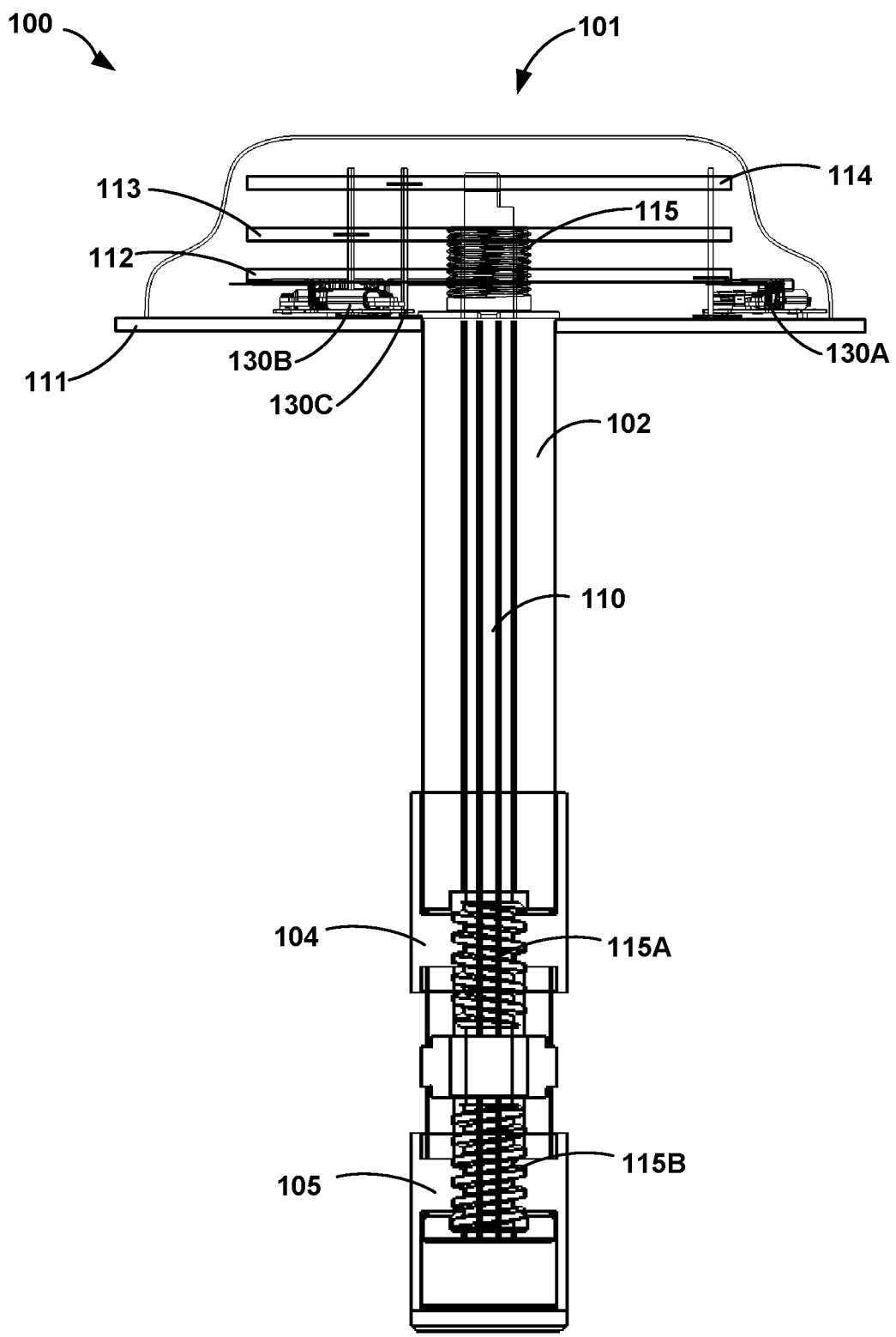
FIGS. 4A-4C illustrate a mechanically adjustable medical lead.
Figure 4B:
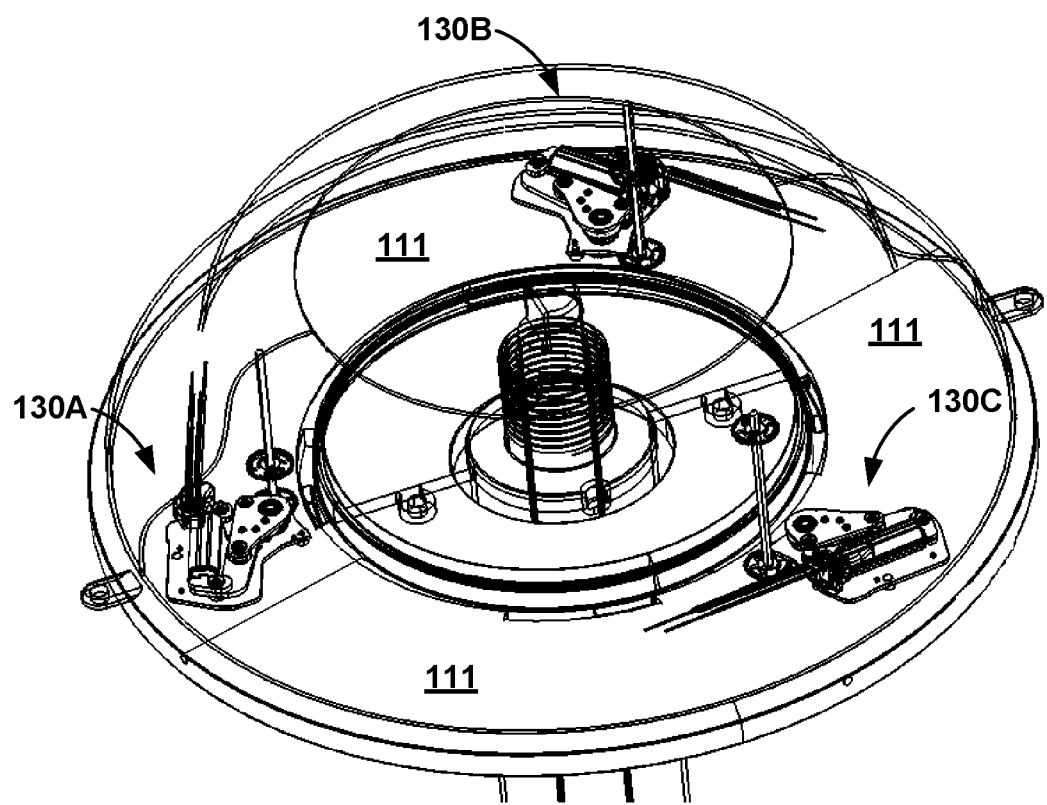
Figure 4C:
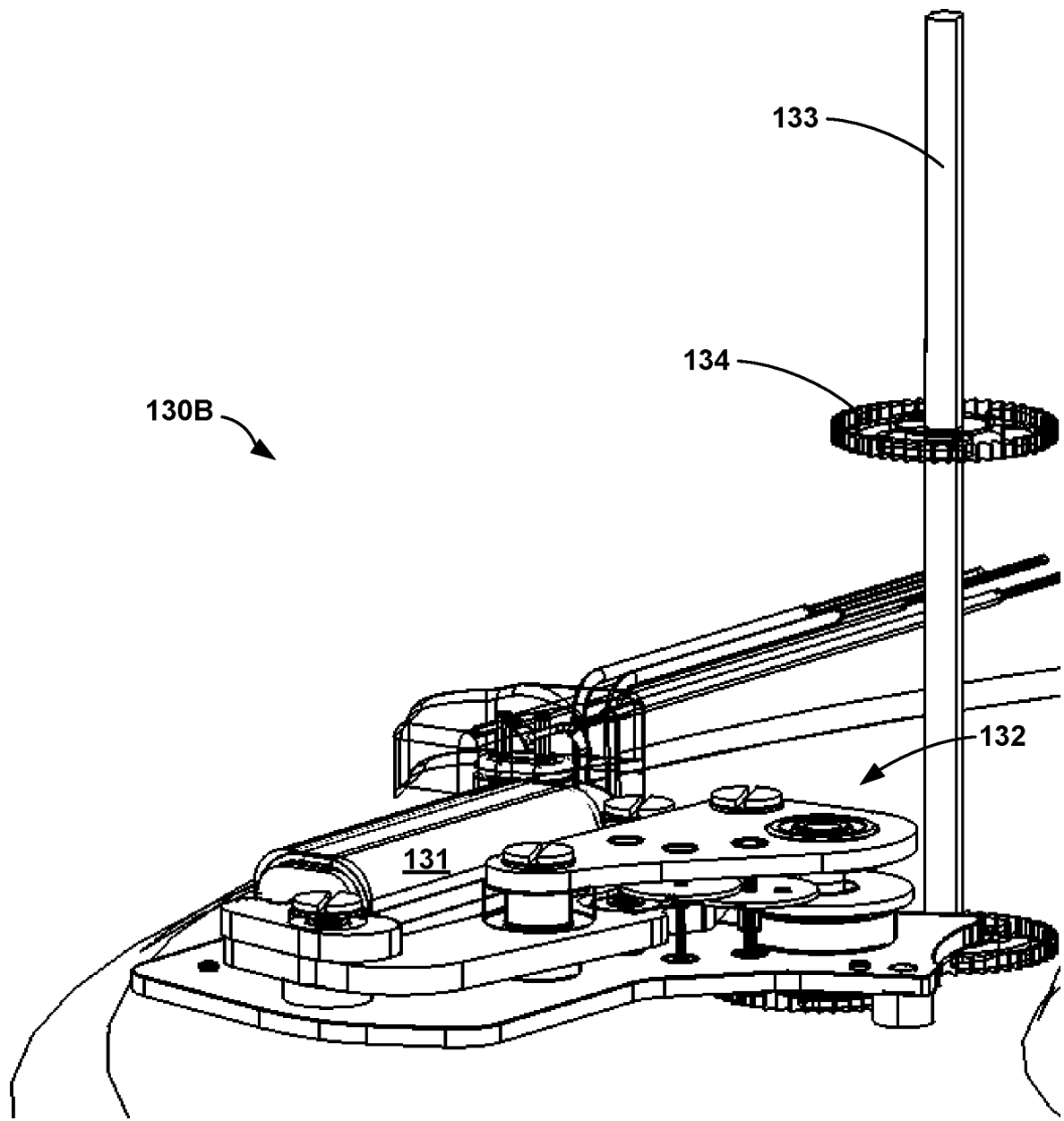

FIGS. 4A-4C illustrate mechanically adjustable medical lead 100, which may be utilized as a DBS lead and may, for example, correspond to mechanically adjustable medical lead 14 of FIG. 1. In particular, FIG. 4A is a cross-sectional view of mechanically adjustable medical lead 100. FIG. 4B is a close-up view of proximal end 101 of mechanically adjustable medical lead 100, and FIG. 4C illustrates motor assembly 130B of mechanically adjustable medical lead 100. In other examples, medical lead 100 may be utilized for other sensing and or simulation of any tissue of a patient, including, but not limited to, spinal cord stimulation and sensing, peripheral nerve stimulation and sensing, pelvic nerve stimulation and sensing, gastric nerve stimulation and sensing, vagal nerve stimulation and sensing, stimulation and sensing of muscles or muscle groups, stimulation and sensing of an organ such as gastric system stimulation and sensing, stimulation and sensing concomitant to gene therapy and others.

Proximal end 101 of medical lead 100 may be coupled to an IMD (for example, IMD 20 of FIG. 1) via one or more conductive wires, such as in a lead extension (not shown). Medical lead 100 includes a medical lead body 102 and electrodes 104 and 105. Medical lead body 102 may have a substantially circular cross-sectional shape, but other shapes may also be used. Medical lead body 102 may be formed from an insulative biocompatible material. Exemplary biocompatible material includes at least one covers of polyurethane, silicone, and fluoropolymers such as tetrafluroethylene (ETFE), polytetrafluroethylene (PTFE), and/or expanded PTFE (i.e. porous ePTFE, nonporous ePTFE). Electrodes 104 and 105 are exposed to tissue of the patient, which allows physiological signals to be sensed from the tissue and/or therapy delivered to the patient.

Electrode 105 is located at a distal portion of medical lead body 102, whereas electrode 104 is located more proximally along medical lead body 102 as compared to electrode 105. As shown in FIG. 4, electrodes 104 and 105 are ring electrodes extending substantially around the entire periphery, for example, circumference, of medical lead 100. In other examples, instead of or in addition to electrodes 104 and 105, medical lead 100 may include segmented electrodes, each including electrode segments extending along an arc less than 360 degrees (for example, 90-120 degrees). Segmented electrodes may be useful for providing an electrical stimulation field that is predominantly focused in a particular transverse direction relative to the longitudinal axis of medical lead 100, and/or targeting a particular stimulation site.

Each of electrodes 104 and 105 can be made from an electrically conductive, biocompatible material, such as platinum iridium. In addition, in some examples, at least one of electrodes 104 and 105 may function as a sensing electrode that monitors internal, physiological, electrical signals of patient 12 (FIG. 1), such as electrical activity of brain 18 (FIG. 1) of patient 12. The configuration, type, and number of electrodes 104 and 105 are merely exemplary. In other examples, medical lead 100 may include any configuration, type, and number of electrodes 104 and 105, and is not limited to the example illustrated in FIG. 4. As examples, stimulation and or sensing function may be provided by biopolar, multipolar or unipolar electrode combinations.

Within medical lead body 102, medical lead 100 also includes insulated electrical conductors 110 coupled to electrodes 104 and 105. Each of conductors 110 is in electrical contact with its respective electrode and extends to a proximal end of lead body 102 to facilitate an electrical connection with an IMD (for example, IMD 20 of FIG. 1). In some examples, conductors 110 are coiled along the length of medical lead body 102 (for example, in a multiconductor coil), but in other examples, conductors 110 may not be coiled. Because each of conductors 110 is electrically coupled to a single one of electrodes 104 and 105, each of electrodes 104 and 105 may be independently activated or used. In other examples, a medical lead including multiple electrodes may include a multiplexer or other switching device such that the medical lead may include fewer conductors than electrodes, while allowing each of the electrodes to be independently activated. The switching device may be responsive to commands from the IMD or an external source to selectively couple the electrodes to the conductors for delivery of stimulation or for sensing. Such a switching device may be particularly suited for use with segmented electrodes.

Medical lead 100 includes three rotatable members 112, 113, 114 positioned adjacent to the proximal end of medical lead body 102. Rotatable members 112, 113, 114 are individually rotatable by separate motor assemblies 130A-130C respectively. For example, rotatable members 112, 113, 114 may be placed under a burr cap covering a hole in the skull of a patient. When part of system 10 (FIG. 1), each of rotatable members 112, 113, 114 is mechanically coupled to and configured to be driven by a rotating output shaft of motor 15 (FIG. 1). In addition, medical lead 100 includes anchor plate 111, which may be fixed to the skull of the patient. As referred to herein, rotation of rotatable members 112, 113, 114 is relative to the fixed position of anchor plate 111.

Rotation of rotatable member 112 changes the radial orientation of electrodes 104, 105 relative to anchor plate 111. Thus, in examples in which electrodes 104, 105 include directional electrodes, the orientation of the simulation or sensing field may be adjusted via rotatable member 112.

Similarly, rotation of rotatable member 114 also moves a position of electrodes 104, 105 to adjust the spacing between the proximal end of medical lead body 102 and electrodes 104, 105. However, rotation of rotatable member 114 directly varies spacing between electrodes 104, 105 via opposing threads 115A and 115B. In particular, electrode 104 is configured to move linearly about lead body 102 during rotation of rotatable member 114 based on interaction with thread 115A as electrode 104 and thread 115A form a threaded joint. Likewise, electrode 105 is configured to move linearly about lead body 102 during rotation of rotatable member 114 based on interaction with thread 115B as electrode 105 and thread 115B form another threaded joint. During rotation of rotatable member 114 electrode 105 will move in the opposite direction about lead body 102 as compared to electrode 104 due to the opposite threading of thread 115B as compared to thread 115A. In this manner, rotation of rotatable member 114 varies the pitch between electrodes 104, 105.

Similarly, rotation of rotatable member 114 also moves a position of electrodes 104, 105 to adjust the spacing between the proximal end of medical lead body 102 and electrodes 104, 105. However, rotation of rotatable member 114 directly varies spacing between electrodes 104, 105 via opposing threads 115A and 115B. In particular, electrode 104 is configured to move linearly about lead body 102 during rotation of rotatable member 114 based on interaction with thread 115A as electrode 104 and thread 115A form a threaded joint. Likewise, electrode 105 is configured to move linearly about lead body 102 during rotation of rotatable member 114 based on interaction with thread 115B as electrode 105 and thread 115B form another threaded joint. During rotation of rotatable member 114 electrode 105 will move in the opposite direction about lead body 102 as compared to electrode 104 due to the opposite threading of thread 115B as compared to thread 115A. In this manner, rotation of rotatable member 114 varies the pitch between electrodes 104, 105.

As mentioned above, FIG. 4C illustrates motor assembly 130B of mechanically adjustable medical lead 100. Motor assembly 130B may be considered representative of motor assemblies 130A and 130C. Motor assembly 130B includes stepper motor 131. Stepper motor 131 is configured to drive geartrain 132 within motor assembly 130B. Output gear 134 is mounted on shaft 133, and is configured to drive rotatable member 113 (not shown in FIG. 4C).

In some examples, motor assembly 130B may further include a sealed housing, stepper motor 131 being within the sealed housing and including a rotating output shaft. The rotating output shaft may be coupled to a mechanical feedthrough, such as one of mechanical feedthroughs 400, 601, 701 or 801. The output of the mechanical feedthrough may be coupled to geartrain 132 to drive rotatable member 113. As discussed with respect to FIG. 10A, the mechanical feedthrough may include a nutating shaft coupled to the rotating output shaft of the motor and within the sealed housing. Alternatively, the mechanical feedthrough may include a pair of coaxial shafts coupled with an offset pin and sealed with a flexible seal including an oscillating cap, as with feedthroughs 601, 701 and 801. Such a mechanical feedthrough may facilitate hermetic sealing of stepper motor 131 and the corresponding motors of motor assemblies 130A and 130C.

In further examples, a medical lead may only provide a single degree of adjustability, for example, either a varying length or a varying pitch such that an engagement mechanism is not required. In any event, the motor may include a stepper motor. The use of a stepper motor combined with fine thread pitch of threaded joints within medical lead 100 may provide precise positioning. As one example, a stepper motor may have a resolution of 7840 steps per revolution. When combined with a 0.050 inch thread-pitch for a threaded joint within medical lead 100, such a combination would provide electrode position adjustment increments of 0.050 inches divided by 7840, or $6.4 \times 10^{-6}$ inches per step. While this particular example is in no way limiting to the scope of this disclosure, it does demonstrate that the precision adjustments facilitated by medical lead 100 may be many orders of magnitude more precise than possible with only surgical positioning of electrodes.

In some examples, the precision of a motor may be verified or improved by including one or more linear sensors to directly sense positioning of one or more of lead body 102 and electrodes 104, 105. In some examples, such linear sensors may include linear variable differential transformer (LVDT) sensors.

Figure 5:
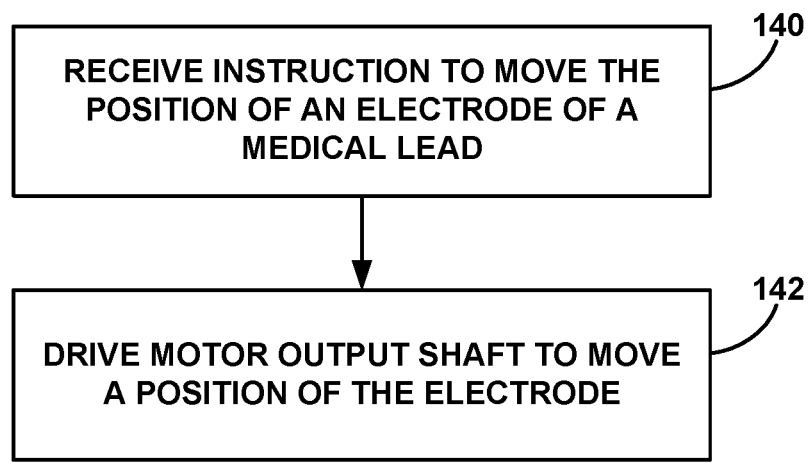
FIG. 5 is a flowchart illustrating an example technique for adjusting the position of an electrode of a mechanically adjustable medical lead implanted within a patient.

FIG. 5 is a flowchart illustrating an example technique for adjusting the position of an electrode of a mechanically adjustable medical lead implanted within a patient. For clarity, the techniques of FIG. 5 are described with respect to system 10, including IMD 20 (FIG. 2) and mechanically adjustable medical lead 100 (FIG. 4).

First, processor 70 of IMD 20 receives an instruction to move the position of one or both of electrodes 104, 105 of medical lead 100 (140). For example, processor 70 of IMD 20 may receive the instruction from a control program stored in memory 72 of IMD 20 or processor 70 of IMD 20 may receive the instruction from programmer 19. In some examples, a clinician may directly instruct processor 70 of IMD 20 to move the position of one or both of electrodes 104, 105 via programmer 19.

Next, processor 70 of IMD 20 operates motor 15 to drive a rotating output shaft of the motor and move a position of one or both of electrodes 104, 105 of medical lead 100 (142). For example, processor 70 may operate motor 15 to drive rotatable member 112 to move a position of electrodes 104, 105 to adjust the spacing between the proximal end of medical lead body 102 and electrodes 104, 105 by varying an overall length of medical lead 100. Alternatively or in addition, processor 70 may operate motor 15 to drive rotatable member 114 to move a position of electrodes 104, 105 to directly vary spacing between electrodes 104, 105 via opposing threads 115A and 115B. In this manner, IMD 20 and processor 70 are suitable for implementing electrode positioning adjustments facilitated by mechanically adjustable medical lead 100.

Figure 6:
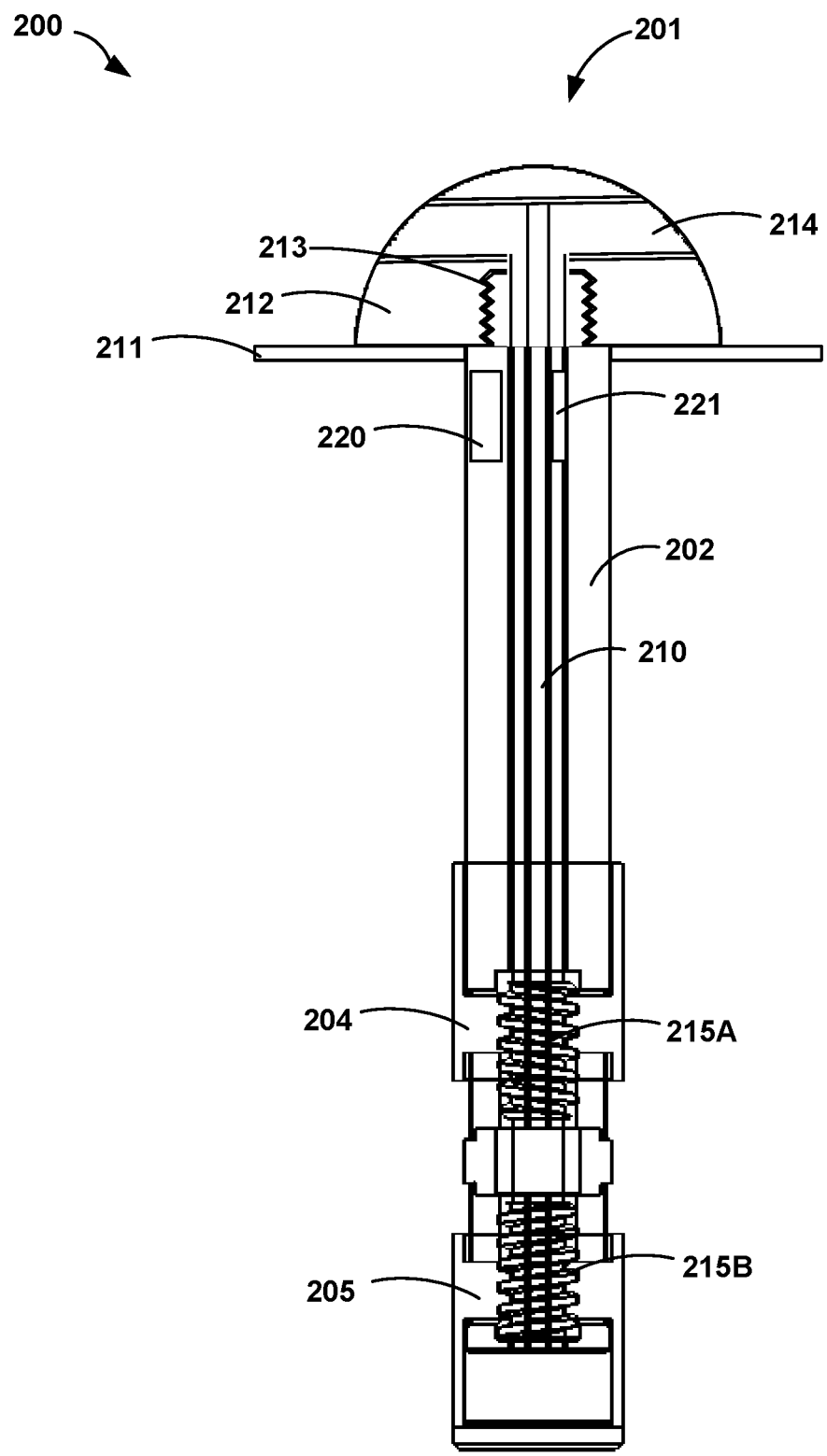
FIG. 6 is a cross-sectional view of a mechanically adjustable medical lead including a force sensor configured to measure a resistance to movement of a position of an electrode of the medical lead.

FIG. 6 is a cross-sectional view of mechanically adjustable medical lead 200. Medical lead 200 includes force sensors 220, 221, which are each configured to measure a resistance to movement of a position of an electrode of the medical lead. Medical lead 200 may be utilized as a DBS lead and may, for example, correspond to mechanically adjustable medical lead 14 of FIG. 1. In other examples, medical lead 200 may be utilized for other sensing and or simulation of any tissue of a patient, including, but not limited to, spinal cord stimulation and sensing, peripheral nerve stimulation and sensing, pelvic nerve stimulation and sensing, gastric nerve stimulation and sensing, vagal nerve stimulation and sensing, stimulation and sensing of muscles or muscle groups, stimulation and sensing of an organ such as gastric system stimulation and sensing, stimulation and sensing concomitant to gene therapy and others.

Proximal end 201 of medical lead 200 may be coupled to an IMD (for example, IMD 20 of FIG. 1) via one or more conductive wires, such as in a lead extension (not shown). Medical lead 200 includes a medical lead body 202 and electrodes 204 and 205. Medical lead body 202 may have a substantially circular cross-sectional shape, but other shapes may also be used. Medical lead body 202 may be formed from an insulative biocompatible material.

Electrode 205 is located at a distal portion of medical lead body 202, whereas electrode 204 is located more proximally along medical lead body 202 as compared to electrode 205. As shown in FIG. 6, electrodes 204 and 205 are ring electrodes extending substantially around the entire periphery, for example, circumference, of medical lead 200. In other examples, instead of or in addition to electrodes 204 and 205, medical lead 200 may include segmented electrodes, each including electrode segments extending along an arc less than 360 degrees (for example, 90-120 degrees).

Each of electrodes 204 and 205 can be made from an electrically conductive, biocompatible material, such as platinum iridium. In addition, in some examples, at least one of electrodes 204 and 205 may function as a sensing electrode that monitors internal, physiological, electrical signals of patient 12 (FIG. 1), such as electrical activity of brain 18 (FIG. 1) of patient 12. The configuration, type, and number of electrodes 204 and 205 are merely exemplary. In other examples, medical lead 200 may include any configuration, type, and number of electrodes 204 and 205, and is not limited to the example illustrated in FIG. 6.

Within medical lead body 202, medical lead 200 also includes insulated electrical conductors 210 coupled to electrodes 204 and 205. Conductors 210 are in electrical contact with their respective electrode and extend to a proximal end of lead body 202 to facilitate an electrical connection with an IMD (for example, IMD 20 of FIG. 1). In some examples, conductors 210 are coiled along the length of medical lead body 202 (for example, in a multi-conductor coil), but in other examples, conductors 210 may not be coiled. Because each of conductors 210 is electrically coupled to a single one of electrodes 204 and 205, each of electrodes 204 and 205 may be independently activated. In other examples, a medical lead including multiple electrodes may include a multiplexer or other switching device such that the medical lead may include fewer conductors than electrodes, while allowing each of the electrodes to be independently activated. The switching device may be responsive to commands from the IMD or an external source to selectively couple the electrodes to the conductors for delivery of stimulation or for sensing. Such a switching device may be particularly suited for use with segmented electrodes.

Medical lead 200 includes two rotatable members 212, 214 positioned adjacent to the proximal end of medical lead body 202. For example, rotatable members 212, 214 may be placed under a burr cap covering a hole in the skull of a patient. When part of system 10 (FIG. 1), each of rotatable members 212, 214 is mechanically coupled to and configured to be driven by a rotating output shaft of motor 15 relative to anchor plate 211, which may be fixed to the skull of the patient. Rotation of rotatable member 212 moves a position of electrodes 204, 205 to adjust the spacing between the proximal end of medical lead body 202 and electrodes 204, 205 by varying an overall length of medical lead. In particular, rotatable member 212 and lead body 202 combine to form threaded joint 213. Threaded joint 213 transfers the rotation of rotatable member 212 into substantially linear movement to move the positions of electrodes 204, 205 and vary an overall length of medical lead 200.

Medical lead 200 further includes force sensor 220, which is configured to measure a resistance to movement of the position of electrodes 204, 205 by varying the overall length of medical lead 200. As force sensor 220 is located between threaded joint 213 and electrodes 204, 205, force sensor 220 may be configured to measure tensile strain on lead body 202. In one example, force sensor 220 includes a piezoelectric sensor mounted to an interior or exterior surface of lead body 202 or within lead body 202. In the same or different examples, medical lead 200 may include a current sensor and force may be measured by monitoring current required to operate a motor used to drive rotatable member 212, for example, current through motor 15 (FIG. 1). Force sensor 220 is further configured to deliver a force signal based on the resistance to movement to a processor, such as processor 70 of IMD 20 (FIG. 2). The processor may control the motor used to drive rotatable member 212 based on the force signal. In one example, the processor may control the motor used to drive rotatable member 212 at least in part by limiting movement to prevent the resistance to movement as detected by force sensor 220 from exceeding a predefined value.

Similarly, rotation of rotatable member 214 also moves a position of electrodes 204, 205 to adjust the spacing between the proximal end of medical lead body 202 and electrodes 204, 205. However, rotation of rotatable member 214 directly varies spacing between electrodes 204, 205 via opposing threads 215A and 215B. In particular, electrode 204 is configured to move linearly about lead body 202 during rotation of rotatable member 214 based on interaction with thread 215A as electrode 204 and thread 215A form a threaded joint. Likewise, electrode 205 is configured to move linearly about lead body 202 based during rotation of rotatable member 214 based on interaction with thread 215B as electrode 205 and thread 215B form another threaded joint. Due to the opposite threading of thread 215B as compared to thread 215A, electrode 205 will move in the opposite direction about lead body 202 as compared to electrode 204 due to rotation of rotatable member 214. In this manner, rotation of rotatable member 214 varies the pitch between electrodes 204, 205.

Medical lead 200 further includes force sensor 221, which is configured to measure a resistance to movement of the position of electrodes 204, 205 by varying the pitch between electrodes 204, 205. As force sensor 221 is located between the motor and the threaded joints of threads 215A, 215B and electrodes 204, 205, force sensor 221 may be configured to measure rotational strain on rotatable member 214. In one example, force sensor 221 includes a piezoelectric sensor. In the same or different examples, medical lead 200 may include a current sensor and force may be measured by monitoring current required to operate a motor used to drive rotatable member 214, for example, current through motor 15 (FIG. 1). Force sensor 221 is further configured to deliver a force signal based on the resistance to movement to a processor, such as processor 70 of IMD 20 (FIG. 2). The processor may control the motor used to drive rotatable member 214 based on the force signal. In one example, the processor may control the motor used to drive rotatable member 214 at least in part by limiting movement to prevent the resistance to movement as detected by force sensor 221 from exceeding a predefined value.

In some examples, medical lead 200 may further include a motor, such as motor 15 (FIG. 1) and optionally an engagement mechanism (not shown), such as a mechanical or magnetic clutch mechanism to selectively drive one or both of rotatable members 212, 214. In other examples, medical lead 200 may include a separate drive motor for each of rotatable members 212, 214. In further examples, a medical lead may only provide a single degree of adjustability, for example, either a varying length or a varying pitch such that an engagement mechanism is not required. In any event, the motor may include a stepper motor. The use of a stepper motor combined with fine thread pitch of threaded joints within medical lead 200 may provide precise positioning. In some examples, the precision of a motor may be verified or improved by including one or more linear sensors to directly sense positioning of one or more of lead body 202 and electrodes 204, 205. In some examples, such linear sensors may include linear variable differential transformer (LVDT) sensors.

In the same or different examples, medical lead 200 may also further include a sealed housing, the motor being within the sealed housing and including a rotating output shaft. The rotating output shaft may be coupled to a mechanical feedthrough, such as one of mechanical feedthroughs 400, 601, 701 or 801. As discussed with respect to FIG. 10A, the mechanical feedthrough may include a nutating shaft coupled to the rotating output shaft of the motor and within the sealed housing. Alternatively, the mechanical feedthrough may include a pair of coaxial shafts coupled with an offset pin and sealed with a flexible seal including an oscillating cap, as with feedthroughs 601, 701 and 801. Such a mechanical feedthrough may facilitate hermetic sealing of the motor.

Figure 7:
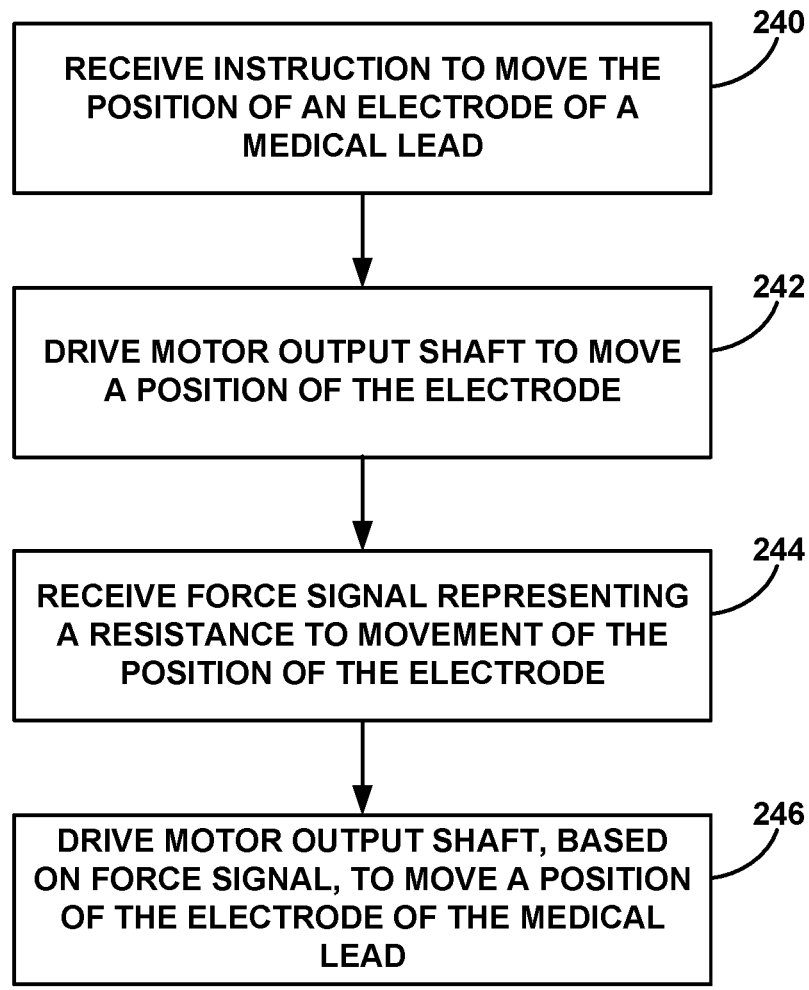
FIG. 7 is a flowchart illustrating an example technique for adjusting the position of an electrode of a mechanically adjustable medical lead implanted within a patient based on a signal from a force sensor.

FIG. 7 is a flowchart illustrating an example technique for adjusting the position of an electrode of a mechanically adjustable medical lead implanted within a patient based on a signal from a force sensor. For clarity, the techniques of FIG. 7 are described with respect to system 10, including IMD 20 (FIG. 2) and mechanically adjustable medical lead 200 (FIG. 6).

First, processor 70 of IMD 20 receives an instruction to move the position of one or both of electrodes 204, 205 of medical lead 200 (240). For example, processor 70 of IMD 20 may receive the instruction from a control program stored in memory 72 of IMD 20 or processor 70 of IMD 20 may receive the instruction from programmer 19. In some examples, a clinician may directly instruct processor 70 of IMD 20 to move the position of one or both of electrodes 204, 205 via programmer 19. S Next, processor 70 of IMD 20 operates motor 15 to drive a rotating output shaft of the motor and move a position of one or both of electrodes 204, 205 of medical lead 200 (242). For example, processor 70 may operate motor 15 to drive rotatable member 212 to move a position of electrodes 204, 205 to adjust the spacing between the proximal end of medical lead body 202 and electrodes 204, 205 by varying an overall length of medical lead 200. Alternatively or in addition, processor 70 may operate motor 15 to drive rotatable member 214 to move a position of electrodes 204, 205 to directly vary spacing between electrodes 204, 205 via opposing threads 215A and 215B.

Prior to, during, and/or following the operation of motor 15 to drive a rotating output shaft of the motor and move a position of one or both of electrodes 204, 205 of medical lead 200, processor 70 receiving a force signal from one or both of force sensors 220, 221 (244). The force signal represents a resistance to movement of the position of the corresponding electrodes of medical lead 200. For example, the force signal from force sensor 220 represents a resistance to varying the overall length of lead 200, whereas the force signal from force sensor 220 represents a resistance to varying the spacing between electrodes 204, 205.

Processor 70 then operates, based on the force signal, as well as the instruction to move the position of one or both of electrodes 204, 205, motor 15 to drive one or both of rotatable members 212, 214 via a rotating output shaft of motor 15, thereby moving a position of at least one of electrodes 204, 205 to adjust a spacing between a proximal end of medical lead 200 and at least one of electrodes 204, 205 (246). In one example, processor 70 may operate motor 15 to limit the movement to prevent resistance to the movement from exceeding a predefined value. In this manner, IMD 20 and processor 70 are suitable for implementing electrode positioning adjustments facilitated by mechanically adjustable medical lead 200.

Figure 8A:
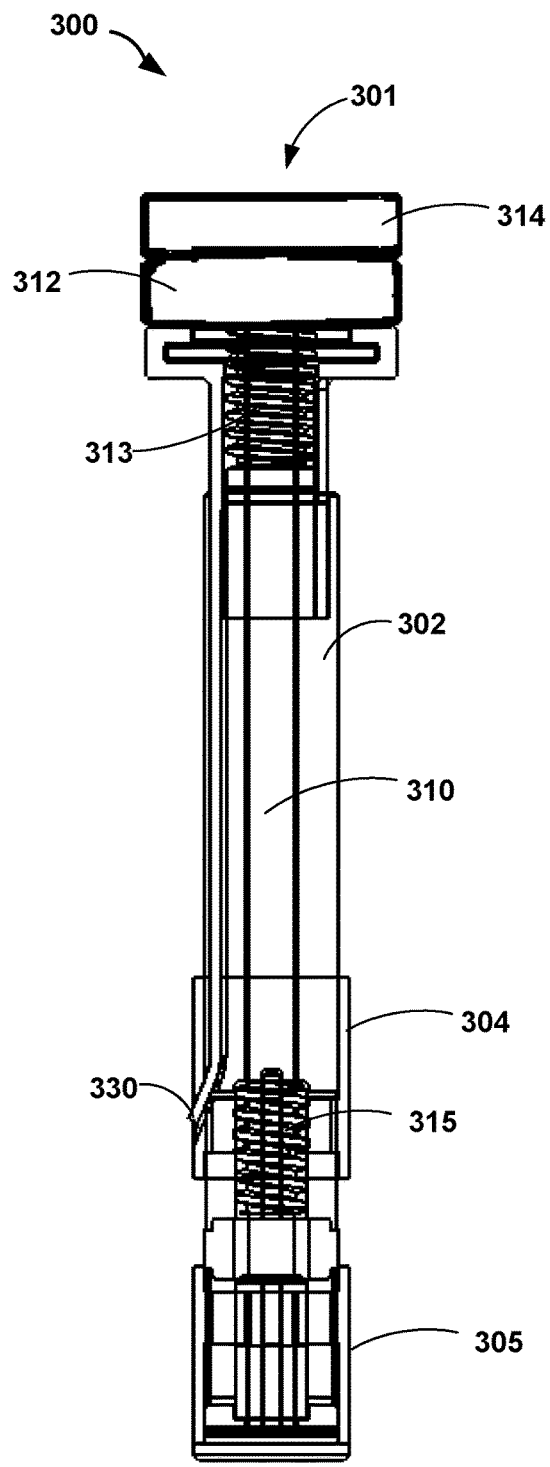
FIGS. 8A and 8B illustrate cross-sectional views of a mechanically adjustable medical lead including a retractable electrode.
Figure 8B:
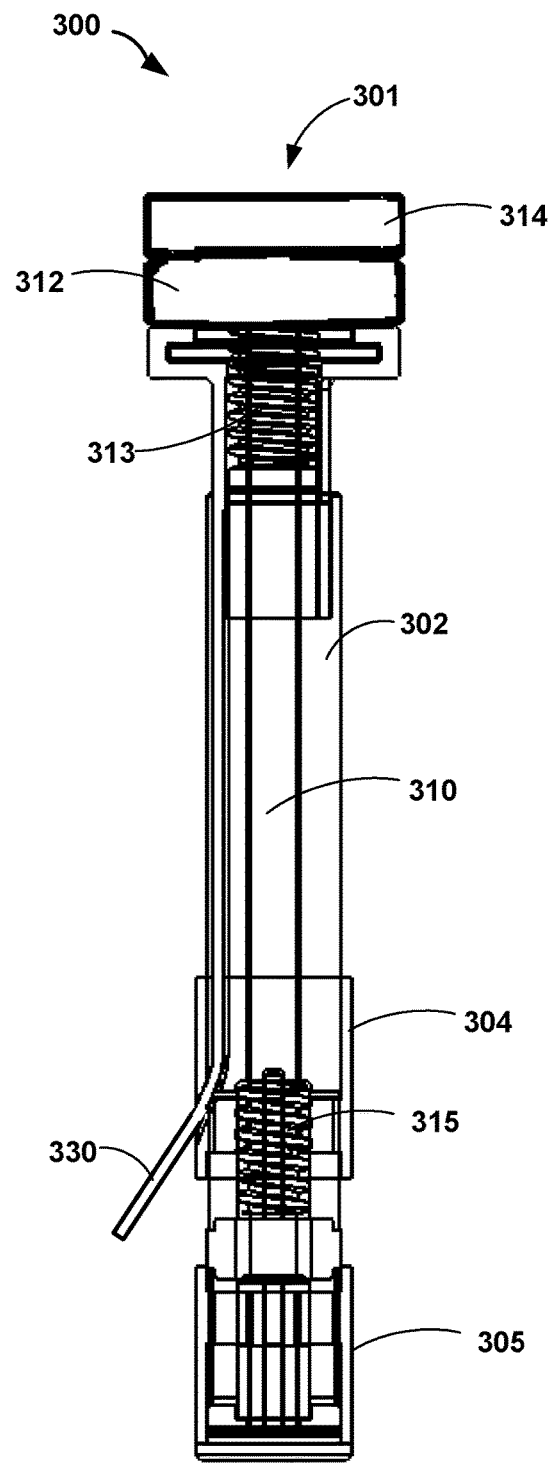

FIGS. 8A-8B illustrate cross-sectional views of mechanically adjustable medical lead 300, which includes retractable electrode 330. In particular, FIG. 8A illustrates medical lead 300 with retractable electrode 330 in a fully retracted position such that it is substantially within the profile of lead body 302, whereas FIG. 8B illustrates medical lead 300 with retractable electrode 330 in an extended position beyond the profile of lead body 302. Medical lead 300 may be utilized as a DBS lead and may, for example, correspond to mechanically adjustable medical lead 14 of FIG. 1. In other examples, medical lead 300 may be utilized for other sensing and or simulation of any tissue of a patient, including, but not limited to, spinal cord stimulation and sensing, peripheral nerve stimulation and sensing, pelvic nerve stimulation and sensing, gastric nerve stimulation and sensing, vagal nerve stimulation and sensing, stimulation and sensing of muscles or muscle groups, stimulation and sensing of an organ such as gastric system stimulation and sensing, stimulation and sensing concomitant to gene therapy and others.

Proximal end 301 of medical lead 300 may be coupled to an IMD (for example, IMD 20 of FIG. 1) via one or more conductive wires, such as in a lead extension (not shown). Medical lead 300 includes a medical lead body 302, electrodes 304 and 305 as well as retractable electrode 330. Medical lead body 302 may have a substantially circular cross-sectional shape, but other shapes may also be used. Medical lead body 302 may be formed from an insulative biocompatible material.

Electrode 305 is located at a distal portion of medical lead body 302, whereas electrode 304 is located more proximally along medical lead body 302 as compared to electrode 305. Electrodes 304 and 305 are ring electrodes extending substantially around the entire periphery, for example, circumference, of medical lead 300. In other examples, instead of or in addition to electrodes 304 and 305, medical lead 300 may include segmented electrodes, each including electrode segments extending along an arc less than 360 degrees (for example, 90-120 degrees). In addition, retractable electrode 330 is located more proximally along medical lead body 302 as compared to electrode 305, although with other designs one or more retractable electrode may be located at any point along medical lead body 302.

Each of electrodes 304, 305 and 330 can be made from an electrically conductive, biocompatible material, such as platinum iridium. In addition, in some examples, at least one of electrodes 304, 305 and 330 may function as a sensing electrode that monitors internal, physiological, electrical signals of patient 12 (FIG. 1), such as electrical activity of brain 18 (FIG. 1) of patient 12. The configuration, type, and number of electrodes 304, 305 and 330 are merely exemplary. In other examples, medical lead 300 may include any configuration, type, and number of electrodes 304, 305 and 330, and is not limited to the example illustrated in FIGS. 8A-8B.

Within medical lead body 302, medical lead 300 also includes insulated electrical conductors 310 coupled to electrodes 304 and 305. Conductors 310 are in electrical contact with their respective electrode and extend to a proximal end of lead body 302 to facilitate an electrical connection with an IMD (for example, IMD 20 of FIG. 1). In addition, the conductor of electrode 330 also extends to a proximal end of lead body 302 to facilitate an electrical connection with an IMD. In other examples, electrode 330 may be electrically coupled to the conductor of one of electrodes 304 or 305. In some examples, conductors 310 are coiled along the length of medical lead body 302 (for example, in a multiconductor coil), but in other examples, conductors 310 may not be coiled. Because each of conductors 310 is electrically coupled to a single one of electrodes 304 and 305, each of electrodes 304, 305 and 330 may be independently activated. In other examples, a medical lead including multiple electrodes may include a multiplexer or other switching device such that the medical lead may include fewer conductors than electrodes, while allowing each of the electrodes to be independently activated. The switching device may be responsive to commands from the IMD or an external source to selectively couple the electrodes to the conductors for delivery of stimulation or for sensing. Such a switching device may be particularly suited for use with segmented electrodes.

Medical lead 300 includes two rotatable members 312, 314 positioned adjacent to the proximal end of medical lead body 302. For example, rotatable members 312, 314 may be placed under a burr cap covering a hole in the skull of a patient. When part of system 10 (FIG. 1), each of rotatable members 312, 314 are mechanically coupled to and configured to be driven by a rotating output shaft of motor 15. Rotation of rotatable member 312 moves a position of retractable electrode 330 to selectively deploy and retract the retractable electrode 330 from medical lead body 302. Rotatable member 312 forms threaded joint 313, which transfers the rotation of rotatable member 312 into substantially linear movement to selectively deploy and retract the retractable electrode 330 from medical lead body 302.

Similarly, rotation of rotatable member 314 also moves a position of electrode 304 to adjust the spacing between the proximal end of medical lead body 302 and electrode 304 via threaded joint 315 formed between rotatable member 314 and electrode 304. Rotation of rotatable member 314 also varies spacing between electrodes 304, 305, as electrode 305 remain stationary during rotation of rotatable member 314. In particular, electrode 304 is configured to move linearly about lead body 302 during rotation of rotatable member 314 based on interaction with thread 315. In this manner, rotation of rotatable member 314 varies the pitch between electrodes 304, 305.

In some examples, medical lead 300 may further include a rotatable member and a threaded joint configured to vary an overall length of medical lead 300, as with rotatable member 112 and the threaded joint of medical lead 100 (FIG. 4).

In some examples, medical lead 300 may further include a motor, such as motor 15 (FIG. 1) and optionally an engagement mechanism (not shown), such as a mechanical or magnetic clutch mechanism to selectively drive one or both of rotatable members 312, 314. In other examples, medical lead 300 may include a separate drive motor for each of rotatable members 312, 314. In further examples, a medical lead may only provide a single degree of adjustability, for example, either a retractable electrode or a varying pitch such that an engagement mechanism is not required. In any event, the motor may include a stepper motor. The use of a stepper motor combined with fine thread pitch of threaded joints within medical lead 300 may provide precise positioning. In some examples, the precision of a motor may be verified or improved by including one or more linear sensors to directly sense positioning of one or more of lead body 302 and electrodes 304, 305. In some examples, such linear sensors may include linear variable differential transformer (LVDT) sensors.

In the same or different examples, medical lead 300 may also further include a sealed housing, the motor being within the sealed housing and including a rotating output shaft. The rotating output shaft may be coupled to a mechanical feedthrough, such as one of mechanical feedthroughs 400, 601, 701 or 801. As discussed with respect to FIG. 10A, the mechanical feedthrough may include a nutating shaft coupled to the rotating output shaft of the motor and within the sealed housing. Alternatively, the mechanical feedthrough may include a pair of coaxial shafts coupled with an offset pin and sealed with a flexible seal including an oscillating cap, as with feedthroughs 601, 701 and 801. Such a mechanical feedthrough may facilitate hermetic sealing of the motor.

Figure 9:
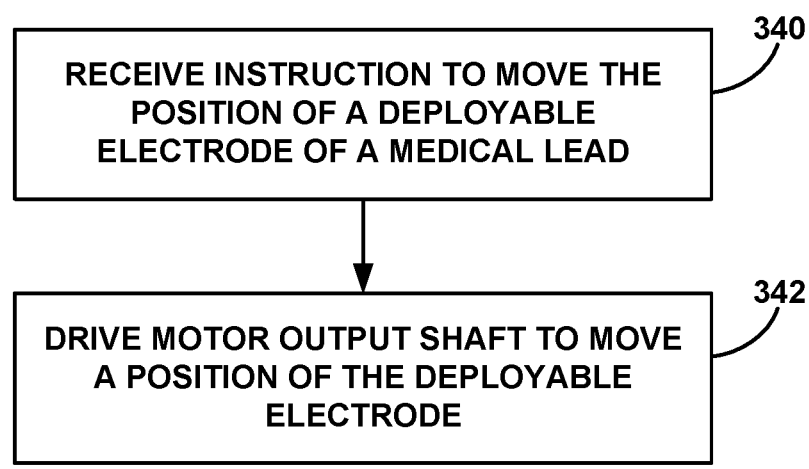
FIG. 9 is a flowchart illustrating an example technique for deploying a retractable electrode of a mechanically adjustable medical lead implanted within a patient.

FIG. 9 is a flowchart illustrating an example technique for deploying a retractable electrode of a mechanically adjustable medical lead implanted within a patient. For clarity, the techniques of FIG. 9 are described with respect to system 10, including IMD 20 (FIG. 2) and mechanically adjustable medical lead 300 (FIGS. 8A-8B).

First, processor 70 of IMD 20 receives an instruction to deploy retractable electrode 330 of medical lead 300 (340). For example, processor 70 of IMD 20 may receive the instruction from a control program stored in memory 72 of IMD 20 or processor 70 of IMD 20 may receive the instruction from programmer 19. In some examples, a clinician may directly instruct processor 70 of IMD 20 to move the position of one or both of electrodes 304, 330 via programmer 19.

Next, processor 70 of IMD 20 operates motor 15 to drive a rotating output shaft of the motor to rotate rotatable member 312 and to deploy retractable electrode 330 of medical lead 300 (342). Processor 70 of IMD 20 may also operate motor 15 to drive a rotating output shaft of the motor to rotate rotatable member 312 in an opposing direction to retract retractable electrode 330 of medical lead 300. In addition, processor 70 may operate motor 15 to drive rotatable member 314 to move a position of electrode 304 to directly vary spacing between electrodes 304, 305. In some examples, processor 70 may receive force signals from force sensors monitoring resistance to movement of electrodes driven by one or both of rotatable members 312, 314 and may operate motor 15 to drive the corresponding rotatable members 312, 314 based on the force signals. For example, processor 70 may limit movement of retractable electrode 330 to prevent resistance to the movement of limiting movement of the retractable electrode to prevent resistance to the movement of the retractable electrode from exceeding a predefined value. In this manner, IMD 20 and processor 70 are suitable for implementing electrode positioning adjustments facilitated by mechanically adjustable medical lead 300.

Figure 10A:
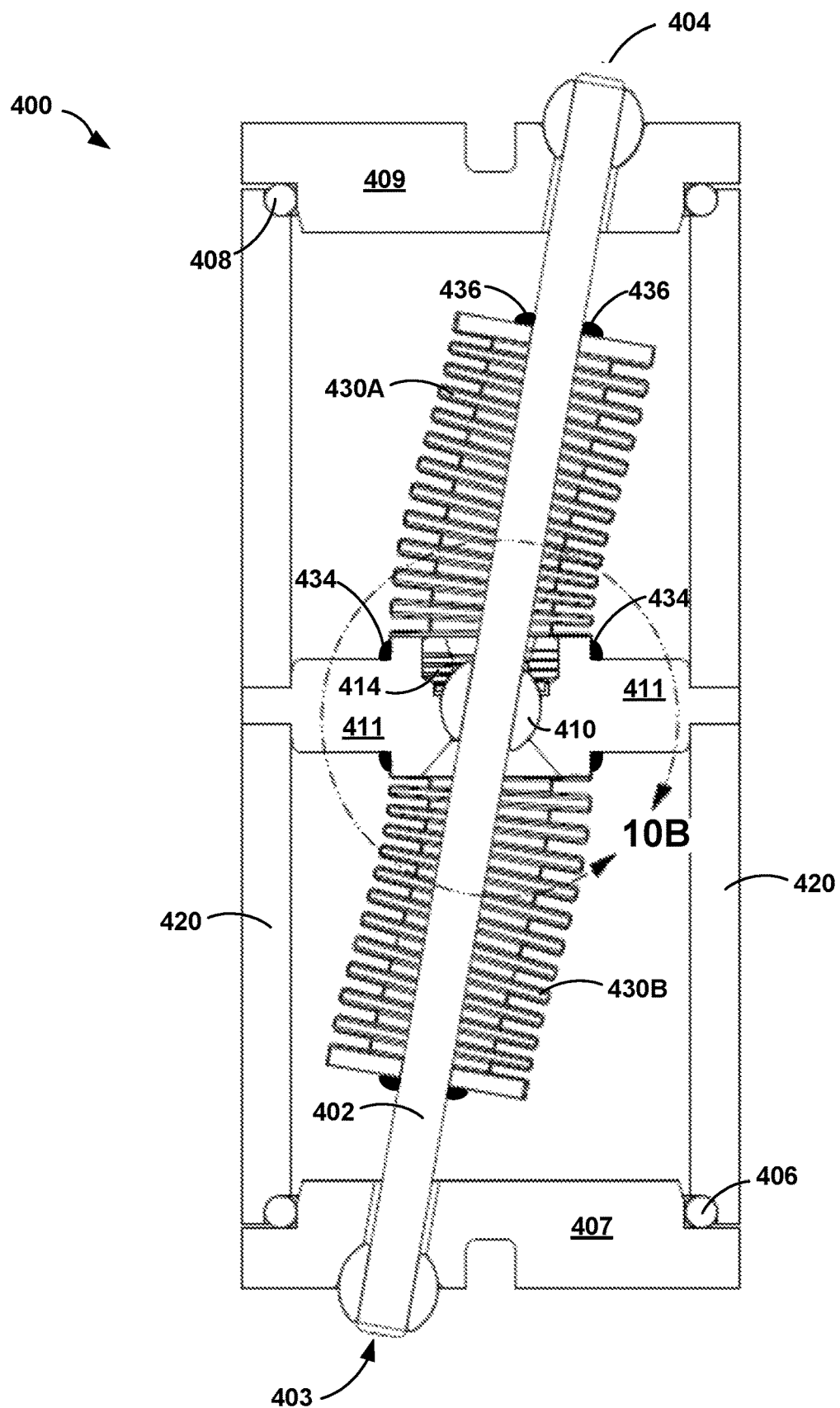
FIGS. 10A-10D illustrate components of a nutating mechanical feedthrough that facilitates mechanical coupling to a rotating shaft within a hermetically sealed enclosure.

FIGS. 10A-10D illustrate components of a nutating mechanical feedthrough that facilitates mechanical coupling to a rotating shaft within a hermetically sealed enclosure. FIG. 10A is a cross-sectional view of a nutating mechanical feedthrough 400. Nutating mechanical feedthrough 400 facilitates mechanical coupling to a rotating shaft within a hermetically sealed enclosure. For example, nutating mechanical feedthrough 400 may be suitable for connecting any of medical leads, 100, 200 and 300 to motor 15.

Nutating mechanical feedthrough 400 includes an oscillating component, in this example, nutating shaft 402, which is supported by three separate bearings. A central portion of nutating shaft 402 is supported by central bearing 410. Central bearing 410 allows nutating shaft 402 to pivot relative to center plate 411. In some examples, central bearing 410 may include a radial spherical bearing. Proximal end 403 of nutating shaft 402 is supported by radial ball bearing 406 via plate 407. Similarly, distal end 404 of nutating shaft 402 is supported by radial ball bearing 408 via plate 409. Whereas plates 407, 409 rotate, nutating shaft 402 does not substantially rotate but only nutates. However, even though nutating shaft 402 does not rotate, nutating shaft 402 rotationally couples plates 407, 409 to one another. In this manner, the rotational motion of one of plates 407, 409 is transferred to the other of plates 407, 409 via nutating shaft 402.

Because nutating shaft 402 does not rotate, nutating shaft 402 facilitates hermetic sealing to isolate plates 407, 409 from one another. In the example of nutating mechanical feedthrough 400, the hermetic boundary between rotating plates 407, 409 includes housing 420, center plate 411 and flexible seals 430A, 430B. Flexible seals 430A, 430B provide a double hermetic barrier for nutating mechanical feedthrough 400. By design, the flexible seals 430A, 430B flex and may be subject to failure from cycling fatigue, such that the redundancy offered by additional barriers may improve the reliability of the hermetic sealing as compared to a design with a single flexible seal. In other examples, only a one of flexible seals 430A, 430B may be used to provide a single hermetic barrier within a nutating mechanical feedthrough. A proximal side of flexible seal 430A covers a distal side of central bearing 410, and a distal side of flexible seal 430A is secured to a distal portion of the nutating shaft 402 located distally relative to central bearing 410. Conversely, a distal side of flexible seal 430B covers a proximal side of central bearing 410, and a proximal side of flexible seal 430B is secured to a proximal portion of the nutating shaft 402 located proximally relative to central bearing 410.

In some examples, flexible seals 430A, 430B each include a metal bellows, such as an electroformed metal bellows. The metal bellows may include alternating layers of copper and nickel. In some examples, electroforming such a metal bellows may include plating the alternating layers of copper and nickel on an aluminum mandrel before dissolving the aluminum mandrel with an acid to leave the metal bellows behind. The design of nutating mechanical feedthrough 400 and the metal bellows in particular may be selected to limit the operating stress on the metal bellows during the nutating motion of nutating shaft 402. In one example, the metal bellows may be subjected to an operating stress of less than forty percent of its yield stress. In another example, the metal bellows may be subjected to an operating stress of no more than twenty percent of its yield stress. Limiting the operating stress of the metal bellows to the smallest possible percentage of its yield stress facilitates forming a reliable hermetic boundary with the metal bellows. Limiting the operating stress may increase the service life of the metal bellows.

Figure 11:
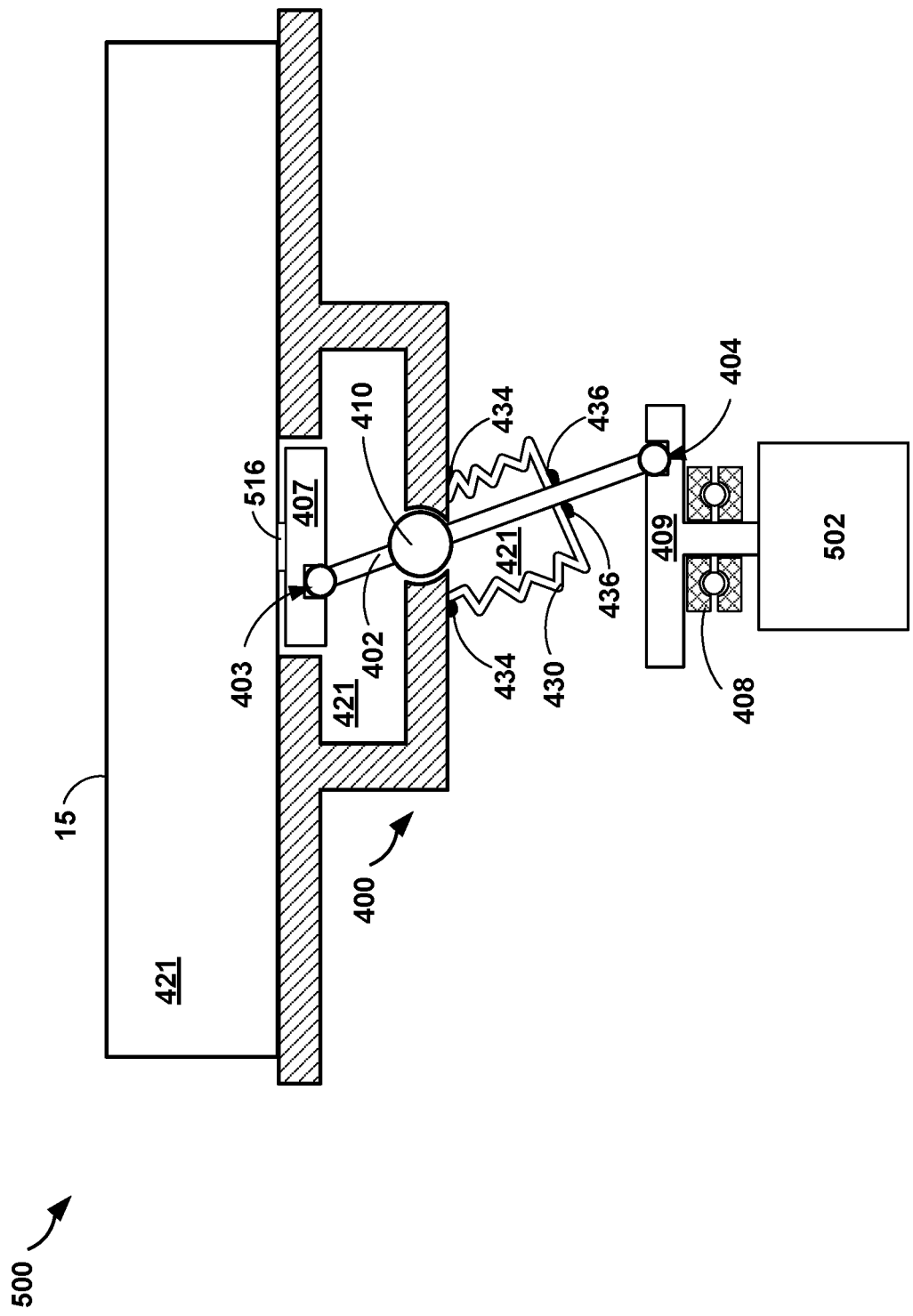
FIG. 11 is a conceptual diagram of an assembly including a motor within a hermetically sealed enclosure and a nutating mechanical feedthrough that facilitates mechanical coupling to a rotating shaft of the motor.

Nutating mechanical feedthrough 400 further includes weld joint 434, which seals an interface of flexible seal 430A and housing 420 and includes weld joint 436, which seals an interface of flexible seal 430A and nutating shaft 402. In this manner, housing 420, center plate 411, flexible seal 430A, and weld joints 434, 436 combine to form a hermetic boundary between plates 407, 409 to contain hermetically sealed enclosure 421. Weld joints 434, 436 may be considered representative of weld joints for flexible seals 340A, 430B, and additional weld joints for flexible seal 430B are not illustrated. The interface between center plate 411 and housing 420 may also include weld joints to insure hermetic sealing. Note that plate 407 should be considered to be entirely within hermetically sealed enclosure 421 and the remaining boundaries of hermetically sealed enclosure 421 are not illustrated in FIG. 10A. As an example, a motor driving plate 407 may have a sealed housing, and the sealed motor housing may be sealed to housing 420 to form the entire boundary of hermetically sealed enclosure 421, for example, as illustrated in the example of FIG. 11.

In some examples, hermetically sealed enclosure 421 may be filled with a selected fluid, such as an inert gas, oil or other liquid. Hermetically sealed enclosure 421 may further provide one or more of the additional design options for an implantable medical device. Hermetically sealed enclosure 421 may enable the option of removing traditional electrical feedthroughs from neurostimulation system designs employing rotary prime movers. Hermetically sealed enclosure 421 may further facilitate placing both ends of an electrical feedthrough in a dry operating environment. Hermetically sealed enclosure 421 may further allow critical mechanical components of an implantable medical device, not just motors and other electrical components, to be sealed within. In addition, hermetically sealed enclosure 421 may remediate corrosion and dendritic growth issues by depriving these processes of the chemical fuel required to sustain them.

Figure 10B:
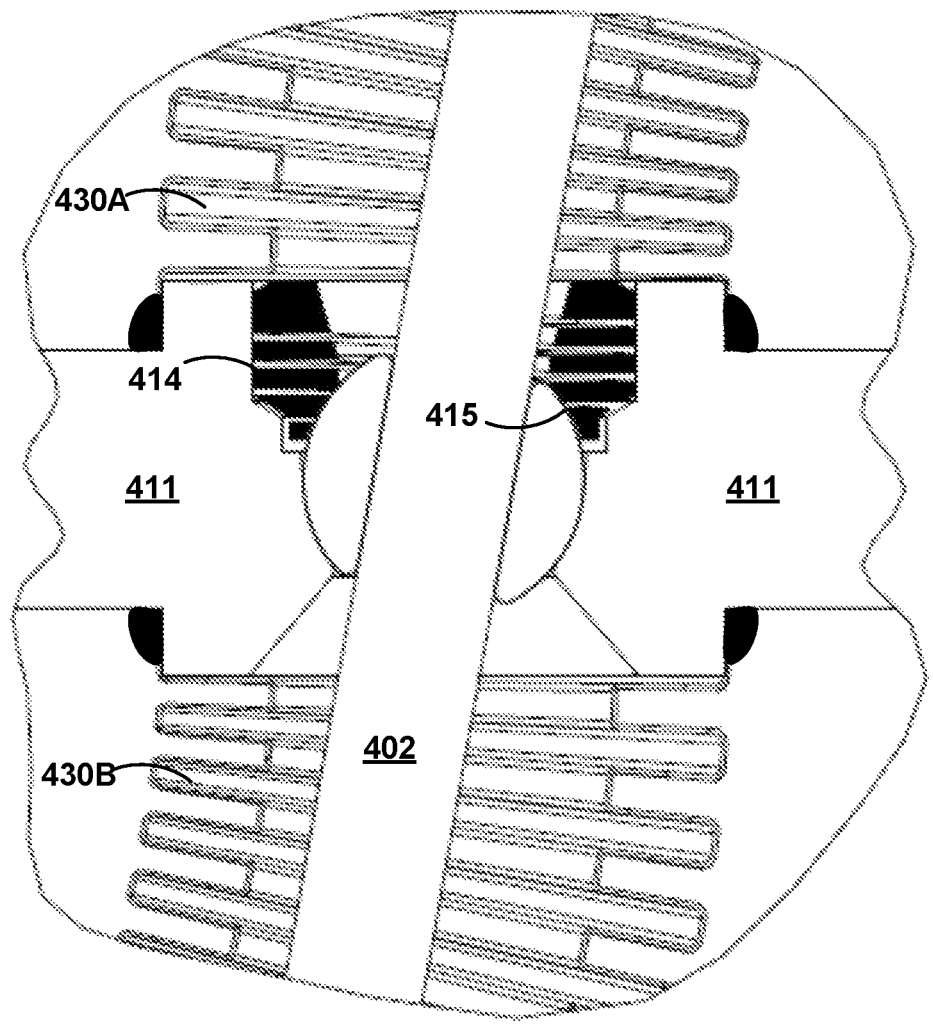
Figure 10C:
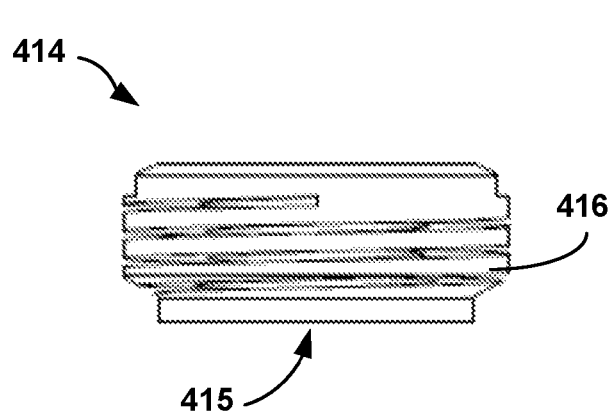
Figure 10D:
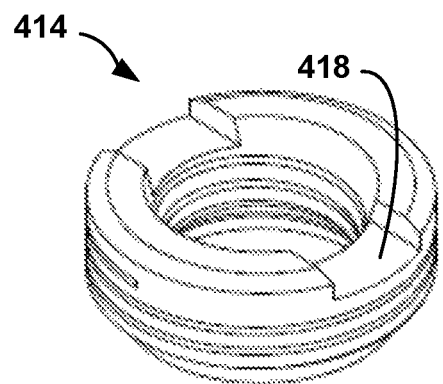

FIG. 10B illustrates a close-up view of central bearing 410, which supports a central portion of nutating shaft 402. Central bearing 410 allows nutating shaft 402 to pivot relative to center plate 411. As further indicated in FIG. 10B, central bearing 410 is further supported by set screw 414, which includes bearing surface 415 to receive central bearing 410. In this manner, set screw 414 represents a ball retention feature. As illustrated in FIGS. 10C and 10D, set screw 414 includes threads 416 to couple to corresponding threads in center plate 411 and slot 418 to receive a driver head, such as a flathead screwdriver during assembly of nutating mechanical feedthrough 400.

The inclusion of a ball retention feature may provide one or more design options. A ball retention feature could be used wherever a ball feature is used, such as central bearing 410, which means that it could be used on center plate 411 and/or on plates 407, 409. In addition, the use of a ball retention feature would allow tolerances of feature size, position, material properties and other characteristics to be liberalized. Due to the nature of the ongoing contact between set screw 414 and central bearing 410 during operation of mechanical feedthrough 400, the properties of central bearing 410 may be controlled by selecting matching of ball and retainer radii, selecting materials for ball and retainer, including the use of coatings, such as diamond-like carbon on the ball and/or on the retainer to improve wear characteristics.

While central bearing 410 is in direct contact with bearing surface 415 of set screw 414, in an alternate design, set screw 414 may be replaced with a set screw, spring and separate component including a bearing surface in a stacked arrangement. Such an arrangement may facilitate and adjustable level of force on between the bearing surface and central bearing 410 by varying the depth of the set screw. Such a design provides increased manufacturing tolerances as compared to the assembly shown in FIG. 10B.

FIG. 11 is a conceptual diagram of assembly 500, which includes motor 15 (FIG. 1) within a hermetically sealed enclosure 421 and nutating mechanical feedthrough 400, which facilitates mechanical coupling rotating output shaft 516 of motor 15 through the boundary of hermetically sealed enclosure 421. In particular, rotating output shaft 516 drives plate 407 of nutating mechanical feedthrough 400 to nutate nutating shaft 402. In turn, nutating shaft 402 functions to rotate plate 409, which drives load 502.

In different examples, load 502 may represent a mechanically adjustable medical lead, such as any of mechanically adjustable medical leads 100, 200 and 300 or other mechanical device. For example, plate 409 may represent one of the rotating members 112, 113, 114, 212, 214, 312, 314 of medical leads 100, 200 and 300 or plate 409 may be mechanically coupled to one of the rotating members 112, 113, 114, 212, 214, 312, 314 of medical leads 100, 200 and 300 directly or via an engagement mechanism, such as a mechanical or magnetic clutch engagement mechanism.

Assembly 500 forms a substantially sealed enclosure 421 encasing motor 15, rotating output shaft 516, the proximal end of the nutating shaft and central bearing 410. As discussed with respect to FIG. 10A, substantially sealed enclosure 421 may be a hermetically sealed enclosure.

Figure 12:
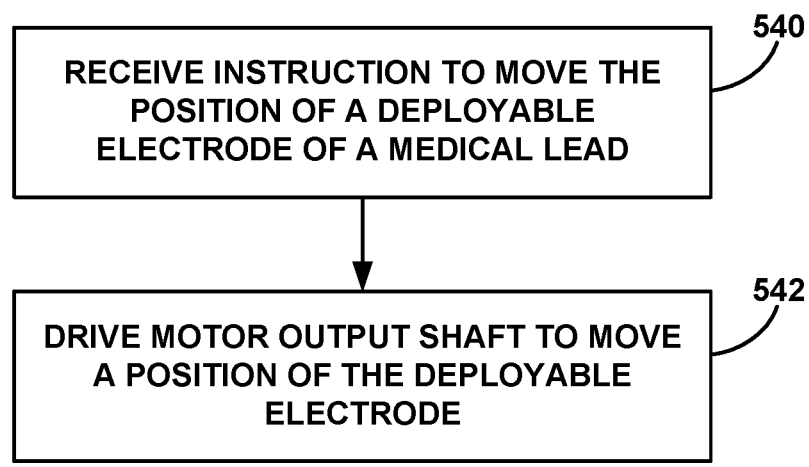
FIG. 12 is a flowchart illustrating an example technique for operating a motor within a hermetically sealed enclosure to adjust a spacing between a proximal end of a medical lead and an electrode of the medical lead.

FIG. 12 is a flowchart illustrating an example technique for operating a motor within a hermetically sealed enclosure to adjust a spacing between a proximal end of a medical lead and an electrode of the medical lead. For clarity, the techniques of FIG. 12 are described with respect to system 10, including IMD 20 (FIG. 2), mechanically adjustable medical lead 100 (FIG. 4) and assembly 500 (FIG. 11). The techniques of FIG. 12 may also be practiced using the mechanical feedthroughs of FIGS. 15-17 The techniques of FIG. 12 may also be practiced using one of the mechanical feedthroughs of FIGS. 15-17 in combination with a mechanically adjustable lead, such as lead 100.

First, processor 70 of IMD 20 receives an instruction to move the position of one or both of electrodes 104, 105 of medical lead 100 (540). For example, processor 70 of IMD 20 may receive the instruction from a control program stored in memory 72 of IMD 20 or processor 70 of IMD 20 may receive the instruction from programmer 19. In some examples, a clinician may directly instruct processor 70 of IMD 20 to move the position of one or both of electrodes 104, 105 via programmer 19.

Next, processor 70 of IMD 20 operates motor 15, which is located within sealed enclosure 421, which may be a hermetically sealed enclosure, to drive a rotating output shaft of the motor and move a position of one or both of electrodes 104, 105 of medical lead 100 (542). For example, processor 70 may operate motor 15 to drive rotatable member 112 to move a position of electrodes 104, 105 to adjust the spacing between the proximal end of medical lead body 102 and electrodes 104, 105 by varying an overall length of medical lead 100. Alternatively or in addition, processor 70 may operate motor 15 to drive rotatable member 114 to move a position of electrodes 104, 105 to directly vary spacing between electrodes 104, 105 via opposing threads 115A and 115B. While the techniques of FIG. 12 are described with respect to mechanically adjustable medical lead 100, the described techniques are also applicable to other mechanically adjustable medical leads, such as mechanically adjustable medical leads 200 and 300.

Figure 13:
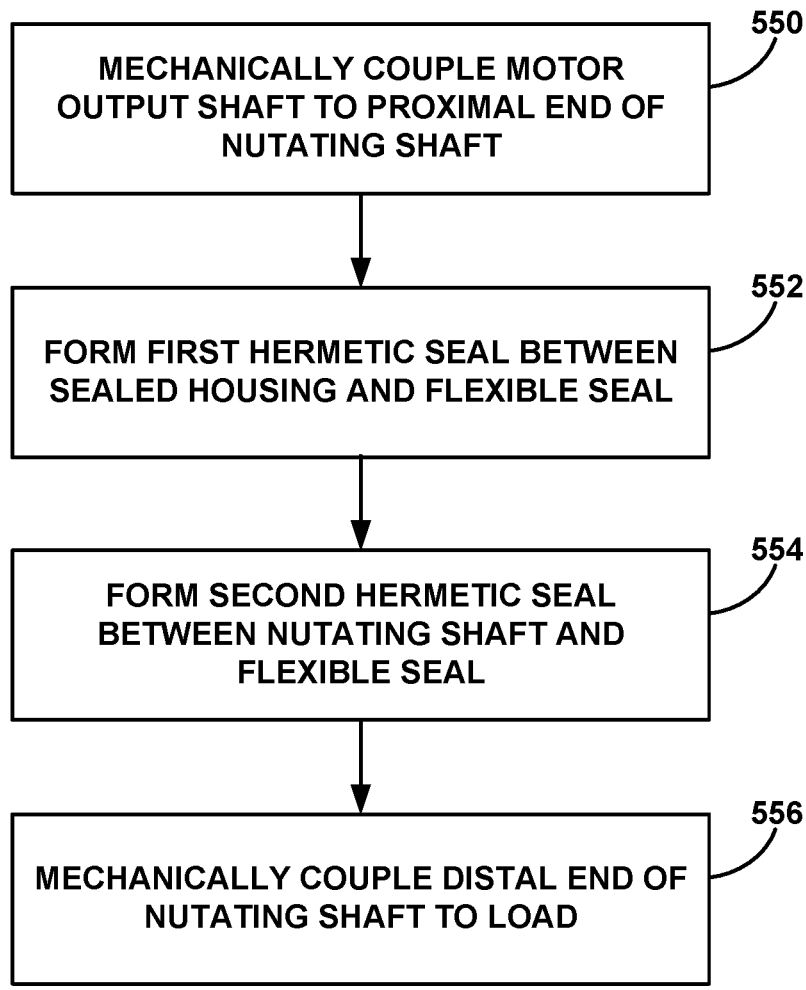
FIG. 13 is a flowchart illustrating an example technique for manufacturing a nutating mechanical feedthrough that facilitates mechanical coupling to a rotating shaft within a hermetically sealed enclosure.

FIG. 13 is a flowchart illustrating an example technique for manufacturing a nutating mechanical feedthrough that facilitates mechanical coupling to a rotating shaft within a hermetically sealed enclosure. For clarity, the techniques of FIG. 13 are described with respect to system 10, including IMD 20 (FIG. 2), mechanically adjustable medical lead 100 (FIG. 4) and assembly 500 (FIG. 11).

The techniques include mechanically coupling rotating output shaft 516 of motor 15 within a sealed housing to proximal end 403 of nutating shaft 402 (550). As mentioned above, nutating shaft 402 is supported by central bearing 410. Nutating shaft 402 passes through boundary of the sealed environment, whereas central bearing 410 is within the sealed housing. The techniques further include forming a first hermetic seal at an interface between housing 420, which contains the sealed environment and flexible seal 430A, a proximal side of flexible seal 430A covering a distal side of central bearing 410 (552). Weld joint 434 represents one example of such a first hermetic seal. The techniques further include forming a second hermetic seal at an interface between a distal portion of nutating shaft 402 and a distal side of flexible seal 430A (554). Weld joint 436 represents one example of such a first hermetic seal. As mentioned above, housing 420, flexible seal 430A, weld joint 434 and weld joint 436 may combine to form a hermetically sealed enclosure encasing motor 15, rotating output shaft 516, proximal end 403 of nutating shaft 402 and central bearing 410.

The techniques may further include mechanically coupling distal end 404 of nutating shaft 402 to load 502 (556). In one example, load 502 represents a rotatable member of a mechanically adjustable medical lead, such that nutation of nutating shaft 402 is configured to rotate the rotatable member of the mechanically adjustable medical lead to move a position of an electrode of the mechanically adjustable medical lead to adjust a spacing between a proximal end of the medical lead and the electrode.

Figure 14:
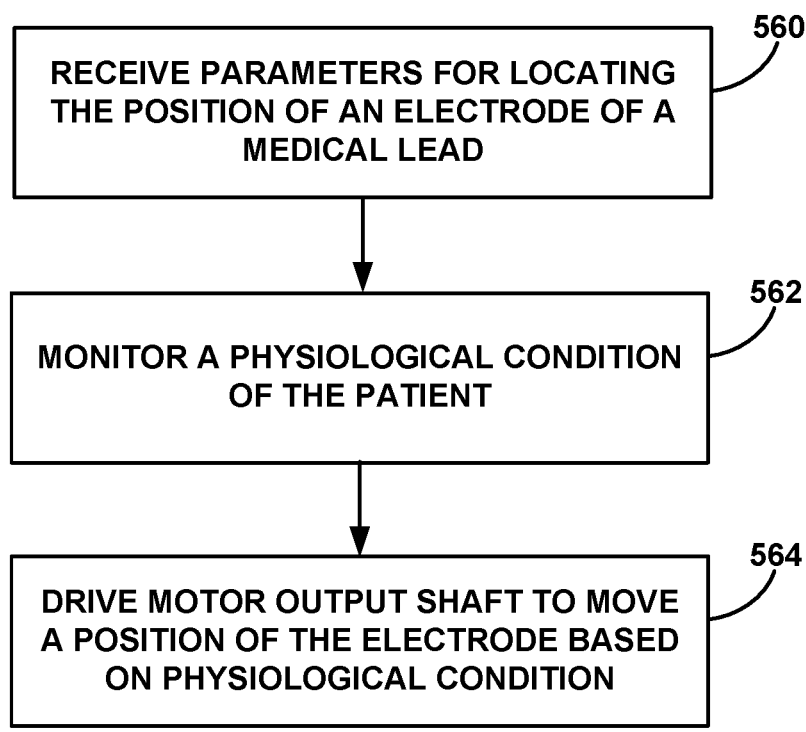
FIG. 14 is a flowchart illustrating an example technique for adjusting the position of an electrode of a mechanically adjustable medical lead implanted within a patient based on a physiological condition of the patient.

FIG. 14 is a flowchart illustrating an example technique for adjusting the position of an electrode of a mechanically adjustable medical lead implanted within a patient based on a physiological condition of the patient. For clarity, the techniques of FIG. 14 are described with respect to system 10, including IMD 20 (FIG. 2) and mechanically adjustable medical lead 100 (FIG. 4). The techniques of FIG. 14 may also be practiced using one of the mechanical feedthroughs of FIGS. 15-17 in combination with a mechanically adjustable lead, such as lead 100.

First, processor 70 of IMD 20 receives an instruction including parameters for locating the position of one or both of electrodes 104, 105 of medical lead 100 based on physiological condition of patient 12 (560). For example, processor 70 of IMD 20 may receive the instruction from a control program stored in memory 72 of IMD 20 or processor 70 of IMD 20 may receive the instruction from programmer 19. In some examples, a clinician may directly instruct processor 70 of IMD 20 to move the position of one or both of electrodes 104, 105 via programmer 19 based on the parameters for locating the position of one or both of electrodes 104, 105 of medical lead 100 based on physiological condition of patient 12.

Processor 70 monitors one or more physiological conditions of patient 12 (562). The physiological conditions of patient 12 may indicate an efficacy of a therapy or sensing thereby providing an indication of the suitability of the positioning of electrodes 104, 105. In some examples, physiological conditions of patient 12 may be at least partially monitored via electrodes 104, 105. For example, the physiological conditions may include patient activity level, patient posture, patient tremors, patient sleep characteristics and/or patient brain signals monitored over time. In different examples, the monitored physiological conditions may be monitored over various time periods such as time periods of a week to time periods of less than one second. In some particular examples, the parameters for locating the position of one or both of electrodes 104, 105 may include particular brain signal characteristics or biomarkers.

In some examples, the biomarker includes a particular signal characteristic, such as, but not limited to, any one or more of a time domain characteristic of a bioelectrical brain signal (e.g., a mean, median, peak or lowest amplitude, instantaneous amplitude, waveform morphology, pulse frequency or pulse to pulse variability), a frequency domain characteristic of a bioelectrical brain signal (e.g., an energy level in one or more frequency bands), a pattern of the bioelectrical brain signal over time, or some other measurable characteristic of a sensed bioelectrical brain signal. In some cases, the biomarker may be considered the absence of a particular characteristic (e.g., the energy level in a particular frequency band is not over a threshold level). The presence or absence of a signal characteristic may be indicative of a particular patient state and or electrode positioning. When a sensed bioelectrical brain signal includes, or in some cases, does not include, the signal characteristic, the sensed bioelectrical brain signal may indicate patient 12 is in a state in which the effects of therapy may have changed, e.g., diminished relative to a baseline state in which the efficacious therapy was observed. The biomarker may be specific to patient 12, a patient condition, or both, such that the biomarkers based on which the notifications are generated may differ between patients. Thus, the sensed bioelectrical brain signal may indicate an efficacy of the therapy.

In some examples, in order to determine whether a sensed bioelectrical brain signal includes the biomarker, processor 70 may compare a time domain characteristic (e.g., an amplitude) of the sensed bioelectrical brain signal with a stored value, compare a particular power level within a particular frequency band of the bioelectrical brain signal to a stored value, determine whether the sensed bioelectrical brain signal substantially correlates to a template, or combinations thereof. For example, processor 70 may determine one or more frequency band characteristics of a sensed bioelectrical brain signal and determine the sensed bioelectrical brain signal includes the biomarker in response to determining the one or more frequency band characteristics meet a particular set of criteria associated with generating the notification. As an example, in response to determining a sensed bioelectrical brain signal has a beta band power level that is greater than the beta band power level of a baseline bioelectrical brain signal, and a gamma band power level that is less than the gamma band power level of the baseline bioelectrical brain signal, processor 70 may determine the sensed bioelectrical brain signal includes a biomarker that indicates a change in efficacy of therapy delivered by IMD 20 (relative to the baseline state). In this case, the biomarker includes the above-identified power level conditions in the beta and gamma bands. As another example, processor 70 may determine the sensed bioelectrical brain signal includes the biomarker in response to determining the sensed bioelectrical brain signal does not substantially correlate (e.g., correlate or nearly correlate) with a template signal. Other techniques are also contemplated.

The biomarker may be determined based on a bioelectrical brain signal sensed when therapy delivery by IMD 20 was determined to be efficacious, e.g., based on a subjective patient 12 rating or other patient input, based on a sensed parameter (e.g., a physiological signal or based on a patient activity level determined based on signals generated by one or more motion sensors), or any other technique or combinations of techniques. In some examples, processor 70 may determine the biomarker by at least determining a first signal characteristic of a bioelectrical brain signal sensed when therapy delivery by IMD 20 was determined to be efficacious. The first signal characteristic may be indicative of a patient state in which IMD 20 is delivering efficacious therapy to patient 12 and the biomarker may be selected to be indicative of a patient state in which therapy delivery by IMD 20 is not sufficiently efficacious. In this example, the biomarker may be a signal characteristic of a sensed bioelectrical brain signal that is not equal to the first signal characteristic and is outside of a tolerance range defined relative to the first signal characteristic. For example, if the first signal characteristic is a first power level within a beta band of a sensed bioelectrical brain signal, a biomarker may be a power level within the beta band that is not equal to the first power level or any value within a tolerance range of the first power level.

In another example, processor 70 may determine the biomarker by at least determining a second signal characteristic of a bioelectrical brain signal sensed when patient 12 is in a state in which efficacious effects of therapy delivery by IMD 20 are not observed (e.g., a state prior to any therapy delivery by IMD 20 or a state in which IMD 20 is otherwise not delivering therapy to patient 12). Again, the biomarker may be selected to be indicative of a patient state in which therapy delivery by IMD 20 is not sufficiently efficacious. Thus, in this example, the biomarker may be the second signal characteristic and values within a tolerance range of the second signal characteristic (e.g., the tolerance range measured relative to the second signal characteristic defines a range of values for the biomarker). For example, if the second signal characteristic is a second power level within a beta band of a sensed bioelectrical brain signal, a biomarker may be a power level within the beta band that is equal to the second power level or any value within a tolerance range of the second power level.

In some examples, the stimulation therapy delivered via electrodes 104, 105 may be varied in combination with the positioning of electrodes 104, 105. Adjusting the therapy may include, for example, changing parameters associated with a therapy such as stimulation amplitude including current and/or voltage amplitude, pulse width, pulse rate, the number of activated leads or electrodes in a group or program, electrode combination, electrode polarity and/or other therapy parameter adjustments.

Prior to, during, and/or following the monitoring of the physiological conditions of patient 12, processor 70 of IMD 20 operates motor 15 to drive a rotating output shaft of the motor and move a position of one or both of electrodes 104, 105 of medical lead 100 (564). For example, processor 70 may operate motor 15 to drive rotatable member 112 to move a position of electrodes 104, 105 to adjust the spacing between the proximal end of medical lead body 102 and electrodes 104, 105 by varying an overall length of medical lead 100. Alternatively or in addition, processor 70 may operate motor 15 to drive rotatable member 114 to move a position of electrodes 104, 105 to directly vary spacing between electrodes 104, 105 via opposing threads 115A and 115B. In this manner, IMD 20 and processor 70 are suitable for implementing electrode positioning adjustments facilitated by mechanically adjustable medical lead 100.

Figure 15:
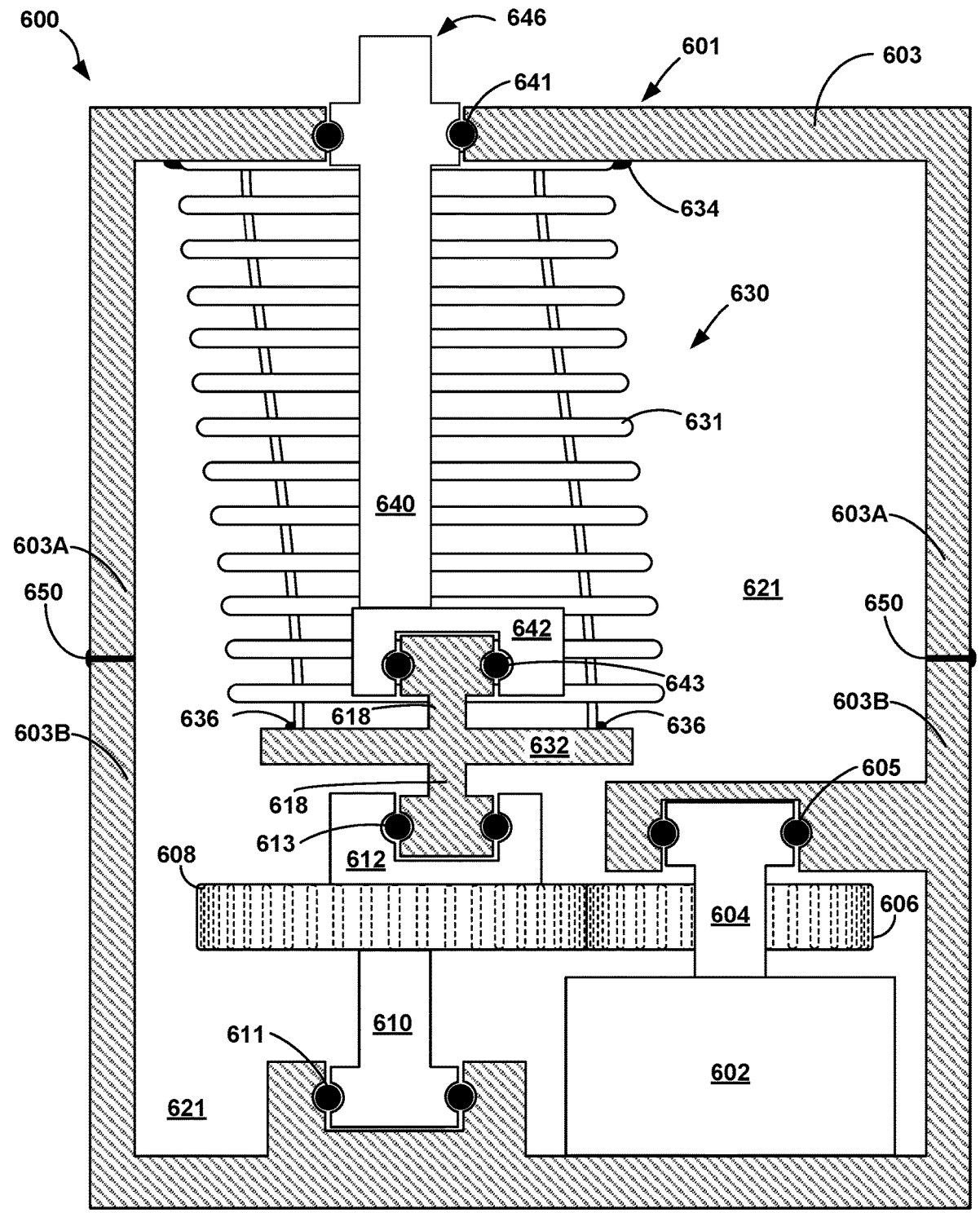
FIG. 15 illustrates an assembly including a motor and a mechanical feedthrough with a pair of coaxial shafts coupled with an offset pin and sealed with a flexible seal including an oscillating cap, the offset pin and the oscillating cap being fixed relative to one another as a functionally unitary component.

FIG. 15 illustrates a cross-sectional view of assembly 600, which includes motor 602 and mechanical feedthrough 601. Mechanical feedthrough 601 facilitates mechanical coupling to rotating shaft 640 from within hermetically sealed enclosure 621.

Mechanical feedthrough 601 includes a pair of coaxial shafts 610, 640 coupled with offset pin 618 and sealed with flexible seal 630. Flexible seal 630 includes oscillating cap 632, which is fixed relative to offset pin 618 such that oscillating cap 632 and offset pin 618 represent a functionally unitary component.

Motor 602 operates to drives coaxial shaft 640, which is locate outside hermetically sealed enclosure 621 via mechanical feedthrough 601. Mechanical feedthrough 601 includes motor output shaft 604, which is mechanically coupled to gear 606 and supported by bearings 605, which are attached to housing 603. Gear 606 drives gear 608, which is coupled to coaxial shaft 610. Coaxial shaft 610 is supported by bearings 611, which are attached to housing 603. Offset bearing support 612 is coupled to, and driven in a circular motion by, coaxial shaft 610 about the rotational axis of coaxial shaft 610. Offset bearing support 612 drives offset pin 618, which is fixed relative to oscillating cap 632. Bearings 613 support the interface between offset pin 618 and offset bearing support 612.

Oscillating cap 632 is prevented from substantially rotating by is connection to bellows 631, which is secured to housing 603. Nonetheless, the circular motion of offset bearing support 612 drives offset pin 618 and oscillating cap 632 in an equivalent oscillating motion without rotation. Offset pin 618 extends past oscillating cap 632 and outside the hermetic boundary to drive offset bearing support 642 in a circular motion. Bearings 643 support the interface between offset bearing support 642 and offset pin 618. Offset bearing support 642 is fixed relative to coaxial shaft 640, such that the circular motion of offset bearing support 642 drives rotation of coaxial shaft 640. Coaxial shaft 640 is supported by bearings 641 in housing 603 and the distal end 646 of coaxial shaft 640 extends beyond the perimeter of housing 603 to drive a component outside the hermetically sealed enclosure 621.

Because cap 632 does not rotate, cap 632, facilitates hermetic sealing between coaxial shafts 610, 640 while allowing the mechanical coupling of coaxial shafts 610, 640. In the example of mechanical feedthrough 601, the hermetic boundary between coaxial shafts 610, 640 includes housing 603, bellows 631, oscillating cap 632 and weld joints 634, 636.

In the example of assembly 600, motor 602, first coaxial shaft 610, and portions of offset pin 618 and oscillating cap 632 are within the hermetically sealed enclosure 621. As illustrated by this example, mechanical feedthrough 601 facilitates mechanical coupling rotating shaft 640 from within hermetically sealed enclosure 621. For example, mechanical feedthrough 601 may be suitable for connecting any of medical leads, 100, 200 and 300 to a motor, such as motor 602 or motor 15.

The hermetically sealed enclosure is formed by housing 603 and flexible seal 630, which includes bellows 631 and oscillating cap 632. Mechanical feedthrough 601 further includes weld joint 634, which seals an interface of bellows 631 and housing 603 and weld joint 636, which seals an interface of bellows 631 and oscillating cap 632. In this manner, housing 603, bellows 631, oscillating cap 632, and weld joints 634, 636 combine to form a hermetic boundary between coaxial shafts 610, 640 to contain hermetically sealed enclosure 621.

In some examples, bellows 631 may include a metal bellows, such as an electroformed metal bellows. The metal bellows may include alternating layers of copper and nickel. In some examples, electroforming such a metal bellows may include plating the alternating layers of copper and nickel on an aluminum mandrel before dissolving the aluminum mandrel with an acid to leave the metal bellows behind. The design of mechanical feedthrough 601 and the metal bellows in particular may be selected to limit the operating stress on the metal bellows during the motion of oscillating cap 632. In one example, the metal bellows may be subjected to an operating stress of less than forty percent of its yield stress. In another example, the metal bellows may be subjected to an operating stress of no more than twenty percent of its yield stress. Limiting the operating stress of the metal bellows to the smallest possible percentage of its yield stress facilitates forming a reliable hermetic boundary with the metal bellows. Limiting the operating stress may increase the service life of the metal bellows.

In some examples, hermetically sealed enclosure 621 may be filled with a selected fluid, such as an inert gas, oil or other liquid. Hermetically sealed enclosure 621 may further provide one or more of the additional design options for an implantable medical device. Hermetically sealed enclosure 621 may enable the option of removing traditional electrical feedthroughs from neurostimulation system designs employing rotary prime movers. Hermetically sealed enclosure 621 may further facilitate placing both ends of an electrical feedthrough in a dry operating environment. Hermetically sealed enclosure 621 may further allow critical mechanical components of an implantable medical device, not just motors and other electrical components, to be sealed within. In addition, hermetically sealed enclosure 621 may remediate corrosion and dendritic growth issues by depriving these processes of the chemical fuel required to sustain them.

In the example illustrated in FIG. 15, housing 603 is formed from two housing components 603A, 603B for purposes of manufacturability. Housing components 603A, 603B are joined with weld joins 650 to maintain the hermetic boundary. The configuration of housing 603 including housing components 603A, 603B is merely exemplary and any number of configurations are possible. In addition, the mechanical coupling between motor shaft 604 and the output provided by coaxial shaft 640 is also merely exemplary, and alternative configurations are possible, including any variety of gear combinations and designs are possible within the spirit of this disclosure. In addition, multiple variations of mechanical feedthrough 601 are also within the spirt of this disclosure. Two such variations are described with respect to FIGS. 16 and 17.

Figure 16:
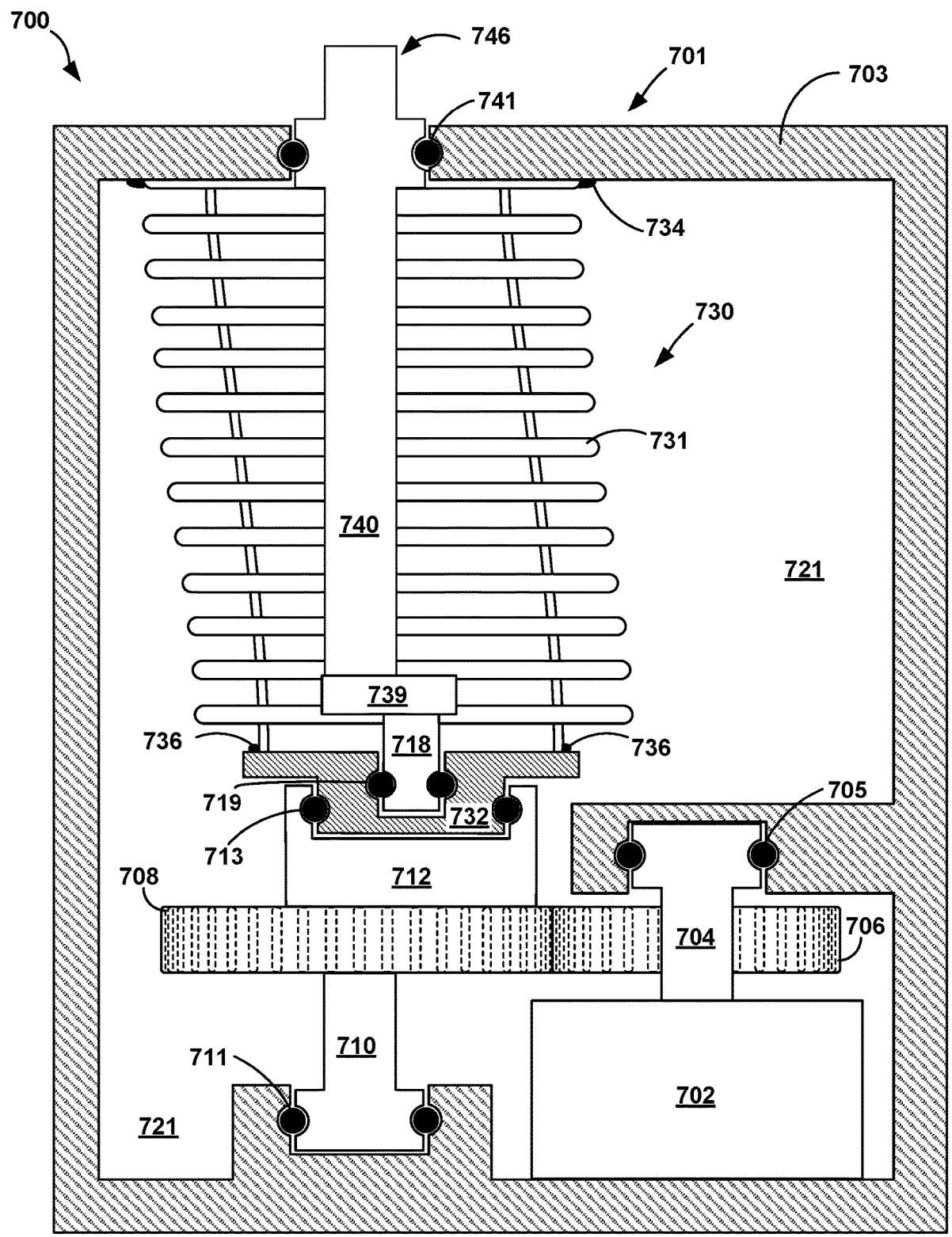
FIG. 16 illustrates an assembly including a motor and a mechanical feedthrough with a pair of coaxial shafts coupled with an offset pin and sealed with a flexible seal including an oscillating cap, the offset pin and the second shaft outside the sealed housing being fixed relative to one another as a functionally unitary component.

FIG. 16 illustrates a cross-sectional view of assembly 700, which includes motor 702 and mechanical feedthrough 701. Mechanical feedthrough 701 facilitates mechanical coupling to rotating shaft 740 from within hermetically sealed enclosure 721. Mechanical feedthrough 701 includes a pair of coaxial shafts 710, 740 coupled with offset pin 718 and sealed with flexible seal 730. Flexible seal 730 includes oscillating cap 732. Offset pin 718 is fixed relative to coaxial shaft 740 such that offset pin 718 and coaxial shaft 740 represent a functionally unitary component. With the example of assembly 700, offset pin 718 and coaxial shaft 740 are outside the hermetically sealed enclosure 721.

Assembly 700 is functionally similar to assembly 600. In addition, like numbered elements of assembly 700 correspond to the like numbered elements of assembly 600. For example, motor 702 corresponds to motor 602, housing 703 corresponds to housing 603, flexible seal 730 corresponds to flexible seal 630, etc. For brevity, elements of assembly 700 that are the same or similar to the corresponding elements of assembly 600 are described in limited or no detail with respect to assembly 700.

Motor 702 operates to drives coaxial shaft 740, which is locate outside hermetically sealed enclosure 721 via mechanical feedthrough 701. Mechanical feedthrough 701 includes motor output shaft 704, which is mechanically coupled to gear 706 and supported by bearings 705, which are attached to housing 703. Gear 706 drives gear 708, which is coupled to coaxial shaft 710. Coaxial shaft 710 is supported by bearings 711, which are attached to housing 703. Offset bearing support 712 is coupled to, and driven in a circular motion by, coaxial shaft 710 about the rotational axis of coaxial shaft 710. Offset bearing support 712 drives oscillating cap 732. Bearings 713 support the interface between oscillating cap 732 and offset bearing support 712.

Oscillating cap 732 is prevented from substantially rotating by is connection to bellows 731, which is secured to housing 703. Nonetheless, the circular motion of offset bearing support 712 drives oscillating cap 732 in an equivalent oscillating motion without rotation. Oscillating cap 732 drives offset pin 718, which is located outside the hermetic boundary, in a circular motion. Bearings 719 support the interface between oscillating cap 732 and offset pin 718. Offset pin 718 and offset platform 739 are fixed relative to coaxial shaft 740, such that the circular motion of offset platform 739 drives rotation of coaxial shaft 740. Coaxial shaft 740 is supported by bearings 741 in housing 703 and the distal end 746 of coaxial shaft 740 extends beyond the perimeter of housing 703 to drive a component outside the hermetically sealed enclosure 721.

Figure 17:
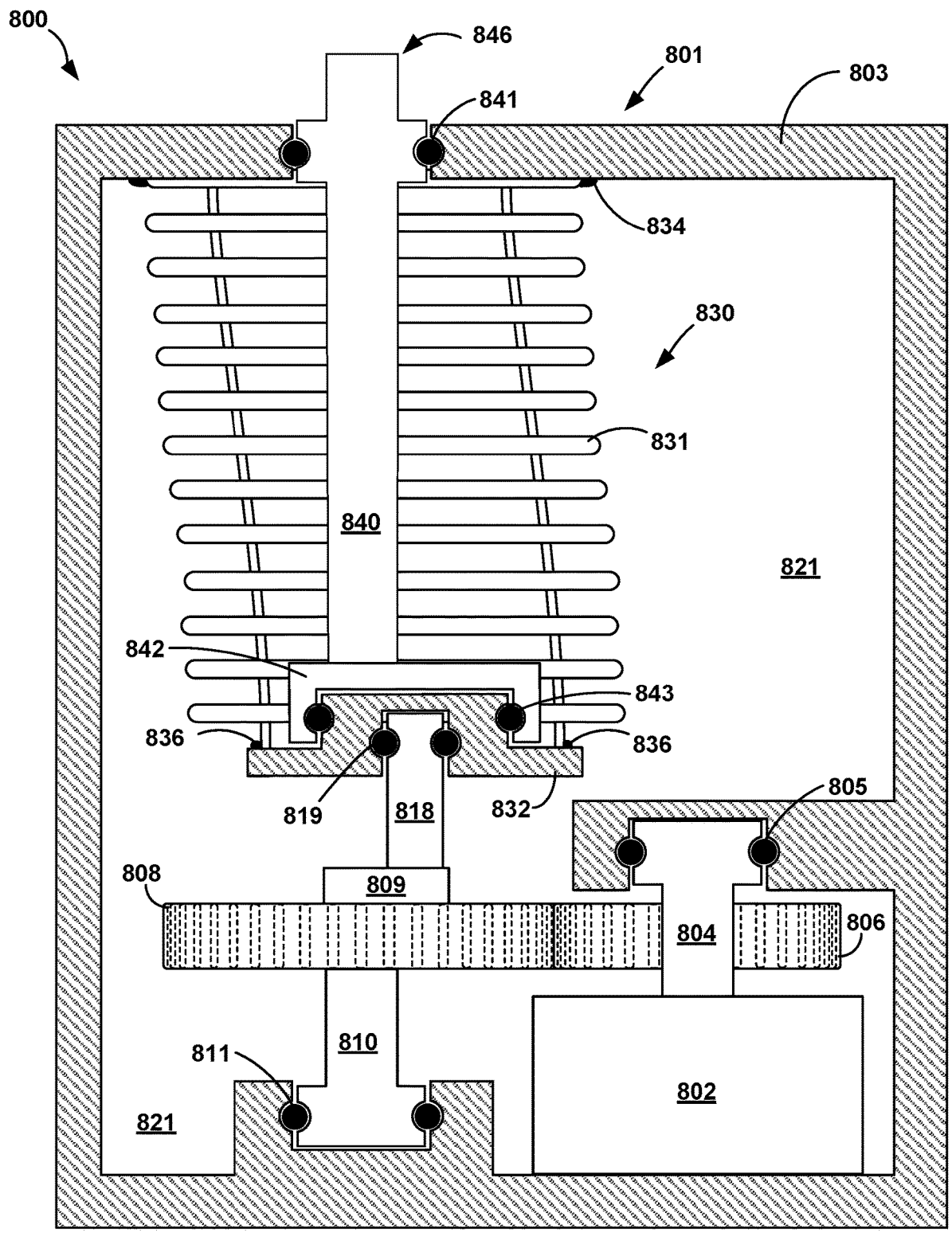
FIG. 17 illustrates an assembly including a motor and a mechanical feedthrough with a pair of coaxial shafts coupled with an offset pin and sealed with a flexible seal including an oscillating cap, the offset pin and the second shaft within the sealed housing being fixed relative to one another as a functionally unitary component.

FIG. 17 illustrates a cross-sectional view of assembly 800, which includes motor 802 and mechanical feedthrough 801. Mechanical feedthrough 801 facilitates mechanical coupling to rotating shaft 840 from within hermetically sealed enclosure 821. Mechanical feedthrough 801 includes a pair of coaxial shafts 810, 840 coupled with offset pin 818 and sealed with flexible seal 830. Flexible seal 830 includes oscillating cap 832. Offset pin 818 is fixed relative to coaxial shaft 810 such that offset pin 818 and coaxial shaft 810 represent a functionally unitary component. With the example of assembly 800, offset pin 818 and coaxial shaft 810 are within the hermetically sealed enclosure 821.

Assembly 800 is functionally similar to assembly 600. In addition, like numbered elements of assembly 800 correspond to the like numbered elements of assembly 600. For example, motor 802 corresponds to motor 602, housing 803 corresponds to housing 603, flexible seal 830 corresponds to flexible seal 630, etc. For brevity, elements of assembly 800 that are the same or similar to the corresponding elements of assembly 600 are described in limited or no detail with respect to assembly 800.

Motor 802 operates to drives coaxial shaft 840, which is locate outside hermetically sealed enclosure 821 via mechanical feedthrough 801. Mechanical feedthrough 801 includes motor output shaft 804, which is mechanically coupled to gear 806 and supported by bearings 805, which are attached to housing 803. Gear 806 drives gear 808, which is coupled to coaxial shaft 810. Coaxial shaft 810 is supported by bearings 811, which are attached to housing 803. Offset platform 809 is coupled to, and driven in a circular motion by, coaxial shaft 810 about the rotational axis of coaxial shaft 810. Offset pin 818 and offset platform 809 are fixed relative to coaxial shaft 810, such that rotation of coaxial shaft 810 drives circular motion of offset platform 809 and offset pin 818.

Offset pin 818 drives oscillating cap 832. Bearings 819 support the interface between offset pin 818 and oscillating cap 832. Oscillating cap 832 is prevented from substantially rotating by is connection to bellows 831, which is secured to housing 803. Nonetheless, the circular motion of offset pin 818 drives oscillating cap 832 in an equivalent oscillating motion without rotation. Oscillating cap 832 drives offset bearing support 842, which is located outside the hermetic boundary, in a circular motion. Bearings 843 support the interface between oscillating cap 832 and offset bearing support 842. Offset bearing support 842 is fixed relative to coaxial shaft 840, such that the circular motion of offset bearing support 842 drives rotation of coaxial shaft 840. Coaxial shaft 840 is supported by bearings 841 in housing 803 and the distal end 846 of coaxial shaft 840 extends beyond the perimeter of housing 803 to drive a component outside the hermetically sealed enclosure 821.

Figure 18:
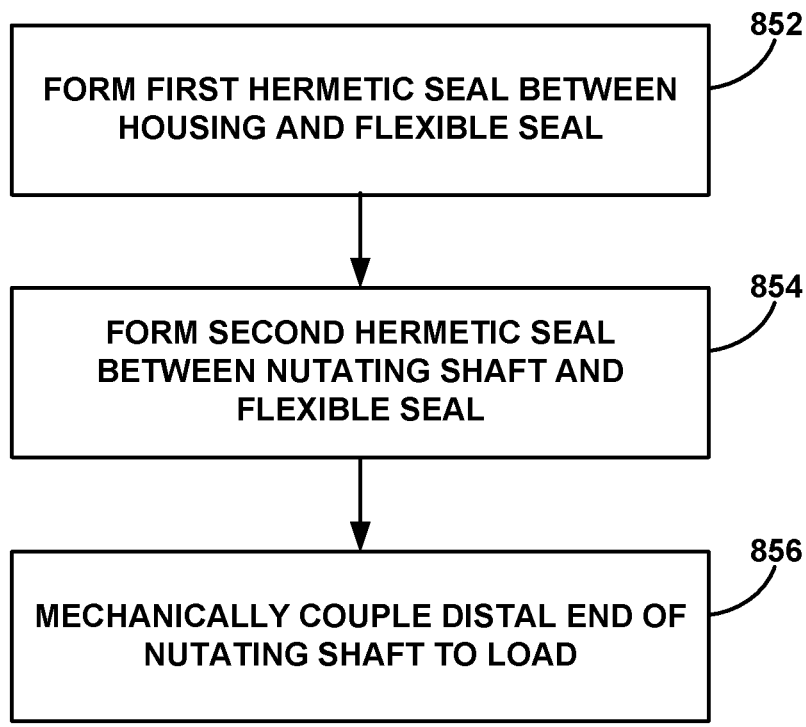
FIG. 18 is a flowchart illustrating an example technique for manufacturing a mechanical feedthrough that facilitates mechanical coupling to a rotating shaft within a hermetically sealed enclosure.

FIG. 18 is a flowchart illustrating an example technique for manufacturing a mechanical feedthrough that facilitates mechanical coupling to a rotating shaft within a hermetically sealed enclosure. For clarity, the techniques of FIG. 18 are described with respect to system 10, including IMD 20 (FIG. 2), mechanically adjustable medical lead 100 (FIG. 4) and assembly 600 (FIG. 15).

The techniques include forming a first hermetic seal at an interface between bellows 631 and oscillating cap 632 (852). Weld joint 636 represents one example of such a first hermetic seal. The techniques further include forming a second hermetic seal at an interface between housing 603, which contains the sealed environment and flexible seal 630 (854). Weld joint 434 represents one example of such a first hermetic seal. The techniques optionally include assembling and sealing housing components 603A, 603B. Weld joint 650 represents one example of such a hermetic seal sealing housing components 603A, 603B. For example, assembling and sealing housing components 603A, 603B may occur between steps 852 and 854. As mentioned above, housing 603, flexible seal 430, weld joints 634, 636, 650 may combine to form a hermetically sealed enclosure 621 encasing motor 602, gears 606, 608 first coaxial shaft 610, and portions of offset pin 618 and oscillating cap 632.

The techniques may further include mechanically coupling distal end 646 of coaxial shaft 640 to a load (556). In one example, the load may represents a rotatable member of a mechanically adjustable medical lead, such that rotation of coaxial shaft 640 is configured to rotate the rotatable member of the mechanically adjustable medical lead to move a position of an electrode of the mechanically adjustable medical lead to adjust a spacing between a proximal end of the medical lead and the electrode.

While the description primarily refers to implantable electrical medical leads and implantable medical devices that deliver electrical stimulation therapy to a patient's brain, for example, DBS, the features and techniques described herein are useful in other types of medical device systems, which may include other types of implantable medical leads and implantable medical devices. For example, the features and techniques described herein may be used in systems with medical devices that deliver electrical stimulation therapy to a patient's heart, for example, pacemakers, and pacemaker-cardioverter-defibrillators. As other examples, the features and techniques described herein may be embodied in systems that deliver other types of electrical stimulation therapy (for example, spinal cord stimulation, peripheral nerve stimulation, pelvic nerve stimulation, gastric nerve stimulation or vagal nerve stimulation), stimulation of at least one muscle or muscle groups, stimulation of at least one organ such as gastric system stimulation, stimulation concomitant to gene therapy, and, in general, stimulation of any tissue of a patient.

In addition, while the examples shown in the figures include medical leads coupled at their proximal ends to a stimulation therapy generator in, for example, an implantable medical device, located remotely from the electrodes, other configurations are also possible and contemplated. In some examples, a medical lead comprises a portion of a housing, or a member coupled to a housing, of a stimulation generator located proximate to or at the stimulation site, for example, as a microstimulator. In other examples, a medical lead comprises a member at stimulation site that is wirelessly coupled to an implanted or external stimulation generator or generator.

Some examples of this disclosure are described below.

Example 1A. An assembly comprising: a sealed housing; a motor within the sealed housing, the motor including a rotating output shaft; a nutating shaft, wherein a proximal end of the nutating shaft is coupled to the rotating output shaft and within the sealed housing; a central bearing passing through the sealed housing and supporting a central portion of the nutating shaft and within the sealed housing; and a flexible seal, a proximal side of the flexible seal covering a distal side of the central bearing, and a distal side of the flexible seal being secured to a distal portion of the nutating shaft located distally relative to the central bearing, wherein the sealed housing and the flexible seal combine to form a substantially sealed enclosure encasing the motor, the rotating output shaft, the proximal end of the nutating shaft and the central bearing.

Example 2A. The assembly of example 1A, wherein flexible seal is substantially fixed to the sealed housing and the nutating shaft.

Example 3A. The assembly of example 1A, wherein the nutating shaft is configured to only nutate and not rotate substantially when motor operates to rotate the rotating output shaft.

Example 4A. The assembly of example 1A, wherein the central bearing includes a radial spherical bearing.

Example 5A. The assembly of example 1A, wherein the flexible seal includes a metal bellows.

Example 6A. The assembly of example 5A, wherein the metal bellows includes an electroformed metal bellows.

Example 7A. The assembly of example 5A, further comprising: a first weld joint sealing an interface of the metal bellows and the sealed housing; and a second weld joint sealing an interface of the metal bellows and the nutating shaft.

Example 8A. The assembly of example 1A, wherein the sealed housing and the flexible seal combine to form a hermetically sealed enclosure encasing the motor, the rotating output shaft, the proximal end of the nutating shaft and the central bearing.

Example 9A. The assembly of example 1A, further comprising a mechanically adjustable medical lead, the mechanically adjustable medical lead including a rotatable member mechanically connected to a distal end of the nutating shaft, wherein operation of the motor to rotate the rotating output shaft rotates the rotatable member of the mechanically adjustable medical lead to move a position of an electrode of the mechanically adjustable medical lead to adjust a spacing between a proximal end of the medical lead body and the electrode.

Example 10A. The assembly of example 1A, further comprising a mechanically adjustable medical lead, the mechanically adjustable medical lead including a rotatable member mechanically connected to a distal end of the nutating shaft, wherein operation of the motor to rotate the rotating output shaft rotates the rotatable member of the mechanically adjustable medical lead to move a radial orientation an electrode of the mechanically adjustable medical lead.

Example 11A. A method of adjusting a mechanically adjustable medical lead, wherein the mechanically adjustable medical lead includes an electrode and a rotatable member, the rotatable member being mechanically coupled to the electrode, the method comprising operating a motor within a hermetically sealed enclosure to drive the rotatable member of the medical lead and move a position of the electrode to adjust a spacing between a proximal end of the medical lead and the electrode.

Example 12A. The method of example 11A, wherein the electrode is positioned adjacent a distal end of the medical lead and rotation of the rotatable member varies an overall length of the medical lead.

Example 13A. The method of example 11A, wherein the mechanically adjustable medical lead further includes: an elongated medical lead body, wherein the electrode is located at a distal portion of the medical lead body and the rotatable member positioned adjacent to the proximal end of the medical lead body; and an insulated conductor extending within the medical lead body, the insulated conductor being in electrical contact with the electrode and extending to the proximal end of the medical lead body.

Example 14A. The method of example 11A, wherein the motor and the medical lead are part of an assembly, wherein the assembly further comprises: a sealed housing, wherein the motor is within the sealed housing, the motor including a rotating output shaft; a nutating shaft, wherein a proximal end of the nutating shaft is coupled to the rotating output shaft and within the sealed housing; a central bearing passing through the sealed housing and supporting a central portion of the nutating shaft and within the sealed housing; and a flexible seal, a proximal side of the flexible seal covering a distal side of the central bearing, and a distal side of the flexible seal being secured to a distal portion of the nutating shaft located distally relative to the central bearing, wherein the sealed housing and the flexible seal combine to form the hermetically sealed enclosure encasing the motor, the rotating output shaft, the proximal end of the nutating shaft and the central bearing.

Example 15A. The method of example 14A, wherein flexible seal is substantially fixed to the sealed housing and the nutating shaft.

Example 16A. The method of example 14A, wherein the nutating shaft is configured to only nutate and not rotate substantially when motor operates to rotate the rotating output shaft.

Example 17A. The method of example 14A, wherein the central bearing includes a radial spherical bearing.

Example 18A. The method of example 14A, wherein the flexible seal includes a metal bellows.

Example 19A. The method of example 18A, further comprising: a first weld joint sealing an interface of the metal bellows and the sealed housing; and a second weld joint sealing an interface of the metal bellows and the nutating shaft.

Example 20A. A method of manufacture comprising: mechanically coupling a rotating output shaft of a motor within a sealed housing to a proximal end of a nutating shaft, wherein the nutating shaft is supported by a central bearing passing through the sealed housing and supporting a central portion of the nutating shaft and within the sealed housing; forming a first hermetic seal at an interface between the sealed housing and a flexible seal, a proximal side of the flexible seal covering a distal side of the central bearing; and forming a second hermetic seal at an interface between a distal portion of the nutating shaft located distally relative to the central bearing and a distal side of the flexible seal, wherein the sealed housing, the flexible seal, the first hermetic seal and the second hermetic seal combine to form a hermetically sealed enclosure encasing the motor, the rotating output shaft, the proximal end of the nutating shaft and the central bearing.

Example 21A. The method of example 20A, wherein the flexible seal includes a metal bellows.

Example 22A. The method of example 21A, further comprising electroforming the metal bellows.

Example 23A. The method of example 20A, further comprising mechanically coupling a distal end of the nutating shaft to a rotatable member of a mechanically adjustable medical lead, wherein nutation of the nutating shaft is configured to rotate the rotatable member of the mechanically adjustable medical lead to move a position of an electrode of the mechanically adjustable medical lead to adjust a spacing between a proximal end of the medical lead and the electrode.

Example 24A. The method of example 20A, further comprising mechanically coupling a distal end of the nutating shaft to a rotatable member of a mechanically adjustable medical lead, wherein nutation of the nutating shaft is configured to rotate the rotatable member of the mechanically adjustable medical lead to move a radial orientation an electrode of the mechanically adjustable medical lead.

Example 1B. A mechanically adjustable medical lead comprising: an elongated medical lead body; a retractable electrode located within a distal portion of the medical lead body; an insulated conductor extending within the medical lead body, the insulated conductor being in electrical contact with the electrode and extending to a proximal end of the medical lead body; and a rotatable member positioned adjacent to the proximal end of the medical lead body, wherein rotation of the rotatable member moves a position of the retractable electrode to selectively deploy and retract the retractable electrode from the medical lead body.

Example 2B. The medical lead of example 1B, wherein the mechanically adjustable medical lead includes a threaded joint that transfers the rotation of the rotatable member into substantially linear movement to move the position of the retractable electrode.

Example 3B. The medical lead of example 1B, wherein the rotatable member is a first rotatable member, the mechanically adjustable medical lead further comprising a second rotatable member positioned adjacent to the proximal end of the medical lead body, wherein rotation of the second rotatable member varies an overall length of the medical lead.

Example 4B. The medical lead of example 3B, wherein the mechanically adjustable medical lead includes a threaded joint that transfers the rotation of the second rotatable member to vary the overall length of the medical lead.

Example 5B. The medical lead of example 1B, wherein the retractable electrode is a first electrode, the insulated conductor is a first insulated conductor and the rotatable member is a first rotatable member, the mechanically adjustable medical lead further comprising: a second electrode located adjacent a distal end of the medical lead body; a third electrode located more proximally along the medical lead body as compared to the second electrode; a second insulated conductor extending within the medical lead body, the second insulated conductor being in electrical contact with the second electrode and extending to the proximal end of the medical lead body; a third insulated conductor extending within the medical lead body, the third insulated conductor being in electrical contact with the third electrode and extending to the proximal end of the medical lead body; a second rotatable member positioned adjacent to the proximal end of the medical lead body, wherein rotation of the second rotatable member moves a position of the third electrode along the medical lead body to adjust a spacing between the second electrode and the third electrode.

Example 6B. The medical lead of example 5B, wherein the mechanically adjustable medical lead includes a threaded joint that transfers the rotation of the second rotatable member into substantially linear movement to move the position of the third electrode.

Example 7B. The medical lead of example 1B, wherein the medical lead body has a substantially circular cross-sectional shape.

Example 8B. The medical lead of example 1B, wherein the medical lead comprises a deep brain stimulation (DBS) medical lead.

Example 9B. An assembly comprising: a motor including a rotating output shaft; and a mechanically adjustable medical lead, the mechanically adjustable medical lead comprising: an elongated medical lead body; a retractable electrode located within a distal portion of the medical lead body; an insulated conductor extending within the medical lead body, the insulated conductor being in electrical contact with the retractable electrode and extending to a proximal end of the medical lead body; and a rotatable member positioned adjacent to the proximal end of the medical lead body, wherein the rotatable member is mechanically coupled to and configured to be driven by the rotating output shaft of the motor, wherein rotation of the rotatable member moves a position of the retractable electrode to selectively deploy and retract the retractable electrode from the medical lead body.

Example 10B. The assembly of example 9B, wherein the mechanically adjustable medical lead includes a threaded joint that transfers the rotation of the rotatable member into substantially linear movement to move the position of the retractable electrode.

Example 11B. The assembly of example 9B, wherein the rotatable member is a first rotatable member, the mechanically adjustable medical lead further comprising a second rotatable member positioned adjacent to the proximal end of the medical lead body, wherein rotation of the second rotatable member varies an overall length of the medical lead.

Example 12B. The assembly of example 11B, wherein the mechanically adjustable medical lead includes a threaded joint that transfers the rotation of the second rotatable member to vary the overall length of the medical lead.

Example 13B. The assembly of example 9B, wherein the retractable electrode is a first electrode, the insulated conductor is a first insulated conductor and the rotatable member is a first rotatable member, the mechanically adjustable medical lead further comprising: a second electrode located adjacent a distal end of the medical lead body; a third electrode located more proximally along the medical lead body as compared to the second electrode; a second insulated conductor extending within the medical lead body, the second insulated conductor being in electrical contact with the second electrode and extending to the proximal end of the medical lead body; a third insulated conductor extending within the medical lead body, the third insulated conductor being in electrical contact with the third electrode and extending to the proximal end of the medical lead body; a second rotatable member positioned adjacent to the proximal end of the medical lead body, wherein rotation of the second rotatable member moves a position of the third electrode along the medical lead body to adjust a spacing between the second electrode and the third electrode.

Example 14B. The assembly of example 13B, wherein the mechanically adjustable medical lead includes a threaded joint that transfers the rotation of the second rotatable member into substantially linear movement to move the position of the third electrode.

Example 15B. The assembly of example 9B, further comprising: a sealed housing, the motor being within the sealed housing; a nutating shaft, wherein a proximal end of the nutating shaft is coupled to the rotating output shaft and within the sealed housing; a central bearing passing through the sealed housing and supporting a central portion of the nutating shaft and within the sealed housing; and a flexible seal, a proximal side of the flexible seal covering a distal side of the central bearing, and a distal side of the flexible seal being secured to a distal portion of the nutating shaft located distally relative to the central bearing, wherein the sealed housing and the flexible seal combine to form a substantially sealed enclosure encasing the motor, the rotating output shaft, the proximal end of the nutating shaft and the central bearing.

Example 16B. The assembly of example 15B, wherein the flexible seal includes a metal bellows.

Example 17B. The assembly of example 15B, wherein the sealed housing and the flexible seal combine to form a hermetically sealed enclosure encasing the motor, the rotating output shaft, the proximal end of the nutating shaft and the central bearing.

Example 18B. The assembly of example 9B, further comprising a stimulation generator configured to deliver electrical stimulation via the electrode of the medical lead, wherein the stimulation generator is electrically coupled to the electrode of the medical lead.

Example 19B. A method comprising operating a motor to drive a rotating output shaft of a motor and deploy a retractable electrode of a mechanically adjustable medical lead, wherein the mechanically adjustable medical lead comprises: an elongated medical lead body; the retractable electrode, the retractable electrode being extendable from a distal portion of the medical lead body; an insulated conductor extending within the medical lead body, the insulated conductor being in electrical contact with the retractable electrode and extending to a proximal end of the medical lead body; and a rotatable member positioned adjacent to the proximal end of the medical lead body, wherein the rotatable member is mechanically coupled to and configured to be driven by the rotating output shaft of the motor, wherein rotation of the rotatable member moves a position of the retractable electrode to selectively deploy and retract the retractable electrode from the medical lead body.

Example 20B. The method of example 19B, further comprising operating the motor to drive the rotating output shaft of the motor and retract the deployed retractable electrode of the mechanically adjustable medical lead.

Example 21B. The method of example 19B, further comprising, delivering, via a simulation generator, electrical simulation to a patient via the deployed retractable electrode.

Example 22B. The method of example 19B, further comprising, sensing a physiological condition of a patient via the deployed retractable electrode.

Example 23B. The method of example 19B, further comprising receiving a force signal from a force sensor, the force signal representing a resistance to movement of a position of the retractable electrode of the medical lead, wherein operating the motor to drive the rotating output shaft of the motor and deploy the retractable electrode of the mechanically adjustable medical lead is based on the force signal.

Example 24B. The method of example 23B, wherein operating the motor to drive the rotating output shaft of the motor and deploy the retractable electrode of the mechanically adjustable medical lead includes limiting movement of the retractable electrode to prevent resistance to the movement of the retractable electrode from exceeding a predefined value.

Example 1C. An assembly comprising: a motor including a rotating output shaft; and a mechanically adjustable medical lead, the mechanically adjustable medical lead comprising: an elongated medical lead body; an electrode located at a distal portion of the medical lead body; an insulated conductor extending within the medical lead body, the insulated conductor being in electrical contact with the electrode and extending to a proximal end of the medical lead body; and a rotatable member positioned adjacent to the proximal end of the medical lead body, wherein the rotatable member is mechanically coupled to and configured to be driven by the rotating output shaft of the motor such that rotation of the rotatable member moves a position of the electrode to adjust a spacing between the proximal end of the medical lead body and the electrode.

Example 2C. The assembly of example 1C, wherein the mechanically adjustable medical lead includes a threaded joint that transfers the rotation of the rotatable member into substantially linear movement to move the position of the electrode.

Example 3C. The assembly of example 1C, wherein the electrode is positioned adjacent a distal end of the medical lead and rotation of the rotatable member varies an overall length of the medical lead.

Example 4C. The assembly of example 3C, wherein the mechanically adjustable medical lead includes a threaded joint that transfers the rotation of the rotatable member into substantially linear movement to vary the overall length of the medical lead.

Example 5C. The assembly of example 1C, wherein the electrode is a first electrode, the insulated conductor is a first insulated conductor and the rotatable member is a first rotatable member, the mechanically adjustable medical lead further comprising: a second electrode located more proximally along the medical lead body as compared to the first electrode; a second insulated conductor extending within the medical lead body, the second insulated conductor being in electrical contact with the second electrode and extending to the proximal end of the medical lead body; a second rotatable member positioned adjacent to the proximal end of the medical lead body, wherein rotation of the second rotatable member moves a position of the second electrode along the medical lead body to adjust a spacing between the first electrode and the second electrode.

Example 6C. The assembly of example 5C, wherein the mechanically adjustable medical lead includes a threaded joint that transfers the rotation of the second rotatable member into substantially linear movement to move the position of the second electrode.

Example 7C. The assembly of example 5C, wherein the first electrode is positioned adjacent a distal end of the medical lead and rotation of the first rotatable member varies an overall length of the medical lead.

Example 8C. The assembly of example 1C, further comprising: a sealed housing, the motor being within the sealed housing; a nutating shaft, wherein a proximal end of the nutating shaft is coupled to the rotating output shaft and within the sealed housing; a central bearing passing through the sealed housing and supporting a central portion of the nutating shaft and within the sealed housing; and a flexible seal, a proximal side of the flexible seal covering a distal side of the central bearing, and a distal side of the flexible seal being secured to a distal portion of the nutating shaft located distally relative to the central bearing, wherein the sealed housing and the flexible seal combine to form a substantially sealed enclosure encasing the motor, the rotating output shaft, the proximal end of the nutating shaft and the central bearing.

Example 9C. The assembly of example 8C, wherein the nutating shaft is configured to only nutate and not rotate substantially when the motor operates to rotate the rotating output shaft.

Example 10C. The assembly of example 8C, wherein the central bearing includes a radial spherical bearing.

Example 11C. The assembly of example 8C, wherein the flexible seal includes a metal bellows.

Example 12C. The assembly of example 8C, wherein the sealed housing and the flexible seal combine to form a hermetically sealed enclosure encasing the motor, the rotating output shaft, the proximal end of the nutating shaft and the central bearing.

Example 13C. The assembly of example 1C, further comprising a stimulation generator configured to deliver electrical stimulation via the electrode of the medical lead, wherein the stimulation generator is electrically coupled to the electrode of the medical lead via the conductor.

Example 14C. A mechanically adjustable medical lead comprising: an elongated medical lead body; a first electrode located at a distal portion of the medical lead body; a first insulated conductor extending within the medical lead body, the first insulated conductor being in electrical contact with the first electrode and extending to a proximal end of the medical lead body; a second electrode located more proximally along the medical lead body as compared to the first electrode; a second insulated conductor extending within the medical lead body, the second insulated conductor being in electrical contact with the second electrode and extending to the proximal end of the medical lead body; and a rotatable member positioned adjacent to the proximal end of the medical lead body, wherein rotation of the rotatable member moves a position of the second electrode along the medical lead body to adjust a spacing between the first electrode and the second electrode.

Example 15C. The medical lead of example 14C, wherein the mechanically adjustable medical lead includes a threaded joint that transfers the rotation of the rotatable member into substantially linear movement to move the position of the second electrode.

Example 16C. The medical lead of example 14C, wherein the rotatable member is a first rotatable member, the mechanically adjustable medical lead further comprising a second rotatable member positioned adjacent to the proximal end of the medical lead body, wherein rotation of the second rotatable member varies an overall length of the medical lead.

Example 17C. The medical lead of example 16C, wherein the mechanically adjustable medical lead includes a threaded joint that transfers the rotation of the second rotatable member into substantially linear movement to vary the overall length of the medical lead.

Example 18C. The medical lead of example 14C, further comprising: a sealed housing, a motor being within the sealed housing and including a rotating output shaft; a nutating shaft, wherein a proximal end of the nutating shaft is coupled to the rotating output shaft and within the sealed housing; a central bearing passing through the sealed housing and supporting a central portion of the nutating shaft and within the sealed housing; and a flexible seal, a proximal side of the flexible seal covering a distal side of the central bearing, and a distal side of the flexible seal being secured to a distal portion of the nutating shaft located distally relative to the central bearing, wherein the sealed housing and the flexible seal combine to form a substantially sealed enclosure encasing the motor, the rotating output shaft, the proximal end of the nutating shaft and the central bearing.

Example 19C. The medical lead of example 18C, wherein the nutating shaft is configured to only nutate and not rotate substantially when motor operates to rotate the rotating output shaft.

Example 20C. The medical lead of example 18C, wherein the central bearing includes a radial spherical bearing.

Example 21C. The medical lead of example 18C, wherein the flexible seal includes a metal bellows.

Example 22C. The medical lead of example 21C, further comprising: a first weld joint sealing an interface of the metal bellows and the sealed housing; and a second weld joint sealing an interface of the metal bellows and the nutating shaft.

Example 23C. The medical lead of example 18C, wherein the sealed housing and the flexible seal combine to form a hermetically sealed enclosure encasing the motor, the rotating output shaft, the proximal end of the nutating shaft and the central bearing.

Example 24C. The medical lead of example 14C, further comprising a stimulation generator configured to deliver electrical stimulation via the electrode of the medical lead, wherein the stimulation generator is electrically coupled to the electrode of the medical lead via the first insulated conductor.

Example 25C. The medical lead of example 14C, wherein the medical lead body has a substantially circular cross-sectional shape.

Example 26C. The medical lead of example 14C, wherein the medical lead comprises a deep brain stimulation (DBS) medical lead.

Example 27C. A method comprising: operating a motor to drive a rotating output shaft of a motor and move a position of an electrode of a mechanically adjustable medical lead, wherein the mechanically adjustable medical lead comprises: an elongated medical lead body; the electrode, the electrode being located at a distal portion of the medical lead body; an insulated conductor extending within the medical lead body, the insulated conductor being in electrical contact with the electrode and extending to a proximal end of the medical lead body; and a rotatable member positioned adjacent to the proximal end of the medical lead body, wherein the rotatable member is mechanically coupled to and configured to be driven by the rotating output shaft of the motor, wherein rotation of the rotatable member moves the position of the electrode to adjust a spacing between the proximal end of the medical lead body and the electrode.

Example 28C. The method of example 27C, wherein the electrode is positioned adjacent a distal end of the medical lead and rotation of the rotatable member varies an overall length of the medical lead.

Example 29C. The method of example 27C, wherein the motor is a first motor, wherein the electrode is a first electrode, the insulated conductor is a first insulated conductor and the rotatable member is a first rotatable member, the mechanically adjustable medical lead further comprising: second electrode located more proximally along the medical lead body as compared to the first electrode; a second insulated conductor extending within the medical lead body, the second insulated conductor being in electrical contact with the second electrode and extending to the proximal end of the medical lead body; a second rotatable member positioned adjacent to the proximal end of the medical lead body, the method further comprising operating a second motor to drive the second rotatable member of the medical lead to move a position of the second electrode along the medical lead body to adjust a spacing between the first electrode and the second electrode.

Example 30. The method of example 27C, wherein the motor and the medical lead are included within an assembly, the assembly further comprising: a sealed housing, the motor being within the sealed housing; a nutating shaft, wherein a proximal end of the nutating shaft is coupled to the rotating output shaft and within the sealed housing; a central bearing passing through the sealed housing and supporting a central portion of the nutating shaft and within the sealed housing; and a flexible seal, a proximal side of the flexible seal covering a distal side of the central bearing, and a distal side of the flexible seal being secured to a distal portion of the nutating shaft located distally relative to the central bearing, wherein the sealed housing and the flexible seal combine to form a substantially sealed enclosure encasing the motor, the rotating output shaft, the proximal end of the nutating shaft and the central bearing.

Example 31C. A method of adjusting a mechanically adjustable medical lead, wherein the mechanically adjustable medical lead includes an electrode and a rotatable member, the rotatable member being mechanically coupled to the electrode, the method comprising: monitoring a physiological condition of a patient; and operating, based on the monitored physiological condition, a motor to drive the rotatable member of the medical lead via a rotating output shaft of the motor and move a position of the electrode to adjust a position of the electrode.

Example 32C. The method of example 31C, monitoring the physiological condition of the patient includes monitoring the physiological condition of the patient via the electrode.

Example 33C. The method of example 31C, wherein the electrode is positioned adjacent a distal end of the medical lead and rotation of the rotatable member varies an overall length of the medical lead.

Example 34C. The method of example 31C, wherein the mechanically adjustable medical lead further includes: an elongated medical lead body, wherein the electrode is located at a distal portion of the medical lead body and the rotatable member positioned adjacent to the proximal end of the medical lead body; and an insulated conductor extending within the medical lead body, the insulated conductor being in electrical contact with the electrode and extending to the proximal end of the medical lead body.

Example 35C. The method of example 34C, wherein the motor is a first motor, wherein the electrode is a first electrode, the insulated conductor is a first insulated conductor and the rotatable member is a first rotatable member, the mechanically adjustable medical lead further comprising: a second electrode located more proximally along the medical lead body as compared to the first electrode; a second insulated conductor extending within the medical lead body, the second insulated conductor being in electrical contact with the second electrode and extending to the proximal end of the medical lead body; a second rotatable member positioned adjacent to the proximal end of the medical lead body, the method further comprising operating, based on the physiological condition, a second motor to drive the second rotatable member of the medical lead to move a position of the second electrode along the medical lead body to adjust a spacing between the first electrode and the second electrode.

Example 36C. The method of example 31C, wherein the motor and the medical lead are included within an assembly, the assembly further comprising: a sealed housing, the motor being within the sealed housing; a nutating shaft, wherein a proximal end of the nutating shaft is coupled to the rotating output shaft and within the sealed housing; a central bearing passing through the sealed housing and supporting a central portion of the nutating shaft and within the sealed housing; and a flexible seal, a proximal side of the flexible seal covering a distal side of the central bearing, and a distal side of the flexible seal being secured to a distal portion of the nutating shaft located distally relative to the central bearing, wherein the sealed housing and the flexible seal combine to form a substantially sealed enclosure encasing the motor, the rotating output shaft, the proximal end of the nutating shaft and the central bearing.

Example 37C. The method of example 31C, wherein the physiological condition includes one or more of a group consisting of: patient brain signals; patient activity level; patient posture; patient tremors; and patient sleep characteristics.

Example 38C. The method of example 31C, further comprising selecting the position of the electrode based on the monitored physiological condition of the patient to enhance either the detection of the monitored physiological condition of the patient or improve the efficacy of a therapy delivered via the electrode.

Example 39C. The method of example 31C, wherein operating the motor to drive the rotatable member of the medical lead adjusts a spacing between a proximal end of the medical lead and the electrode.

Example 1D. An assembly comprising: a processor; a motor including a rotating output shaft; a mechanically adjustable medical lead including an electrode, a medical lead body, an insulated conductor extending within the medical lead body, the insulated conductor being in electrical contact with the electrode and extending to a proximal end of the medical lead body, and a rotatable member, the rotatable member being mechanically coupled to the electrode, wherein rotation of the rotating output shaft rotates the rotatable member of the medical lead to move a position of the electrode to adjust a spacing between a proximal end of the medical lead and the electrode; and a force sensor configured to measure a resistance to movement of the position of the electrode and deliver a force signal to the processor based on the resistance to movement of the position of the electrode, wherein the processor is configured to operate the motor to adjust the spacing between the proximal end of the medical lead body and the electrode based on the force signal from the force sensor.

Example 2D. The assembly of example 1D, wherein the mechanically adjustable medical lead further includes: an elongated medical lead body, wherein the electrode is located at a distal portion of the medical lead body and the rotatable member positioned adjacent to the proximal end of the medical lead body; and an insulated conductor extending within the medical lead body, the insulated conductor being in electrical contact with the electrode and extending to the proximal end of the medical lead body.

Example 3D. The assembly of example 1D, wherein the mechanically adjustable medical lead includes a threaded joint that transfers the rotation of the rotatable member into substantially linear movement to move the position of the electrode.

Example 4D. The assembly of example 1D, wherein the electrode is positioned adjacent a distal end of the medical lead and rotation of the rotatable member varies an overall length of the medical lead.

Example 5D. The assembly of example 4D, wherein the mechanically adjustable medical lead includes a threaded joint that transfers the rotation of the rotatable member into substantially linear movement to vary the overall length of the medical lead.

Example 6D. The assembly of example 1D, wherein the electrode is a first electrode, the insulated conductor is a first insulated conductor and the rotatable member is a first rotatable member, the mechanically adjustable medical lead further comprising: a second electrode located more proximally along the medical lead body as compared to the first electrode; a second insulated conductor extending within the medical lead body, the second insulated conductor being in electrical contact with the second electrode and extending to the proximal end of the medical lead body; a second rotatable member positioned adjacent to the proximal end of the medical lead body, wherein rotation of the second rotatable member moves a position of the second electrode along the medical lead body to adjust a spacing between the first electrode and the second electrode.

Example 7D. The assembly of example 6D, wherein the first electrode is positioned adjacent a distal end of the medical lead and rotation of the first rotatable member varies an overall length of the medical lead.

Example 8D. The assembly of example 1D, further comprising: a sealed housing, the motor being within the sealed housing; a nutating shaft, wherein a proximal end of the nutating shaft is coupled to the rotating output shaft and within the sealed housing; a central bearing passing through the sealed housing and supporting a central portion of the nutating shaft and within the sealed housing; and a flexible seal, a proximal side of the flexible seal covering a distal side of the central bearing, and a distal side of the flexible seal being secured to a distal portion of the nutating shaft located distally relative to the central bearing, wherein the sealed housing and the flexible seal combine to form a substantially sealed enclosure encasing the motor, the rotating output shaft, the proximal end of the nutating shaft and the central bearing.

Example 9D. The assembly of example 8D, wherein the flexible seal includes a metal bellows.

Example 10D. The assembly of example 8D, wherein the sealed housing and the flexible seal combine to form a hermetically sealed enclosure encasing the motor, the rotating output shaft, the proximal end of the nutating shaft and the central bearing.

Example 11D. The assembly of example 1D, further comprising a stimulation generator configured to deliver electrical stimulation via the electrode of the medical lead, wherein the stimulation generator is electrically coupled to the electrode of the medical lead.

Example 12D. The assembly of example 1D, wherein the processor is configured to operate the motor to adjust the spacing between the proximal end of the medical lead body and the electrode based on the force signal from the force sensor at least in part by limiting movement of the position of the electrode to prevent the resistance to movement of the position of the electrode from exceeding a predefined value.

Example 13D. The assembly of example 1D, wherein the force sensor includes a piezoelectric sensor.

Example 14D. A mechanically adjustable medical lead comprising: an elongated medical lead body; a first electrode located at a distal portion of the medical lead body; a first insulated conductor extending within the medical lead body, the first insulated conductor being in electrical contact with the first electrode and extending to a proximal end of the medical lead body; a second electrode located more proximally along the medical lead body as compared to the first electrode; a second insulated conductor extending within the medical lead body, the second insulated conductor being in electrical contact with the second electrode and extending to the proximal end of the medical lead body; a rotatable member positioned adjacent to the proximal end of the medical lead body, wherein rotation of the rotatable member moves a position of the second electrode along the medical lead body to adjust a spacing between the first electrode and the second electrode; and a force sensor configured to measure a resistance to movement of the position of the second electrode and deliver a force signal to a processor based on the resistance to movement of the position of the second electrode.

Example 15D. The medical lead of example 14D, wherein the mechanically adjustable medical lead includes a threaded joint that transfers the rotation of the rotatable member into substantially linear movement to move the position of the second electrode.

Example 16D. The medical lead of example 14D, wherein the rotatable member is a first rotatable member, the mechanically adjustable medical lead further comprising a second rotatable member positioned adjacent to the proximal end of the medical lead body, wherein rotation of the second rotatable member varies an overall length of the medical lead.

Example 17D. The medical lead of example 16D, wherein the mechanically adjustable medical lead includes a threaded joint that transfers the rotation of the second rotatable member into substantially linear movement to vary the overall length of the medical lead.

Example 18D. The medical lead of example 14D, further comprising: a sealed housing, a motor being within the sealed housing and including a rotating output shaft; a nutating shaft, wherein a proximal end of the nutating shaft is coupled to the rotating output shaft and within the sealed housing; a central bearing passing through the sealed housing and supporting a central portion of the nutating shaft and within the sealed housing; and a flexible seal, a proximal side of the flexible seal covering a distal side of the central bearing, and a distal side of the flexible seal being secured to a distal portion of the nutating shaft located distally relative to the central bearing, wherein the sealed housing and the flexible seal combine to form a substantially sealed enclosure encasing the motor, the rotating output shaft, the proximal end of the nutating shaft and the central bearing.

Example 19D. The medical lead of example 18D, wherein the flexible seal includes a metal bellows.

Example 20D. The medical lead of example 18D, wherein the sealed housing and the flexible seal combine to form a hermetically sealed enclosure encasing the motor, the rotating output shaft, the proximal end of the nutating shaft and the central bearing.

Example 21D. The medical lead of example 14D, further comprising a stimulation generator configured to deliver electrical stimulation via the electrode of the medical lead, wherein the stimulation generator is electrically coupled to the electrode of the medical lead.

Example 22D. The medical lead of example 14D, wherein the medical lead body has a substantially circular cross-sectional shape.

Example 23D. The medical lead of example 14D, wherein the medical lead comprises a deep brain stimulation (DBS) medical lead.

Example 24D. The medical lead of example 14D, wherein the force sensor includes a piezoelectric sensor.

Example 25D. A method of adjusting a mechanically adjustable medical lead, wherein the mechanically adjustable medical lead includes an electrode and a rotatable member, the rotatable member being mechanically coupled to the electrode, the method comprising: receiving a force signal from a force sensor, the force signal representing a resistance to movement of the position of the electrode of the medical lead; and operating, based on the force signal, a motor to drive the rotatable member of the medical lead via a rotating output shaft of the motor and move a position of the electrode to adjust a spacing between a proximal end of the medical lead and the electrode.

Example 26D. The method of example 25D, wherein operating, based on the force signal, the motor to drive the rotatable member of the medical lead and move the position of the electrode to adjust the spacing between the proximal end of the medical lead and the electrode includes limiting movement of the position of the electrode to prevent resistance to movement of the position of the electrode from exceeding a predefined value.

Example 27D. The method of example 25D, wherein the electrode is positioned adjacent a distal end of the medical lead and rotation of the rotatable member varies an overall length of the medical lead.

Example 28D. The method of example 25D, wherein the mechanically adjustable medical lead further includes: an elongated medical lead body, wherein the electrode is located at a distal portion of the medical lead body and the rotatable member positioned adjacent to the proximal end of the medical lead body; and an insulated conductor extending within the medical lead body, the insulated conductor being in electrical contact with the electrode and extending to the proximal end of the medical lead body.

Example 29D. The method of example 28D, wherein the electrode is a first electrode, the insulated conductor is a first insulated conductor and the rotatable member is a first rotatable member, the mechanically adjustable medical lead further comprising: a second electrode located more proximally along the medical lead body as compared to the first electrode; a second insulated conductor extending within the medical lead body, the second insulated conductor being in electrical contact with the second electrode and extending to the proximal end of the medical lead body; a second rotatable member positioned adjacent to the proximal end of the medical lead body, the method further comprising: mechanically coupling the motor to the second rotatable member; and operating, based on the force signal, the motor to drive the second rotatable member of the medical lead to move a position of the second electrode along the medical lead body to adjust a spacing between the first electrode and the second electrode.

Example 30D. The method of example 25D, wherein the motor and the medical lead are included within an assembly, the assembly further comprising: a sealed housing, the motor being within the sealed housing; a nutating shaft, wherein a proximal end of the nutating shaft is coupled to the rotating output shaft and within the sealed housing; a central bearing passing through the sealed housing and supporting a central portion of the nutating shaft and within the sealed housing; and a flexible seal, a proximal side of the flexible seal covering a distal side of the central bearing, and a distal side of the flexible seal being secured to a distal portion of the nutating shaft located distally relative to the central bearing, wherein the sealed housing and the flexible seal combine to form a substantially sealed enclosure encasing the motor, the rotating output shaft, the proximal end of the nutating shaft and the central bearing.

Example 1E. An assembly comprising: a sealed housing; a motor within the sealed housing, the motor including a rotating output shaft; a first coaxial shaft within the sealed housing, the first coaxial shaft being mechanically coupled to the rotating output shaft such that rotation of the rotating output shaft drives rotation of the first coaxial shaft; a second coaxial shaft external to the sealed housing, the second coaxial shaft being in axial alignment with the first coaxial shaft; an offset pin mechanically coupling the first coaxial shaft to the second coaxial shaft, wherein rotation of the rotating first coaxial shaft drives a circular motion of the offset pin about the axis of the first coaxial shaft, wherein the circular motion of the offset pin drives rotation of the second coaxial shaft; and a flexible seal including an oscillating cap, the oscillating cap being mechanically coupled to the offset pin such that the oscillating cap oscillates in unison with the circular motion of the offset pin, wherein the sealed housing and the flexible seal combine to form a substantially sealed enclosure encasing the motor and the first coaxial shaft.

Example 2E. The assembly of example 1E, further comprising: a first bearing between the first coaxial shaft and the oscillating cap; and a second bearing between the first coaxial shaft and the offset pin, wherein the first and second bearing combine to allow the oscillating cap to oscillate without rotating while the first coaxial shaft and the second coaxial shaft rotate.

Example 3E. The assembly of example 2E, wherein the offset pin and the oscillating cap are fixed relative to one another as a functionally unitary component, wherein the first bearing is between the first coaxial shaft and the unitary component, and wherein the second bearing is between the second coaxial shaft and the unitary component.

Example 4E. The assembly of example 2E, wherein the offset pin and the second coaxial shaft are fixed relative to one another as a functionally unitary component, wherein the first bearing is between the first coaxial shaft and the oscillating cap, and wherein the second bearing is between the oscillating cap and the unitary component.

Example 5E. The assembly of example 2E, wherein the offset pin and the first coaxial shaft are fixed relative to one another as a functionally unitary component, wherein the first bearing is between the unitary component and the oscillating cap, and wherein the second bearing is between the oscillating cap and the second coaxial shaft.

Example 6E. The assembly of example 1E, wherein the flexible seal includes a metal bellows.

Example 7E. The assembly of example 6E, wherein the metal bellows includes an electroformed metal bellows.

Example 8E. The assembly of example 6E, further comprising: a first weld joint sealing an interface of the metal bellows and the sealed housing; and a second weld joint sealing an interface of the metal bellows and the oscillating cap.

Example 9E. The assembly of example 1E, wherein the sealed housing and the flexible seal combine to form a hermetically sealed enclosure encasing the motor and the first coaxial shaft.

Example 10E. The assembly of example 1E, further comprising a mechanically adjustable medical lead, the mechanically adjustable medical lead including a rotatable member mechanically connected to a distal end of the second coaxial shaft, wherein operation of the motor to rotate the second coaxial shaft rotates the rotatable member of the mechanically adjustable medical lead to move a position of an electrode of the mechanically adjustable medical lead to adjust a spacing between a proximal end of the medical lead body and the electrode.

Example 11E. The assembly of example 1E, further comprising a mechanically adjustable medical lead, the mechanically adjustable medical lead including a rotatable member mechanically connected to a distal end of the second coaxial shaft, wherein operation of the motor to rotate the rotating output shaft rotates the rotatable member of the mechanically adjustable medical lead to move a radial orientation an electrode of the mechanically adjustable medical lead.

Example 12E. A method of manufacture for an assembly comprising: a sealed housing; a motor within the sealed housing, the motor including a rotating output shaft; a first coaxial shaft within the sealed housing, the first coaxial shaft being mechanically coupled to the rotating output shaft such that rotation of the rotating output shaft drives rotation of the first coaxial shaft; a second coaxial shaft external to the sealed housing, the second coaxial shaft being in axial alignment with the first coaxial shaft; an offset pin mechanically coupling the first coaxial shaft to the second coaxial shaft, wherein rotation of the rotating first coaxial shaft drives a circular motion of the offset pin about the axis of the first coaxial shaft, wherein the circular motion of the offset pin drives rotation of the second coaxial shaft; and a flexible seal including a flexible portion and an oscillating cap, the oscillating cap being mechanically coupled to the offset pin such that the oscillating cap oscillates in unison with the circular motion of the offset pin, the method comprising: forming a first hermetic seal at an interface between the oscillating cap and the flexible portion of the flexible seal; and forming a second hermetic seal at an interface between the sealed housing and a flexible seal, wherein the sealed housing, the flexible seal including the flexible portion and the oscillating cap, the first hermetic seal and the second hermetic seal combine to form a hermetically sealed enclosure encasing the motor and the first coaxial shaft.

Example 13E. The method of example 12E, wherein the flexible seal includes a metal bellows.

Example 14E. The method of example 13E, further comprising electroforming the metal bellows.

Example 15E. The method of example 12E, further comprising mechanically coupling a distal end of the second coaxial shaft to a rotatable member of a mechanically adjustable medical lead, wherein rotation of the second coaxial shaft is configured to rotate the rotatable member of the mechanically adjustable medical lead to move a position of an electrode of the mechanically adjustable medical lead to adjust a spacing between a proximal end of the medical lead and the electrode.

Example 16E. The method of example 12E, further comprising mechanically coupling a distal end of the second coaxial shaft a rotatable member of a mechanically adjustable medical lead, wherein rotation of the second coaxial shaft is configured to rotate the rotatable member of the mechanically adjustable medical lead to move a radial orientation an electrode of the mechanically adjustable medical lead.

Example 17E. A method of adjusting a mechanically adjustable medical lead, wherein the mechanically adjustable medical lead includes an electrode and a rotatable member, the rotatable member being mechanically coupled to the electrode, the method comprising operating a motor within a hermetically sealed enclosure to drive the rotatable member of the medical lead and move a position of the electrode to adjust a spacing between a proximal end of the medical lead and the electrode.

Example 18E. The method of example 17E, wherein the electrode is positioned adjacent a distal end of the medical lead and rotation of the rotatable member varies an overall length of the medical lead.

Example 19E. The method of example 17E, wherein the mechanically adjustable medical lead further includes: an elongated medical lead body, wherein the electrode is located at a distal portion of the medical lead body and the rotatable member positioned adjacent to the proximal end of the medical lead body; and an insulated conductor extending within the medical lead body, the insulated conductor being in electrical contact with the electrode and extending to the proximal end of the medical lead body.

Example 20E. The method of example 17E, wherein the motor and the medical lead are part of an assembly, wherein the assembly further comprises: a sealed housing; a motor within the sealed housing, the motor including a rotating output shaft; a first coaxial shaft within the sealed housing, the first coaxial shaft being mechanically coupled to the rotating output shaft such that rotation of the rotating output shaft drives rotation of the first coaxial shaft; a second coaxial shaft external to the sealed housing, the second coaxial shaft being in axial alignment with the first coaxial shaft; an offset pin mechanically coupling the first coaxial shaft to the second coaxial shaft, wherein rotation of the rotating first coaxial shaft drives a circular motion of the offset pin about the axis of the first coaxial shaft, wherein the circular motion of the offset pin drives rotation of the second coaxial shaft; and a flexible seal including an oscillating cap, the oscillating cap being mechanically coupled to the offset pin such that the oscillating cap oscillates in unison with the circular motion of the offset pin, wherein the sealed housing and the flexible seal combine to form the hermetically sealed enclosure encasing the motor and the first coaxial shaft.

Example 21E. The method of example 20E, wherein the flexible seal includes a metal bellows.

Example 22E. The method of example 21E, further comprising: a first weld joint sealing an interface of the metal bellows and the sealed housing; and a second weld joint sealing an interface of the metal bellows and the oscillating cap.

Example 23E. The method of example 17E, wherein the motor and the medical lead are part of an assembly, wherein the assembly further comprises: a sealed housing, wherein the motor is within the sealed housing, the motor including a rotating output shaft; a nutating shaft, wherein a proximal end of the nutating shaft is coupled to the rotating output shaft and within the sealed housing; a central bearing passing through the sealed housing and supporting a central portion of the nutating shaft and within the sealed housing; and a flexible seal, a proximal side of the flexible seal covering a distal side of the central bearing, and a distal side of the flexible seal being secured to a distal portion of the nutating shaft located distally relative to the central bearing, wherein the sealed housing and the flexible seal combine to form the hermetically sealed enclosure encasing the motor, the rotating output shaft, the proximal end of the nutating shaft and the central bearing.

Example 24E. The method of example 23E, wherein flexible seal is substantially fixed to the sealed housing and the nutating shaft.

Example 25E. The method of example 23E, wherein the nutating shaft is configured to only nutate and not rotate substantially when motor operates to rotate the rotating output shaft.

Example 26E. The method of example 23E, wherein the central bearing includes a radial spherical bearing.

Example 27E. The method of example 23E, wherein the flexible seal includes a metal bellows.

Example 28E. The method of example 27E, further comprising: a first weld joint sealing an interface of the metal bellows and the sealed housing; and a second weld joint sealing an interface of the metal bellows and the nutating shaft.

Example 29E. An assembly comprising: a sealed housing; a motor within the sealed housing, the motor including a rotating output shaft; a nutating shaft, wherein a proximal end of the nutating shaft is coupled to the rotating output shaft and within the sealed housing; a central bearing passing through the sealed housing and supporting a central portion of the nutating shaft and within the sealed housing; and a flexible seal, a proximal side of the flexible seal covering a distal side of the central bearing, and a distal side of the flexible seal being secured to a distal portion of the nutating shaft located distally relative to the central bearing, wherein the sealed housing and the flexible seal combine to form a substantially sealed enclosure encasing the motor, the rotating output shaft, the proximal end of the nutating shaft and the central bearing.

Example 30E. The assembly of example 29E, wherein flexible seal is substantially fixed to the sealed housing and the nutating shaft.

Example 31E. The assembly of example 29E, wherein the nutating shaft is configured to only nutate and not rotate substantially when motor operates to rotate the rotating output shaft.

Example 32E. The assembly of example 29E, wherein the central bearing includes a radial spherical bearing.

Example 33E. The assembly of example 29E, wherein the flexible seal includes a metal bellows.

Example 34E. The assembly of example 33E, wherein the metal bellows includes an electroformed metal bellows.

Example 35E. The assembly of example 33E, further comprising: a first weld joint sealing an interface of the metal bellows and the sealed housing; and a second weld joint sealing an interface of the metal bellows and the nutating shaft.

Example 36E. The assembly of example 29E, wherein the sealed housing and the flexible seal combine to form a hermetically sealed enclosure encasing the motor, the rotating output shaft, the proximal end of the nutating shaft and the central bearing.

Example 37E. The assembly of example 29E, further comprising a mechanically adjustable medical lead, the mechanically adjustable medical lead including a rotatable member mechanically connected to a distal end of the nutating shaft, wherein operation of the motor to rotate the rotating output shaft rotates the rotatable member of the mechanically adjustable medical lead to move a position of an electrode of the mechanically adjustable medical lead to adjust a spacing between a proximal end of the medical lead body and the electrode.

Example 38E. The assembly of example 29E, further comprising a mechanically adjustable medical lead, the mechanically adjustable medical lead including a rotatable member mechanically connected to a distal end of the nutating shaft, wherein operation of the motor to rotate the rotating output shaft rotates the rotatable member of the mechanically adjustable medical lead to move a radial orientation an electrode of the mechanically adjustable medical lead.

Example 39E. A method of manufacture comprising: mechanically coupling a rotating output shaft of a motor within a sealed housing to a proximal end of a nutating shaft, wherein the nutating shaft is supported by a central bearing passing through the sealed housing and supporting a central portion of the nutating shaft and within the sealed housing; forming a first hermetic seal at an interface between the sealed housing and a flexible seal, a proximal side of the flexible seal covering a distal side of the central bearing; and forming a second hermetic seal at an interface between a distal portion of the nutating shaft located distally relative to the central bearing and a distal side of the flexible seal, wherein the sealed housing, the flexible seal, the first hermetic seal and the second hermetic seal combine to form a hermetically sealed enclosure encasing the motor, the rotating output shaft, the proximal end of the nutating shaft and the central bearing.

Example 40E. The method of example 39E, wherein the flexible seal includes a metal bellows.

Example 41E. The method of example 39E, further comprising electroforming the metal bellows.

Example 42E. The method of example 39E, further comprising mechanically coupling a distal end of the nutating shaft to a rotatable member of a mechanically adjustable medical lead, wherein nutation of the nutating shaft is configured to rotate the rotatable member of the mechanically adjustable medical lead to move a position of an electrode of the mechanically adjustable medical lead to adjust a spacing between a proximal end of the medical lead and the electrode.

Example 43E. The method of example 39E, further comprising mechanically coupling a distal end of the nutating shaft to a rotatable member of a mechanically adjustable medical lead, wherein nutation of the nutating shaft is configured to rotate the rotatable member of the mechanically adjustable medical lead to move a radial orientation an electrode of the mechanically adjustable medical lead.

Various examples have been described, and, when possible, combinations of these examples are contemplated. However, modifications may be made to the described examples within the spirit of the present disclosure. These and other examples are within the scope of the following claims.

What is claimed is:

1. A medical device system comprising:
   an assembly comprising:
      a sealed housing;
      a motor within the sealed housing, the motor including a rotating output shaft;
      a nutating shaft, wherein a proximal end of the nutating shaft is coupled to the rotating output shaft and within the sealed housing;
      a central bearing passing through the sealed housing and supporting a central portion of the nutating shaft;
      a flexible seal, a proximal side of the flexible seal covering a distal side of the central bearing, and a distal side of the flexible seal being secured to a distal portion of the nutating shaft located distally relative to the central bearing, wherein the sealed housing and the flexible seal combine to form a substantially sealed enclosure encasing the motor, the rotating output shaft, the proximal end of the nutating shaft and the central bearing; and
      a mechanically adjustable medical lead, the mechanically adjustable medical lead having a lead body and a plurality of electrodes disposed circumferentially on and around the lead body, the mechanically adjustable medical lead includes a rotatable member mechanically connected to a distal end of the nutating shaft, wherein operation of the motor to rotate the rotating output shaft rotates the rotatable member of the mechanically adjustable medical lead to at least one of:
         move a position of an electrode, of the plurality of electrodes, disposed circumferentially on and around the lead body of the mechanically adjustable medical lead to adjust a spacing between a proximal end of the lead body and the electrode;
         adjust a spacing between the electrode, of the plurality of electrodes, disposed circumferentially on and around the lead body of the mechanically adjustable medical lead and another electrode, of the plurality of electrodes, that is also disposed circumferentially around the lead body of the mechanically adjustable medical lead; or
         move a radial orientation of the electrode, of the plurality of electrodes, disposed circumferentially on and around the lead body of the mechanically adjustable medical lead.

2. The system of claim 1, wherein the flexible seal is substantially fixed to the sealed housing and the nutating shaft.

3. The system of claim 1, wherein the nutating shaft is configured to only nutate and not rotate substantially when the motor operates to rotate the rotating output shaft.

4. The system of claim 1, wherein the central bearing includes a radial spherical bearing.

5. The system of claim 1, wherein the flexible seal includes a metal bellows.

6. The system of claim 5, wherein the metal bellows includes an electroformed metal bellows.

7. The system of claim 5, further comprising:
   a first weld joint sealing an interface of the metal bellows and the sealed housing; and
   a second weld joint sealing an interface of the metal bellows and the nutating shaft.

8. The system of claim 1, wherein the sealed housing and the flexible seal combine to form a hermetically sealed enclosure encasing the motor, the rotating output shaft, the proximal end of the nutating shaft and the central bearing.

9. The system of claim 1, wherein the electrode is configured to move linearly about a longitudinal axis of the mechanically adjustable medical lead.

10. The system of claim 1, wherein the electrode and the other electrode are configured to move linearly about a longitudinal axis of the mechanically adjustable medical lead.

11. The system of claim 1, wherein the operation of the motor to rotate the rotating output shaft rotates the rotatable member of the mechanically adjustable medical lead such that the electrode moves in a direction away from the other electrode.

12. The system of claim 1, wherein the operation of the motor to rotate the rotating output shaft rotates the rotatable member of the mechanically adjustable medical lead such that both the electrode and the other electrode move relative to a proximal end of the mechanically adjustable medical lead.

13. The system of claim 1, wherein the flexible seal comprises a first flexible seal, the assembly further comprising a second flexible seal, a distal side of the second flexible seal covering a proximal side of the central bearing, and a proximal side of the second flexible seal being secured to a proximal portion of the nutating shaft located proximally relative to the central bearing.

14. The system of claim 1, wherein the lead body of the mechanically adjustable lead additionally comprises a plurality of retractable electrodes, the plurality of retractable electrodes being insertable within the lead body and extendable beyond a profile of the lead body.

15. A method comprising operating a motor to rotate an output shaft of the motor, the motor being within a sealed housing,
   wherein a proximal end of a nutating shaft is coupled to the rotating output shaft and within the sealed housing,
   wherein a central bearing passes through the sealed housing and supports a central portion of the nutating shaft,
   wherein a proximal side of a flexible seal covers a distal side of the central bearing,
   wherein a distal side of the flexible seal is secured to a distal portion of the nutating shaft located distally relative to the central bearing, wherein the sealed housing and the flexible seal combine to form a substantially sealed enclosure encasing the motor, the rotating output shaft, the proximal end of the nutating shaft and the central bearing; and wherein operating the motor to rotate the output shaft of the motor rotates a rotatable member of a mechanically adjustable medical lead, the mechanically adjustable medical lead having a lead body and a plurality of electrodes disposed circumferentially on and around the lead body, the mechanically adjustable lead including a rotatable member mechanically connected to a distal end of the nutating shaft, wherein operation of the motor to rotate the rotating output shaft rotates the rotatable member of the mechanically adjustable lead to at least one of:

moving a position of an electrode, of the plurality of the electrodes, disposed circumferentially on and around the lead body of the mechanically adjustable medical lead to adjust a spacing between a proximal end of the lead body and the electrode;

adjusting a spacing between the electrode, of the plurality of electrodes, disposed circumferentially on and around the lead body of the mechanically adjustable medical lead and another electrode, of the plurality of electrodes, that is also disposed circumferentially around the lead body of the mechanically adjustable medical lead; or moving a radial orientation of the electrode, of the plurality of electrodes, disposed circumferentially on and around the lead body of the mechanically adjustable medical lead.

16. A method of manufacturing an assembly of a medical claim device system comprising:

mechanically coupling a rotatable output shaft of a motor within a sealed housing to a proximal end of a nutating shaft, wherein the nutating shaft is supported by a central bearing passing through the sealed housing and supporting a central portion of the nutating shaft;

forming a first hermetic seal at an interface between the sealed housing and a flexible seal, a proximal side of the flexible seal covering a distal side of the central bearing; and forming a second hermetic seal at an interface between a distal portion of the nutating shaft located distally relative to the central bearing and a distal side of the flexible seal, wherein the sealed housing, the flexible seal, the first hermetic seal and the second hermetic seal combine to form a hermetically sealed enclosure encasing the motor, the rotating output shaft, the proximal end of the nutating shaft and the central bearing;

mechanically connecting a rotatable member of a mechanically adjustable medical lead to a distal end of the nutating shaft, wherein the mechanically adjustable medical lead includes a lead body and a plurality of electrodes disposed circumferentially on and around the lead body, wherein operation of the motor to rotate the rotating output shaft is formed to rotate the rotatable member of the mechanically adjustable medical lead to at least one of:

move a position of an electrode, of the plurality of electrodes, disposed circumferentially on and around the lead body of the mechanically adjustable medical lead to adjust a spacing between a proximal end of the lead body and the electrode;

adjust a spacing between the electrode, of the plurality of electrodes, disposed circumferentially on and around the lead body of the mechanically adjustable medical lead and another electrode, of the plurality of electrodes, that is also disposed circumferentially around the lead body of the mechanically adjustable medical lead; or move a radial orientation of the electrode, of the plurality of electrodes, disposed circumferentially on and around the lead body of the mechanically adjustable medical lead.

17. The method of claim 16, wherein the flexible seal includes a metal bellows.

18. The method of claim 17, further comprising electroforming the metal bellows.

* * * * *